(12) United States Patent
McGonigle et al.

(10) Patent No.: US 10,190,134 B2
(45) Date of Patent: Jan. 29, 2019

(54) COMPOSITIONS AND METHODS FOR INSECTICIDAL CONTROL OF STINKBUGS

(71) Applicant: E. I. DU PONT DE NEMOURS AND COMPANY, Wilmington, DE (US)

(72) Inventors: Brian McGonigle, Wilmington, DE (US); James Kevin Presnail, Saint Louis, MO (US); Navdeep Singh Mutti, Wilmington, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 155 days.

(21) Appl. No.: 14/775,282

(22) PCT Filed: Mar. 13, 2014

(86) PCT No.: PCT/US2014/025274
§ 371 (c)(1),
(2) Date: Sep. 11, 2015

(87) PCT Pub. No.: WO2014/159829
PCT Pub. Date: Oct. 2, 2014

(65) Prior Publication Data
US 2016/0108425 A1   Apr. 21, 2016

Related U.S. Application Data

(60) Provisional application No. 61/779,643, filed on Mar. 13, 2013.

(51) Int. Cl.
*C12N 15/82* (2006.01)
*C12N 15/113* (2010.01)
*C07K 14/435* (2006.01)
*A01N 57/16* (2006.01)

(52) U.S. Cl.
CPC ......... *C12N 15/8286* (2013.01); *A01N 57/16* (2013.01); *C07K 14/43563* (2013.01); *C12N 15/113* (2013.01); *C12N 15/8218* (2013.01); *C12N 2310/14* (2013.01); *C12N 2310/531* (2013.01); *Y02A 40/162* (2018.01)

(58) Field of Classification Search
CPC .................................................... C12N 15/8286
USPC .......................................................... 800/279
See application file for complete search history.

(56) References Cited

U.S. PATENT DOCUMENTS

2007/0124836 A1* 5/2007 Baum .................... C07H 21/04
                                                        800/279
2011/0301223 A1   12/2011 Broglie et al.
2012/0297501 A1   11/2012 Beghyn et al.

OTHER PUBLICATIONS

Liu et al. Genbank Accession No. JQ769306 2012.*
Thomas et al. 2001, The Plant Journal 25(4):417-425.*
Colliver et al. Plant Molecular Biology 1997, 35:509-522.*
Fourgoux-Nicol et al 1999, Plant Molecular Biology 40 :857-872.*
Yibrah et al. 1993 Hereditas 118:273-280.*
International Search Report and Written Opinion for PCT/US14/25274 dated Aug. 26, 2014.

* cited by examiner

*Primary Examiner* — Li Zheng

(57) ABSTRACT

Methods and compositions are provided which employ a silencing element that, when ingested by a pest, such as a Pentatomidae plant pest, decrease the expression of a target sequence in the pest. The present invention provides various target polynucleotides set forth in any one of SEQ ID NOS: 6-12, 18-40 or active variants and fragments thereof, wherein a decrease in expression of one or more the sequences in the target pest controls the pest (i.e., has insecticidal activity). Plants, plant part, bacteria and other host cells comprising the silencing elements or an active variant or fragment thereof of the invention are also provided.

30 Claims, 3 Drawing Sheets
Specification includes a Sequence Listing.

COMPOSITIONS AND METHODS FOR INSECTICIDAL CONTROL OF STINKBUGS

CROSS-REFERENCE TO RELATED APPLICATIONS

This application claims the benefit of U.S. Provisional Application No. 61/779,643, filed on Mar. 13, 2013, which is incorporated herein by reference in its entirety.

REFERENCE TO SEQUENCE LISTING

The Sequence Listing submitted Mar. 13, 2014 as a text file named "36446_0006U1_2013_03_13_Sequences_as_Filed," created on Mar. 7, 2014, and having a size of 133,534 bytes is hereby incorporated by reference pursuant to 37 C.F.R. § 1.52(e)(5).

FIELD OF THE INVENTION

The present invention relates generally to methods of molecular biology and gene silencing to control pests.

BACKGROUND OF THE INVENTION

Insect pests are a serious problem in agriculture. They destroy millions of acres of staple crops such as corn, soybeans, peas, and cotton. Yearly, these pests cause over $100 billion dollars in crop damage in the U.S. alone. In an ongoing seasonal battle, farmers must apply billions of gallons of synthetic pesticides to combat these pests. Other methods employed in the past delivered insecticidal activity by microorganisms or genes derived from microorganisms expressed in transgenic plants. For example, certain species of microorganisms of the genus *Bacillus* are known to possess pesticidal activity against a broad range of insect pests including *Lepidoptera, Diptera, Coleoptera, Hemiptera*, and others. In fact, microbial pesticides, particularly those obtained from *Bacillus* strains, have played an important role in agriculture as alternatives to chemical pest control. Agricultural scientists have developed crop plants with enhanced insect resistance by genetically engineering crop plants to produce insecticidal proteins from *Bacillus*. For example, corn and cotton plants genetically engineered to produce Cry toxins (see, e.g., Aronson (2002) *Cell Mol. Life Sci.* 59(3):417-425; Schnepf et al. (1998) *Microbiol. Mol. Biol. Rev.* 62(3):775-806) are now widely used in American agriculture and have provided the farmer with an alternative to traditional insect-control methods. However, these Bt insecticidal proteins only protect plants from a relatively narrow range of pests. Moreover, these modes of insecticidal activity provided varying levels of specificity and, in some cases, caused significant environmental consequences.

Previous control of stinkbugs relied on broad spectrum insecticides. With the adoption of transgenic controls for major lepidopteran pests in several crops, these insecticides are no longer used and stinkbugs have become a major secondary pest. No successful use of transgenic control of stinkbugs has been described or adopted. This may be due in part to the extra oral digestion employed by stinkbugs where digestive enzymes are injected into the host plant prior to feeding. This makes it difficult to find proteins that survive long enough to manifest activity against these insects. RNAi may overcome that feeding behavior by relying on double stranded RNAs rather than proteins. Thus, there is an immediate need for alternative methods to control pests.

BRIEF SUMMARY OF THE INVENTION

Methods and compositions are provided which employ a silencing element that, when ingested by a pest, such as a Pentatomidae plant pest including for example, a *N. viridula* (southern green stinkbug), *Acrosternum hilare* (green stinkbug), *Piezodorus guildini* (redbanded stinkbug), *Euschistus servus* (brown stinkbug), and/or *Halymorpha halys* (brown marmorated stinkbug) plant pest, is capable of decreasing the expression of a target sequence in the pest. In specific embodiments, the decrease in expression of the target sequence controls the pest and thereby the methods and compositions are capable of limiting damage to a plant. The present invention provides various target polynucleotides as set forth in SEQ ID NOS: 6-12, 18-40, or active variants or fragments thereof, or complements thereof, wherein a decrease in expression of one or more the sequences in the target pest controls the pest (i.e., has insecticidal activity). Further provided are silencing elements, which when ingested by the pest, decrease the level of expression of one or more of the target polynucleotides. Plants, plant parts, plant cells, bacteria and other host cells comprising the silencing elements or an active variant or fragment thereof are also provided.

In another embodiment, a method for controlling a pest, such as a Pentatomidae plant pest, such as, for example, a *N. viridula, Acrosternum hilare, Piezodorus guildini, Euschistus servus* (brown stinkbug), and/or *Halymorpha halys* plant pest, is provided. The method comprises feeding to a pest a composition comprising a silencing element, wherein the silencing element, when ingested by the pest, reduces the level of a target sequence in the pest and thereby controls the pest. Further provided are methods to protect a plant from a pest. Such methods comprise introducing into the plant or plant part, or alternatively onto the plant as part of a topical formulation, a silencing element of the invention. When the pest ingests a plant comprising the silencing element, the level of the target sequence is decreased in the pest and the pest is controlled.

In specific embodiments, the silencing element comprises at least 15, 20, or 22 consecutive nucleotides of any one or more of SEQ ID NOS: 6-12, 18-40. In specific embodiments, the pest that is controlled is a Pentatomidae plant pest, such as, for example, a *N. viridula, Acrosternum hilare, Piezodorus guildini, Euschistus servus* (brown stinkbug), and/or *Halymorpha halys* plant pest. Plants, plant parts, plant cells, bacteria and other host cells comprising the silencing element comprising at least 15, 20, or 22 consecutive nucleotides of any one or more of SEQ ID NOS: 6-12, 18-40 or an active variant or fragment thereof, or complements thereof, are also provided.

In another embodiment, a method for controlling a pest, such as a pest from Pentatomidae plant pest, such as, for example, a *N. viridula, Acrosternum hilare, Piezodorus guildini, Euschistus servus* (brown stinkbug), and/or *Halymorpha halys* (Hemiptera order) is provided. The method comprises feeding to a pest a composition comprising a silencing element comprising at least 15, 20, or 22 consecutive nucleotides of any one or more of SEQ ID NOS: 6-12, 18-40, wherein the silencing element, when ingested by the pest, reduces the level of a target sequence in the pest and thereby controls the pest. Further provided are methods to protect a plant from a pest. Such methods comprise introducing into the plant or plant part, or alternatively onto the plant as part of a topical formulation, a silencing element of the invention. When the pest ingests a plant expressing the silencing element, the level of the target sequence is decreased in the pest and the pest is controlled.

DETAILED DESCRIPTION OF THE INVENTION

Figure 1:
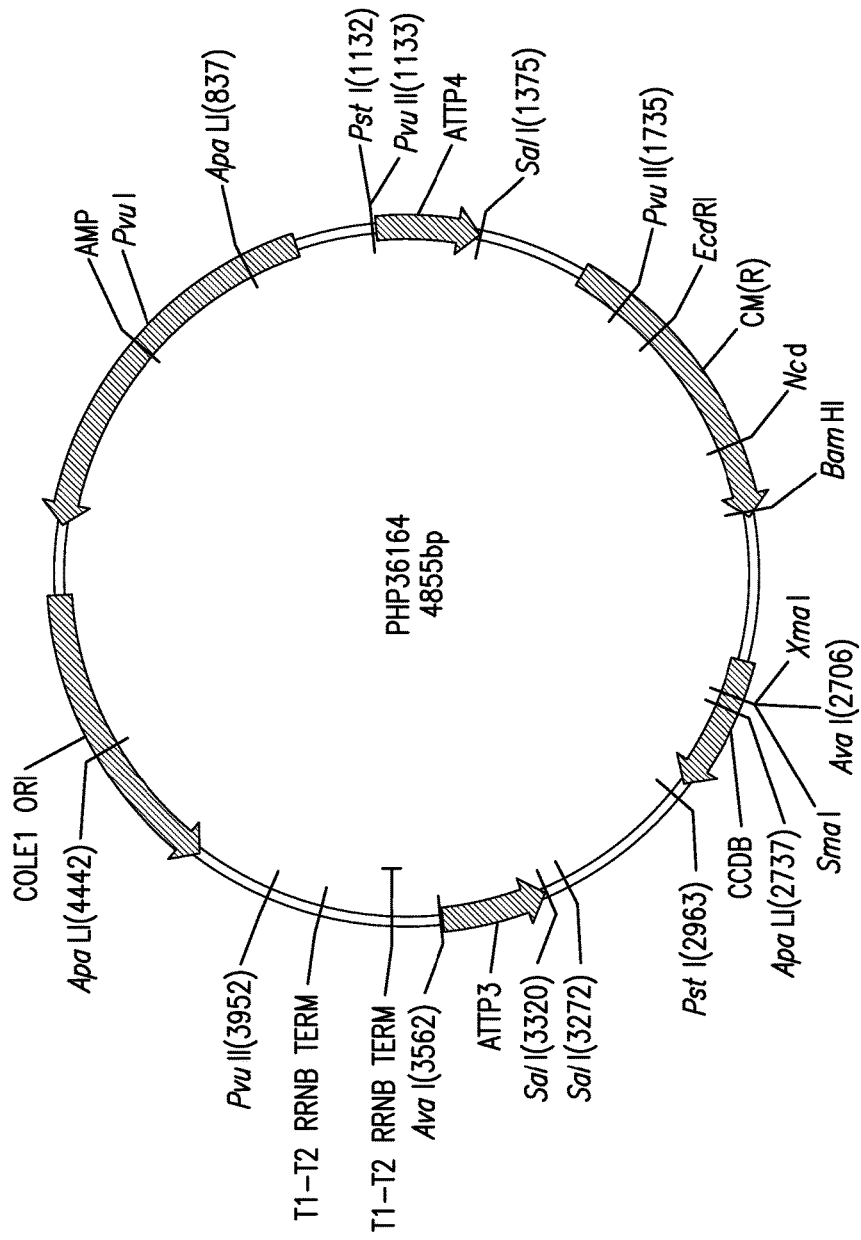
FIG. 1 is a map of plasmid PHP 36164.

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout. It is to be understood that this invention is not limited to the particular methodology, protocols, cell lines, genera, and reagents described, as such may vary. It is also to be understood that the terminology used herein is for the purpose of describing particular embodiments only, and is not intended to limit the scope of the present invention.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

I. Overview

The present invention comprises methods and compositions employing one or more silencing elements that, when ingested by a pest, such as a Pentatomidae plant pest such as, for example, a *N. viridula, Acrosternum hilare, Piezodorus guildini,* and/or *Halymorpha halys* plant pest, is capable of decreasing the expression of a target sequence in the pest. In specific embodiments, the decrease in expression of the target sequence controls the pest and thereby the methods and compositions are capable of limiting damage to a plant or plant part. The present invention provides target polynucleotides as set forth in SEQ ID NOS: 6-12, 18-40, or active variants and fragments thereof, or complements thereof. Silencing elements comprising sequences, complementary sequences, active fragments or variants of these target polynucleotides are provided which, when ingested by a pest, decrease the expression of one or more of the target sequences and thereby controls the pest (i.e., has insecticidal activity).

As used herein, by "controlling a pest" or "controls a pest" is intended any effect on a pest that results in limiting the damage that the pest causes. Controlling a pest includes, but is not limited to, killing the pest, inhibiting development of the pest, altering fertility or growth of the pest in such a manner that the pest provides less damage to the plant, decreasing the number of offspring produced, producing less fit pests, producing pests more susceptible to predator attack, or deterring the pests from eating the plant.

Reducing the level of expression of the target polynucleotide or the polypeptide encoded thereby, in the pest results in the suppression, control, and/or killing of the invading pathogenic organism. Reducing the level of expression of the target sequence of the pest will reduce the disease symptoms resulting from pathogen challenge by at least about 2% to at least about 6%, at least about 5% to about 50%, at least about 10% to about 60%, at least about 30% to about 70%, at least about 40% to about 80%, or at least about 50% to about 90% or greater. Hence, the methods of the invention can be utilized to control pests, particularly, Pentatomidae plant pests such as, for example, a *N. viridula, Acrosternum hilare, Piezodorus guildini,* and/or *Halymorpha halys* plant pest.

Assays measuring the control of a pest are commonly known in the art, as are methods to quantitate disease resistance in plants following pathogen infection. See, for example, U.S. Pat. No. 5,614,395, herein incorporated by reference. Such techniques include, measuring over time, the average lesion diameter, the pathogen biomass, and the overall percentage of decayed plant tissues. See, for example, Thomma et al. (1998) *Plant Biology* 95:15107-15111, herein incorporated by reference. See, also Baum et al. (2007) *Nature Biotech* 11:1322-1326 and WO 2007/035650 which proved both whole plant feeding assays and corn root feeding assays. Both of these references are herein incorporated by reference in their entirety. See, also the examples below.

The invention comprises compositions and methods for protecting plants from a plant pest, such as Pentatomidae plant pests such as, for example, a *N. viridula, Acrosternum hilare, Piezodorus guildini,* and/or *Halymorpha halys* plant pests or inducing resistance in a plant to a plant pest, such as Pentatomidae plant pests such as, for example, a *N. viridula, Acrosternum hilare, Piezodorus guildini,* and/or *Halymorpha halys* plant pests. As used herein "Pentatomidae plant pest" is used to refer to any member of the Pentatomidae family. Accordingly, the compositions and methods are also useful in protecting plants against any Pentatomidae plant pest including representative genera and species such as, but not limited to, *Acrocorisellus* (*A. serraticollis*), *Acrosternum* (*A. adelpha, A. hilare, A. herbidum, A. scutellatum*), *Agonoscelis* (*A. nubila*), *Alcaeorrhynchus* (*A. grandis, A. phymatophorus*), *Amaurochrous* (*A. brevitylus*), *Apateticus* (*A. anatarius, A. bracteatus, A. cynicus, A. lineolatus, A. marginiventris*), *Apoecilus, Arma* (*A. custos*), *Arvelius, Bagrada, Bagrada hilaris, Banasa* (*B. calva, B. dimiata, B. grisea, B. induta, B. sordida*), *Brochymena* (*B. affinis, B. cariosa, B. haedula, B. hoppingi, B. sulcata*), *Carbula* (*C. obtusangula, C. sinica*), *Chinavia, Chlorochroa* (*C. belfragii, C. kanei, C. norlandi, C. senilis, C. viridicata*), *Chlorocoris* (*C. distinctus, C. flaviviridis, C. hebetatus, C. subrugosus, C. tau*), *Codophila* (*C. remota, C. sulcata, C. varius*), *Coenus* (*C. delius, C. inermis, C. tarsalis*), *Cosmopepla* (*C. bimaculata, C. binotata, C. carnifex, C. decorata,*

C. intergressus), Dalpada (D. oculata), Dendrocoris (D. arizonesis, D. fruticicola, D. humeralis, D. parapini, D. reticulatus), Dolycoris (D. baccarum (sloe bug)), Dybowskyia (D. reticulata), Edessa, Erthesina (E. fullo), Eurydema (E. dominulus, E. gebleri (shield bug), E. pulchra, E. rugosa), Euschistus (E. biformis, E. integer, E. quadrator, E. servus, E. tristigma), Euthyrhynchus (E. floridanus, E. macronemis), Gonopsis (G. coccinea), Graphosoma (G. lineatum (stinkbug), G. rubrolineatum), Halyomorpha (H. halys (brown marmorated stinkbug)), Halys (H. sindillus, H. sulcatus), Holcostethus (H. abbreviatus, H. fulvipes, H. limbolarius, H. piceus, H. sphacelatus), Homalogonia (H. obtusa), Hymenarcys (H. aequalis, H. crassa, H. nervosa, H. perpuncata, H. reticulata), Lelia (L. decempunctata), Lineostethus, Loxa (L. flavicollis, L. viridis), Mecidea (M. indicia, M. major, M. minor), Megarrhamphus (M. hastatus), Menecles (M. insertus, M. portacrus), Mormidea (M. cubrosa, M. lugens, M. pama, M. pictiventris, M. ypsilon), Moromorpha (M. tetra), Murgantia (M. angularis, M. tessellata, M. varicolor, M. violascens), Neottiglossa (N. californica, N. cavifrons, N. coronaciliata, N. sulcifrons, N. undata), Nezara (N. smaragdulus, N. viridula (southern green stinkbug)), Oebalus (O. grisescens, O. insularis, O. mexicanus, O. pugnax, O. typhoeus), Oechalia (O. schellenbergii (spined predatory shield bug)), Okeanos (O. quelpartensis), Oplomus (O. catena, O. dichrous, O. tripustulatus), Palomena (P. prasina (green shield bug)), Parabrochymena, Pentatoma (P. angulata, P. illuminata, P. japonica, P. kunmingensis, P. metallifera, P. parataibaiensis, P. rufipes, P. semiannulata, P. viridicornuta), Perillus (P. bioculatus, P. confluens, P. strigipes), Picromerus (P. griseus), Piezodorus (P. degeeri, P. guildinii, P. lituratus (gorse shield bug)), Pinthaeus (P. humeralis), Plautia (P. crossota, P. stali (brown-winged green bug)), Podisus (P. maculiventris), Priassus (P. testaceus), Prionosoma, Proxys (P. albopunctulatus, P. punctulatus, P. victor), Rhaphigaster (R. nebulosa), Scotinophara (S. horvathi), Stiretrus (S. anchorago, S. fimbriatus), Thyanta (T. accerra, T. calceata, T. casta, T. perditor, T. pseudocasta), Trichopepla (T. aurora, T. dubia, T. pilipes, T. semivittata, T. vandykei), Tylospilus, and Zicrona. Other order and species for which the present invention is intended include Hemiptera, Kudzu bug, Megacopta cribraria (fa. Plataspidae) and Sunn pest, Eurygaster integriceps (fa. Scutelleridae).

II. Target Sequences

As used herein, a "target sequence" or "target polynucleotide" comprises any sequence in the pest that one desires to reduce the level of expression. In specific embodiments, decreasing the level of the target sequence in the pest controls the pest. For instance, the target sequence may be essential for growth and development. While the target sequence can be expressed in any tissue of the pest, in specific embodiments, the sequences targeted for suppression in the pest are expressed in cells of the gut tissue of the pest, cells in the midgut of the pest, and cells lining the gut lumen or the midgut. Such target sequences can be involved in, for example, gut cell metabolism, growth or differentiation. Non-limiting examples of target sequences of the invention include a polynucleotide set forth in SEQ ID NOS: 6-12, 18-40, active fragments or variants thereof, or complements thereof. As exemplified elsewhere herein, decreasing the level of expression of one or more of these target sequences in a Pentatomidae plant pest such as, for example, a N. viridula, Acrosternum hilare, Piezodorus guildini, and/or Halymorpha halys plant pest controls the pest.

III. Silencing Elements

By "silencing element" is intended a polynucleotide which when ingested by a pest, is capable of reducing or eliminating the level or expression of a target polynucleotide or the polypeptide encoded thereby. The silencing element employed can reduce or eliminate the expression level of the target sequence by influencing the level of the target RNA transcript or, alternatively, by influencing translation and thereby affecting the level of the encoded polypeptide. Methods to assay for functional silencing elements that are capable of reducing or eliminating the level of a sequence of interest are disclosed elsewhere herein. A single polynucleotide employed in the methods of the invention can comprise one or more silencing elements to the same or different target polynucleotides. The silencing element can be produced in vivo (i.e., in a host cell such as a plant or microorganism) or in vitro.

In other embodiments, while the silencing element controls pests, preferably the silencing element has no effect on the normal plant or plant part.

As discussed in further detail below, silencing elements can include, but are not limited to, a sense suppression element, an antisense suppression element, a double stranded RNA, a siRNA, an amiRNA, a miRNA, or a hairpin suppression element. Silencing elements of the present invention may comprise a chimera where two or more sequences of the present invention or active fragments or variants, or complements thereof, are found in the same RNA molecule. Further, a sequence of the present invention or active fragment or variant, or complement thereof, may be present as more than one copy in a DNA construct, silencing element, DNA molecule or RNA molecule. Non-limiting examples of silencing elements that can be employed to decrease expression of these target Pentatomidae plant pest sequences such as, for example, a N. viridula, Acrosternum hilare, Piezodorus guildini, and/or Halymorpha halys plant pest sequences comprise, or alternatively consist of, fragments and variants of the sense or antisense sequences set forth in SEQ ID NOS: 6-12, 18-40 or one or more variants or fragments thereof. The silencing element can further comprise additional sequences that advantageously effect transcription and/or the stability of a resulting transcript.

By "reduces" or "reducing" the expression level of a polynucleotide or a polypeptide encoded thereby is intended to mean, the polynucleotide or polypeptide level of the target sequence is statistically lower than the polynucleotide level or polypeptide level of the same target sequence in an appropriate control pest which is not exposed to (i.e., has not ingested) the silencing element. In particular embodiments of the invention, reducing the polynucleotide level and/or the polypeptide level of the target sequence in a pest according to the invention results in less than 95%, less than 90%, less than 80%, less than 70%, less than 60%, less than 50%, less than 40%, less than 30%, less than 20%, less than 10%, or less than 5% of the polynucleotide level, or the level of the polypeptide encoded thereby, of the same target sequence in an appropriate control pest. Methods to assay for the level of the RNA transcript, the level of the encoded polypeptide, or the activity of the polynucleotide or polypeptide are discussed elsewhere herein.

a. Sense Suppression Elements

As used herein, a "sense suppression element" comprises a polynucleotide designed to express an RNA molecule corresponding to at least a part of a target messenger RNA in the "sense" orientation. Expression of the RNA molecule comprising the sense suppression element reduces or eliminates the level of the target polynucleotide or the polypeptide encoded thereby. The polynucleotide comprising the sense suppression element may correspond to all or part of the sequence of the target polynucleotide, all or part of the 5' and/or 3' untranslated region of the target polynucleotide, all or part of the coding sequence of the target polynucleotide, or all or part of both the coding sequence and the untranslated regions of the target polynucleotide.

Typically, a sense suppression element has substantial sequence identity to the target polynucleotide, typically greater than about 65% sequence identity, greater than about 85% sequence identity, about 90%, 91%, 92%, 93%, 94%, 95%, 96%, 97%, 98% or 99% sequence identity. See, U.S. Pat. Nos. 5,283,184 and 5,034,323; herein incorporated by reference. The sense suppression element can be any length so long as it allows for the suppression of the targeted sequence. The sense suppression element can be, for example, 15, 16, 17, 18 19, 20, 22, 25, 30, 50, 100, 150, 200, 250, 300, 350, 400, 450, 500, 600, 700, 900, 1000, 1100, 1200, 1300 nucleotides or longer of the target polynucleotides set forth in any of SEQ ID NOS: 6-12, 18-40. In other embodiments, the sense suppression element can be, for example, about 15-25, 25-100, 100-150, 150-200, 200-250, 250-300, 300-350, 350-400, 450-500, 500-550, 550-600, 600-650, 650-700, 700-750, 750-800, 800-850, 850-900, 900-950, 950-1000, 1000-1050, 1050-1100, 1100-1200, 1200-1300, 1300-1400, 1400-1500, 1500-1600, 1600-1700, 1700-1800 nucleotides or longer of the target polynucleotides set forth in any of SEQ ID NOS: 6-12, 18-40.

b. Antisense Suppression Elements

As used herein, an "antisense suppression element" comprises a polynucleotide which is designed to express an RNA molecule complementary to all or part of a target messenger RNA. Expression of the antisense RNA suppression element reduces or eliminates the level of the target polynucleotide. The polynucleotide for use in antisense suppression may correspond to all or part of the complement of the sequence encoding the target polynucleotide, all or part of the complement of the 5' and/or 3' untranslated region of the target polynucleotide, all or part of the complement of the coding sequence of the target polynucleotide, or all or part of the complement of both the coding sequence and the untranslated regions of the target polynucleotide. In addition, the antisense suppression element may be fully complementary (i.e., 100% identical to the complement of the target sequence) or partially complementary (i.e., less than 100% identical to the complement of the target sequence) to the target polynucleotide. In specific embodiments, the antisense suppression element comprises at least 85%, 90%, 91%, 92%, 93%, 94%, 95%, 96%, 97%, 98%, or 99% sequence complementarity to the target polynucleotide. Antisense suppression may be used to inhibit the expression of multiple proteins in the same plant. See, for example, U.S. Pat. No. 5,942,657. Furthermore, the antisense suppression element can be complementary to a portion of the target polynucleotide. Generally, sequences of at least 15, 20, 22, 25, 50, 100, 200, 300, 400, 450 nucleotides or greater of the sequence set forth in any of SEQ ID NOS: 6-12, 18-40 may be used. Methods for using antisense suppression to inhibit the expression of endogenous genes in plants are described, for example, in Liu et al (2002) *Plant Physiol.* 129:1732-1743 and U.S. Pat. Nos. 5,759,829 and 5,942,657, each of which is herein incorporated by reference.

c. Double Stranded RNA Suppression Element

A "double stranded RNA silencing element" or "dsRNA" comprises at least one transcript that is capable of forming a dsRNA either before or after ingestion by a pest. Thus, a "dsRNA silencing element" includes a dsRNA, a transcript or polyribonucleotide capable of forming a dsRNA or more than one transcript or polyribonucleotide capable of forming a dsRNA. "Double stranded RNA" or "dsRNA" refers to a polyribonucleotide structure formed either by a single self-complementary RNA molecule or a polyribonucleotide structure formed by the expression of least two distinct RNA strands. The dsRNA molecule(s) employed in the methods and compositions of the invention mediate the reduction of expression of a target sequence, for example, by mediating RNA interference ("RNAi") or gene silencing in a sequence-specific manner. In the context of the present invention, the dsRNA is capable of reducing or eliminating the level of expression of a target polynucleotide or the polypeptide encoded thereby in a pest.

The dsRNA can reduce or eliminate the expression level of the target sequence by influencing the level of the target RNA transcript, by influencing translation and thereby affecting the level of the encoded polypeptide, or by influencing expression at the pre-transcriptional level (i.e., via the modulation of chromatin structure, methylation pattern, etc., to alter gene expression). See, for example, Verdel et al. (2004) Science 303:672-676; Pal-Bhadra et al. (2004) Science 303:669-672; Allshire (2002) Science 297:1818-1819; Volpe et al. (2002) Science 297:1833-1837; Jenuwein (2002) Science 297:2215-2218; and Hall et al. (2002) Science 297:2232-2237. Methods to assay for functional dsRNA that are capable of reducing or eliminating the level of a sequence of interest are disclosed elsewhere herein. Accordingly, as used herein, the term "dsRNA" is meant to encompass other terms used to describe nucleic acid molecules that are capable of mediating RNA interference or gene silencing, including, for example, short-interfering RNA (siRNA), double-stranded RNA (dsRNA), micro-RNA (miRNA), hairpin RNA, short hairpin RNA (shRNA), post-transcriptional gene silencing RNA (ptgsRNA), and others.

In specific embodiments, at least one strand of the duplex or double-stranded region of the dsRNA shares sufficient sequence identity or sequence complementarity to the target polynucleotide to allow for the dsRNA to reduce the level of expression of the target sequence. As used herein, the strand that is complementary to the target polynucleotide is the "antisense strand" and the strand homologous to the target polynucleotide is the "sense strand."

In another embodiment, the dsRNA comprises a hairpin RNA. A hairpin RNA comprises an RNA molecule that is capable of folding back onto itself to form a double stranded structure. Multiple structures can be employed as hairpin elements. In specific embodiments, the dsRNA suppression element comprises a hairpin element which comprises in the following order, a first segment, a second segment, and a third segment, where the first and the third segment share sufficient complementarity to allow the transcribed RNA to form a double-stranded stem-loop structure.

The "second segment" of the hairpin comprises a "loop" or a "loop region." These terms are used synonymously herein and are to be construed broadly to comprise any nucleotide sequence that confers enough flexibility to allow self-pairing to occur between complementary regions of a polynucleotide (i.e., segments 1 and 3 which form the stem of the hairpin). For example, in some embodiments, the loop region may be substantially single stranded and act as a spacer between the self-complementary regions of the hairpin stem-loop. In some embodiments, the loop region can comprise a random or nonsense nucleotide sequence and thus not share sequence identity to a target polynucleotide. In other embodiments, the loop region comprises a sense or an antisense RNA sequence or fragment thereof that shares identity to a target polynucleotide. See, for example, International Patent Publication No. WO 02/00904, herein incorporated by reference. In specific embodiments, the loop region can be optimized to be as short as possible while still providing enough intramolecular flexibility to allow the formation of the base-paired stem region. Accordingly, the loop sequence is generally less than 1000, 900, 800, 700, 600, 500, 400, 300, 200, 100, 50, 25, 20, 15, 10 nucleotides or less.

The "first" and the "third" segment of the hairpin RNA molecule comprise the base-paired stem of the hairpin structure. The first and the third segments are inverted repeats of one another and share sufficient complementarity to allow the formation of the base-paired stem region. In specific embodiments, the first and the third segments are fully complementary to one another. Alternatively, the first and the third segment may be partially complementary to each other so long as they are capable of hybridizing to one another to form a base-paired stem region. The amount of complementarity between the first and the third segment can be calculated as a percentage of the entire segment. Thus, the first and the third segment of the hairpin RNA generally share at least 50%, 60%, 70%, 80%, 85%, 90%, 91%, 92%, 93%, 94%, 95%, 96%, 97%, 98%, 99%, up to and including 100% complementarity.

The first and the third segment are at least about 1000, 500, 400, 300, 200, 100, 50, 40, 30, 25, 22, 20, 19, 18, 17, 16, 15 or 10 nucleotides in length. In specific embodiments, the length of the first and/or the third segment is about 10-100 nucleotides, about 10 to about 75 nucleotides, about 10 to about 50 nucleotides, about 10 to about 40 nucleotides, about 10 to about 35 nucleotides, about 10 to about 30 nucleotides, about 10 to about 25 nucleotides, about 10 to about 19 nucleotides, about 50 nucleotides to about 100 nucleotides, about 100 nucleotides to about 150 nucleotides, about 150 nucleotides to about 200 nucleotides, about 200 nucleotides to about 250 nucleotides, about 250 nucleotides to about 300 nucleotides, about 300 nucleotides to about 350 nucleotides, about 350 nucleotides to about 400 nucleotides, about 400 nucleotides to about 500 nucleotides, about 600 nucleotides, about 700 nucleotides, about 800 nucleotides, about 900 nucleotides, about 1000 nucleotides, about 1100 nucleotides, about 1200 nucleotides, 1300 nucleotides, 1400 nucleotides, 1500 nucleotides, 1600 nucleotides, 1700 nucleotides, 1800 nucleotides, 1900 nucleotides, 2000 nucleotides or longer. In other embodiments, the length of the first and/or the third segment comprises at least 10-19 nucleotides; 19-35 nucleotides; 30-45 nucleotides; 40-50 nucleotides; 50-100 nucleotides; 100-300 nucleotides; about 500-700 nucleotides; about 700-900 nucleotides; about 900-1100 nucleotides; about 1300-1500 nucleotides; about 1500-1700 nucleotides; about 1700-1900 nucleotides; about 1900-2100 nucleotides; about 2100-2300 nucleotides; or about 2300-2500 nucleotides. See, for example, International Publication No. WO 0200904. In specific embodiments, the first and the third segment comprise at least 19 nucleotides having at least 85% complementary to the first segment. In still other embodiments, the first and the third segments which form the stem-loop structure of the hairpin comprises 3' or 5' overhang regions having unpaired nucleotide residues.

Hairpin molecules or double-stranded RNA molecules of the present invention may have more than one sequence of the present invention or active fragments or variants, or complements thereof, found in the same portion of the RNA molecule. For example, in a chimeric hairpin structure, the first segment of a hairpin molecule comprises two poly- nucleotide sections, each with a different sequence of the present invention. For example, reading from one terminus of the hairpin, the first segment is composed of sequences from two separate genes (A followed by B). This first segment is followed by the second segment, the loop portion of the hairpin. The loop segment is followed by the third segment, where the complementary strands of the sequences in the first segment are found (B* followed by A*) In forming the stem-loop, hairpin structure, the stem contains SeqA-A* at the distal end of the stem and SeqB-B* proximal to the loop region.

In specific embodiments, the sequences used in the first, the second, and/or the third segments comprise domains that are designed to have sufficient sequence identity to a target polynucleotide of interest and thereby have the ability to decrease the level of expression of the target polynucleotide. The specificity of the inhibitory RNA transcripts is therefore generally conferred by these domains of the silencing element. Thus, in some embodiments of the invention, the first, second and/or third segment of the silencing element comprise a domain having at least 10, at least 15, at least 19, at least 20, at least 21, at least 22, at least 23, at least 24, at least 25, at least 30, at least 40, at least 50, at least 100, at least 200, at least 300, at least 500, at least 1000, or more than 1000 nucleotides that share sufficient sequence identity to the target polynucleotide to allow for a decrease in expression levels of the target polynucleotide when expressed in an appropriate cell. In other embodiments, the domain is between about 15 to 50 nucleotides, about 19-35 nucleotides, about 25-50 nucleotides, about 19 to 75 nucleotides, about 40-90 nucleotides, about 15-100 nucleotides, 10-100 nucleotides, about 10 to about 75 nucleotides, about 10 to about 50 nucleotides, about 10 to about 40 nucleotides, about 10 to about 35 nucleotides, about 10 to about 30 nucleotides, about 10 to about 25 nucleotides, about 10 to about 19 nucleotides, about 50 nucleotides to about 100 nucleotides, about 100 nucleotides to about 150 nucleotides, about 150 nucleotides to about 200 nucleotides, about 200 nucleotides to about 250 nucleotides, about 250 nucleotides to about 300 nucleotides, about 300 nucleotides to about 350 nucleotides, about 350 nucleotides to about 400 nucleotides, about 400 nucleotide to about 500 nucleotides or longer. In other embodiments, the length of the first and/or the third segment comprises at least 10-19 nucleotides, 19-35 nucleotides, 30-45 nucleotides, 40-50 nucleotides, 50-100 nucleotides, or about 100-300 nucleotides.

In specific embodiments, the domain of the first, the second, and/or the third segment has 100% sequence identity to the target polynucleotide. In other embodiments, the domain of the first, the second and/or the third segment having homology to the target polypeptide have at least 50%, 60%, 70%, 80%, 85%, 90%, 91%, 92%, 93%, 94%, 95%, 96%, 97%, 98%, 99%, or greater sequence identity to a region of the target polynucleotide. The sequence identity of the domains of the first, the second and/or the third segments to the target polynucleotide need only be sufficient to decrease expression of the target polynucleotide of interest. See, for example, Chuang and Meyerowitz (2000) *Proc. Natl. Acad. Sci. USA* 97:4985-4990; Stoutjesdijk et al. (2002) *Plant Physiol.* 129:1723-1731; Waterhouse and Helliwell (2003) *Nat. Rev. Genet.* 4:29-38; Pandolfini et al. *BMC Biotechnology* 3:7, and U.S. Patent Publication No. 20030175965; each of which is herein incorporated by reference. A transient assay for the efficiency of hpRNA constructs to silence gene expression in vivo has been described by Panstruga et al. (2003) *Mol. Biol. Rep.* 30:135-140, herein incorporated by reference.

The amount of complementarity shared between the first, second, and/or third segment and the target polynucleotide or the amount of complementarity shared between the first segment and the third segment (i.e., the stem of the hairpin structure) may vary depending on the organism in which gene expression is to be controlled. Some organisms or cell types may require exact pairing or 100% identity, while other organisms or cell types may tolerate some mismatching. In some cells, for example, a single nucleotide mismatch in the targeting sequence abrogates the ability to suppress gene expression. In these cells, the suppression cassettes of the invention can be used to target the suppression of mutant genes, for example, oncogenes whose transcripts comprise point mutations and therefore they can be specifically targeted using the methods and compositions of the invention without altering the expression of the remaining wild-type allele.

Any region of the target polynucleotide can be used to design the domain of the silencing element that shares sufficient sequence identity to allow expression of the hairpin transcript to decrease the level of the target polynucleotide. For instance, the domain can be designed to share sequence identity to the 5' untranslated region of the target polynucleotide(s), the 3' untranslated region of the target polynucleotide(s), exonic regions of the target polynucleotide(s), intronic regions of the target polynucleotide(s), and any combination thereof In specific embodiments, a domain of the silencing element shares sufficient homology to at least about 15, 16, 17, 18, 19, 20, 22, 25 or 30 consecutive nucleotides from about nucleotides 1-50, 25-75, 75-125, 50-100, 125-175, 175-225, 100-150, 150-200, 200-250, 225-275, 275-325, 250-300, 325-375, 375-425, 300-350, 350-400, 425-475, 400-450, 475-525, 450-500, 525-575, 575-625, 550-600, 625-675, 675-725, 600-650, 625-675, 675-725, 650-700, 725-825, 825-875, 750-800, 875-925, 925-975, 850-900, 925-975, 975-1025, 950-1000, 1000-1050, 1025-1075, 1075-1125, 1050-1100, 1125-1175, 1100-1200, 1175-1225, 1225-1275, 1200-1300, 1325-1375, 1375-1425, 1300-1400, 1425-1475, 1475-1525, 1400-1500, 1525-1575, 1575-1625, 1625-1675, 1675-1725, 1725-1775, 1775-1825, 1825-1875, 1875-1925, 1925-1975, 1975-2025, 2025-2075, 2075-2125, 2125-2175, 2175-2225, 1500-1600, 1600-1700, 1700-1800, 1800-1900, 1900-2000 of the target sequence. In some instances to optimize the siRNA sequences employed in the hairpin, the synthetic oligodeoxyribonucleotide/RNase H method can be used to determine sites on the target mRNA that are in a conformation that is susceptible to RNA silencing. See, for example, Vickers et al. (2003) J. Biol. Chem 278:7108-7118 and Yang et al. (2002) Proc. Natl. Acad. Sci. USA 99:9442-9447, herein incorporated by reference. These studies indicate that there is a significant correlation between the RNase-H-sensitive sites and sites that promote efficient siRNA-directed mRNA degradation.

The hairpin silencing element may also be designed such that the sense sequence or the antisense sequence do not correspond to a target polynucleotide. In this embodiment, the sense and antisense sequence flank a loop sequence that comprises a nucleotide sequence corresponding to all or part of the target polynucleotide. Thus, it is the loop region that determines the specificity of the RNA interference. See, for example, WO 02/00904, herein incorporated by reference.

In addition, transcriptional gene silencing (TGS) may be accomplished through use of a hairpin suppression element where the inverted repeat of the hairpin shares sequence identity with the promoter region of a target polynucleotide to be silenced. See, for example, Aufsatz et al. (2002) PNAS 99 (Suppl. 4):16499-16506 and Mette et al. (2000) EMBO J 19(19):5194-5201.

d. MicroRNA (miRNA) Silencing Element

In other embodiments, the silencing element can comprise a microRNA (miRNA). "MicroRNAs" or "miRNAs" are regulatory agents comprising about 19 to about 24 ribonucleotides in length, which are highly efficient at inhibiting the expression of target polynucleotides. See, for example Javier et al. (2003) Nature 425: 257-263, herein incorporated by reference. For miRNA interference, the silencing element can be designed to express a dsRNA molecule that forms a partially base-paired structure containing a 19, 20, 21, 22, 23, 24 or 25 nucleotide sequence that is complementary to the target polynucleotide of interest. The miRNA can be synthetically made, or transcribed as a longer RNA which is subsequently cleaved to produce the active miRNA. The miRNA can be an "artificial miRNA" or "amiRNA" which comprises a miRNA sequence that is synthetically designed to silence a target sequence.

When expressing an miRNA, the final (mature) miRNA is present in a duplex in a precursor backbone structure, the two strands being referred to as the miRNA (the strand that will eventually base pair with the target) and miRNA* (star sequence). It has been demonstrated that miRNAs can be transgenically expressed and target genes of interest efficiently silenced (Highly specific gene silencing by artificial microRNAs in *Arabidopsis* Schwab R, Ossowski S, Riester M, Warthmann N, Weigel D. Plant Cell. 2006 May; 18(5): 1121-33. Epub 2006 Mar. 10 & Expression of artificial microRNAs in transgenic *Arabidopsis thaliana* confers virus resistance. Niu Q W, Lin S S, Reyes J L, Chen K C, Wu H W, Yeh S D, Chua N H. Nat Biotechnol. 2006 November; 24(11):1420-8. Epub 2006 Oct. 22. Erratum in: Nat Biotechnol. 2007 February; 25(2):254.)

The silencing element for miRNA interference comprises a miRNA primary sequence. The miRNA primary sequence comprises a DNA sequence having the miRNA and star sequences separated by a loop as well as additional sequences flanking this region that are important for processing. When expressed as an RNA, the structure of the primary miRNA is such as to allow for the formation of a hairpin RNA structure that can be processed into a mature miRNA. In some embodiments, the miRNA backbone comprises a genomic or cDNA miRNA precursor sequence, wherein said sequence comprises a native primary in which a heterologous (artificial) mature miRNA and star sequence are inserted.

As used herein, a "star sequence" is the sequence within a miRNA precursor backbone that is complementary to the miRNA and forms a duplex with the miRNA to form the stem structure of a hairpin RNA. In some embodiments, the star sequence can comprise less than 100% complementarity to the miRNA sequence. Alternatively, the star sequence can comprise at least 99%, 98%, 97%, 96%, 95%, 90%, 85%, 80% or lower sequence complementarity to the miRNA sequence as long as the star sequence has sufficient complementarity to the miRNA sequence to form a double stranded structure. In still further embodiments, the star sequence comprises a sequence having 1, 2, 3, 4, 5 or more mismatches with the miRNA sequence and still has sufficient complementarity to form a double stranded structure with the miRNA sequence resulting in production of miRNA and suppression of the target sequence.

The miRNA precursor backbones can be from any plant. In some embodiments, the miRNA precursor backbone is from a monocot. In other embodiments, the miRNA precursor backbone is from a dicot. In further embodiments, the backbone is from maize or soybean. MicroRNA precursor backbones have been described previously. For example, US20090155910A1 (WO 2009/079532) discloses the following soybean miRNA precursor backbones: 156c, 159, 166b, 168c, 396b and 398b, and US20090155909A1 (WO 2009/079548) discloses the following maize miRNA precursor backbones: 159c, 164h, 168a, 169r, and 396h. Each of these references is incorporated by reference in their entirety.

Thus, the primary miRNA can be altered to allow for efficient insertion of heterologous miRNA and star sequences within the miRNA precursor backbone. In such instances, the miRNA segment and the star segment of the miRNA precursor backbone are replaced with the heterologous miRNA and the heterologous star sequences, designed to target any sequence of interest, using a PCR technique and cloned into an expression construct. It is recognized that there could be alterations to the position at which the artificial miRNA and star sequences are inserted into the backbone. Detailed methods for inserting the miRNA and star sequence into the miRNA precursor backbone are described in, for example, US Patent Applications 20090155909A1 and US20090155910A1, herein incorporated by reference in their entirety.

When designing a miRNA sequence and star sequence, various design choices can be made. See, for example, Schwab R, et al. (2005) *Dev Cell* 8: 517-27. In non-limiting embodiments, the miRNA sequences disclosed herein can have a "U" at the 5'-end, a "C" or "G" at the 19$^{th}$ nucleotide position, and an "A" or "U" at the 10th nucleotide position. In other embodiments, the miRNA design is such that the miRNA have a high free delta-G as calculated using the ZipFold algorithm (Markham, N. R. & Zuker, M. (2005) *Nucleic Acids Res.* 33: W577-W581.) Optionally, a one base pair change can be added within the 5' portion of the miRNA so that the sequence differs from the target sequence by one nucleotide.

The methods and compositions of the invention employ silencing elements that when transcribed "form" a dsRNA molecule. Accordingly, the heterologous polynucleotide being expressed need not form the dsRNA by itself, but can interact with other sequences in the plant cell or in the pest gut after ingestion to allow for the formation of the dsRNA. For example, a chimeric polynucleotide that can selectively silence the target polynucleotide can be generated by expressing a chimeric construct comprising the target sequence for a miRNA or siRNA to a sequence corresponding to all or part of the gene or genes to be silenced. In this embodiment, the dsRNA is "formed" when the target for the miRNA or siRNA interacts with the miRNA present in the cell. The resulting dsRNA can then reduce the level of expression of the gene or genes to be silenced. See, for example, US Application Publication 2007-0130653, entitled "Methods and Compositions for Gene Silencing", herein incorporated by reference. The construct can be designed to have a target for an endogenous miRNA or alternatively, a target for a heterologous and/or synthetic miRNA can be employed in the construct. If a heterologous and/or synthetic miRNA is employed, it can be introduced into the cell on the same nucleotide construct as the chimeric polynucleotide or on a separate construct. As discussed elsewhere herein, any method can be used to introduce the construct comprising the heterologous miRNA.

e. Silencing Elements

A silencing element may comprise a chimeric construction molecule comprising two or more sequences of the present invention. For example, the chimeric construction may be a hairpin or dsRNA as disclosed herein. A chimera may comprise two or more sequences of the present invention. Providing at least two different sequences in a single silencing element may allow for targeting multiple genes using one silencing element and/or for example, one expression cassette. Targeting multiple genes may allow for slowing or reducing the possibility of resistance by the pest, and providing the multiple targeting ability in one expressed molecule may reduce the expression burden of the transformed plant or plant product, or provide topical treatments that are capable of targeting multiple hosts with one application.

IV. Variants and Fragments

By "fragment" is intended a portion of the polynucleotide or a portion of the amino acid sequence and hence protein encoded thereby. Fragments of a polynucleotide may encode protein fragments that retain the biological activity of the native protein. Alternatively, fragments of a polynucleotide that are useful as a silencing element do not need to encode fragment proteins that retain biological activity. Thus, fragments of a nucleotide sequence may range from at least about 10, about 15, about 16, about 17, about 18, about 19, about 20 nucleotides, about 22 nucleotides, about 50 nucleotides, about 75 nucleotides, about 100 nucleotides, 200 nucleotides, 300 nucleotides, 400 nucleotides, 500 nucleotides, 600 nucleotides, 700 nucleotides and up to the full-length polynucleotide employed in the invention. Alternatively, fragments of a nucleotide sequence may range from 1-50, 25-75, 75-125, 50-100, 125-175, 175-225, 100-150, 150-200, 200-250, 225-275, 275-325, 250-300, 325-375, 375-425, 300-350, 350-400, 425-475, 400-450, 475-525, 450-500, 525-575, 575-625, 550-600, 625-675, 675-725, 600-650, 625-675, 675-725, 650-700, 725-825, 825-875, 750-800, 875-925, 925-975, 850-900, 925-975, 975-1025, 950-1000, 1000-1050, 1025-1075, 1075-1125, 1050-1100, 1125-1175, 1100-1200, 1175-1225, 1225-1275, 1200-1300, 1325-1375, 1375-1425, 1300-1400, 1425-1475, 1475-1525, 1400-1500, 1525-1575, 1575-1625, 1625-1675, 1675-1725, 1725-1775, 1775-1825, 1825-1875, 1875-1925, 1925-1975, 1975-2025, 2025-2075, 2075-2125, 2125-2175, 2175-2225, 1500-1600, 1600-1700, 1700-1800, 1800-1900, 1900-2000 of any one of SEQ ID NOS: 6-12, 18-40. Methods to assay for the activity of a desired silencing element are described elsewhere herein.

"Variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. A variant of a polynucleotide that is useful as a silencing element will retain the ability to reduce expression of the target polynucleotide and, in some embodiments, thereby control a pest of interest. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the polypeptides employed in the invention. Variant polynucleotides also include synthetically derived polynucleotides, such as those generated, for example, by using site-directed mutagenesis, but continue to retain the desired activity. Generally, variants of a particular polynucleotide of the invention (i.e., a silencing element) will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Percent sequence identity between any two polypeptides can be calculated using sequence alignment programs and parameters described elsewhere herein. Where any given pair of polynucleotides employed in the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

The following terms are used to describe the sequence relationships between two or more polynucleotides or polypeptides: (a) "reference sequence", (b) "comparison window", (c) "sequence identity", and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Inc., Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

A method is provided for identifying a silencing element from the target polynucleotides set forth in SEQ ID NOS: 6-12, 18-40. Such methods comprise obtaining a candidate fragment of any one or more of SEQ ID NOS: 6-12, 18-40 which is of sufficient length to act as a silencing element and thereby reduce the expression of the target polynucleotide and/or control a desired pest; expressing said candidate polynucleotide fragment in an appropriate expression cassette to produce a candidate silencing element and determining if said candidate polynucleotide fragment has the activity of a silencing element, thereby reducing the expression of the target polynucleotide and/or controlling a desired pest. Methods of identifying such candidate fragments based on the desired pathway for suppression are known. For example, various bioinformatics programs can be employed to identify the region of the target polynucleotides that could be exploited to generate a silencing element. See, for example, Elbahir et al. (2001) *Genes and Development* 15:188-200, Schwartz et al. (2003) *Cell* 115:199-208, Khvorova et al. (2003) *Cell* 115:209-216. See also, siRNA at Whitehead (jura.wi.mit.edu/bioc/siRNAext/) which calculates the binding energies for both sense and antisense siRNAs. See, also genscript.com/ssl-bin/app/rnai?op=known; Block-iT™ RNAi designer from Invitrogen and GenScript siRNA Construct Builder.

V. DNA Constructs

The use of the term "polynucleotide" is not intended to limit the present invention to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

The polynucleotide encoding the silencing element(s) or in specific embodiments employed in the methods and compositions of the invention can be provided in expression cassettes for expression in a plant or organism of interest. It is recognized that multiple silencing elements including multiple identical silencing elements, multiple silencing elements targeting different regions of the target sequence, or multiple silencing elements from different target sequences can be used. In this embodiment, it is recognized that each silencing element can be contained in a single or separate cassette, DNA construct, or vector. As discussed, any means of providing the silencing element is contemplated. A plant or plant cell can be transformed with a single cassette comprising DNA encoding one or more silencing elements or separate cassettes comprising each silencing element can be used to transform a plant or plant cell or host cell. Likewise, a plant transformed with one component can be subsequently transformed with the second component. One or more silencing elements can also be brought together by sexual crossing. That is, a first plant comprising one component is crossed with a second plant comprising the second component. Progeny plants from the cross will comprise both components.

The expression cassette can include 5' and 3' regulatory sequences operably linked to the polynucleotide of the invention. "Operably linked" is intended to mean a functional linkage between two or more elements. For example, an operable linkage between a polynucleotide of the invention and a regulatory sequence (i.e., a promoter) is a functional link that allows for expression of the polynucleotide of the invention. Operably linked elements may be contiguous or non-contiguous. When used to refer to the joining of two protein coding regions, by operably linked is intended that the coding regions are in the same reading frame. The cassette may additionally contain at least one additional polynucleotide to be co-transformed into the organism. Alternatively, the additional polypeptide(s) can be provided on multiple expression cassettes. Expression cassettes can be provided with a plurality of restriction sites and/or recombination sites for insertion of the polynucleotide to be under the transcriptional regulation of the regulatory regions. The expression cassette may additionally contain selectable marker genes.

The expression cassette can include in the 5'-3' direction of transcription, a transcriptional and translational initiation region (i.e., a promoter), a polynucleotide comprising the silencing element employed in the methods and compositions of the invention, and a transcriptional and translational termination region (i.e., termination region) functional in plants. In another embodiment, the double stranded RNA is expressed from a suppression cassette. Such a cassette can comprise two convergent promoters that drive transcription of an operably linked silencing element. "Convergent promoters" refers to promoters that are oriented on either terminus of the operably linked silencing element such that each promoter drives transcription of the silencing element in opposite directions, yielding two transcripts. In such embodiments, the convergent promoters allow for the transcription of the sense and anti-sense strand and thus allow for the formation of a dsRNA.

The regulatory regions (i.e., promoters, transcriptional regulatory regions, and translational termination regions) and/or the polynucleotides employed in the invention may be native/analogous to the host cell or to each other. Alternatively, the regulatory regions and/or the polynucleotide employed in the invention may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence.

The termination region may be native with the transcriptional initiation region, may be native with the operably linked polynucleotide encoding the silencing element, may be native with the plant host, or may be derived from another source (i.e., foreign or heterologous) to the promoter, the polynucleotide comprising silencing element, the plant host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The polynucleotide encoding the silencing element can be combined with constitutive, tissue-preferred, or other promoters for expression in plants.

Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

An inducible promoter, for instance, a pathogen-inducible promoter could also be employed. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Additionally, as pathogens find entry into plants through wounds or insect damage, a wound-inducible promoter may be used in the constructions of the invention. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2):141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced expression within a particular plant tissue. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen Genet.* 254 (3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2): 343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179.

In one embodiment of this invention the plant-expressed promoter is a vascular-specific promoter such as a phloem-specific promoter. A "vascular-specific" promoter, as used herein, is a promoter which is at least expressed in vascular cells, or a promoter which is preferentially expressed in vascular cells. Expression of a vascular-specific promoter need not be exclusively in vascular cells, expression in other cell types or tissues is possible. A "phloem-specific promoter" as used herein, is a plant-expressible promoter which is at least expressed in phloem cells, or a promoter which is preferentially expressed in phloem cells.

Expression of a phloem-specific promoter need not be exclusively in phloem cells, expression in other cell types or tissues, e.g., xylem tissue, is possible. In one embodiment of this invention, a phloem-specific promoter is a plant-expressible promoter at least expressed in phloem cells, wherein the expression in non-phloem cells is more limited (or absent) compared to the expression in phloem cells. Examples of suitable vascular-specific or phloem-specific promoters in accordance with this invention include but are not limited to the promoters selected from the group consisting of: the SCSV3, SCSV4, SCSV5, and SCSV7 promoters (Schunmann et al. (2003) *Plant Functional Biology* 30:453-60; the rolC gene promoter of *Agrobacterium rhizogenes* (Kiyokawa et al. (1994) *Plant Physiology* 104:801-02; Pandolfini et al. (2003) *BioMedCentral (BMC) Biotechnol-* ogy 3:7; Graham et al. (1997) *Plant Mol. Biol.* 33:729-35; Guivarc'h et al. (1996); Almon et al. (1997) *Plant Physiol.* 115:1599-607; the rolA gene promoter of *Agrobacterium rhizogenes* (Dehio et al. (1993) *Plant Mol. Biol.* 23:1199-210); the promoter of the *Agrobacterium tumefaciens* T-DNA gene 5 (Korber et al. (1991) *EMBO J.* 10:3983-91); the rice sucrose synthase RSs1 gene promoter (Shi et al. (1994) *J. Exp. Bot.* 45:623-31); the CoYMV or *Commelina* yellow mottle badnavirus promoter (Medberry et al. (1992) *Plant Cell* 4:185-92; Zhou et al. (1998) *Chin. J. Biotechnol.* 14:9-16); the CFDV or coconut foliar decay virus promoter (Rohde et al. (1994) *Plant Mol. Biol.* 27:623-28; Hehn and Rhode (1998) *J. Gen. Virol.* 79:1495-99); the RTBV or rice tungro bacilliform virus promoter (Yin and Beachy (1995) *Plant J.* 7:969-80; Yin et al. (1997) *Plant J.* 12:1179-80); the pea glutamin synthase GS3A gene (Edwards et al. (1990) *Proc. Natl. Acad. Sci. USA* 87:3459-63; Brears et al. (1991) *Plant* 1:235-44); the inv CD111 and inv CD141 promoters of the potato invertase genes (Hedley et al. (2000) *J. Exp. Botany* 51:817-21); the promoter isolated from *Arabidopsis* shown to have phloem-specific expression in tobacco by Kertbundit et al. (1991) *Proc. Natl. Acad. Sci. USA* 88:5212-16); the VAHOX1 promoter region (Tornero et al. (1996) *Plant J.* 9:639-48); the pea cell wall invertase gene promoter (Zhang et al. (1996) *Plant Physiol.* 112:1111-17); the promoter of the endogenous cotton protein related to chitinase of US published patent application 20030106097, an acid invertase gene promoter from carrot (Ramloch-Lorenz et al. (1993) *The Plant J.* 4:545-54); the promoter of the sulfate transporter geneSultrl; 3 (Yoshimoto et al. (2003) *Plant Physiol.* 131:1511-17); a promoter of a sucrose synthase gene (Nolte and Koch (1993) *Plant Physiol.* 101:899-905); and the promoter of a tobacco sucrose transporter gene (Kuhn et al. (1997) *Science* 275-1298-1300).

Possible promoters also include the Black Cherry promoter for Prunasin Hydrolase (PH DL1.4 PRO) (U.S. Pat. No. 6,797,859), thioredoxin H promoter from cucumber and rice (Fukuda A et al. (2005). *Plant Cell Physiol.* 46(11): 1779-86), Rice (RSs1) (Shi, T. Wang et al. (1994). *J. Exp. Bot.* 45(274): 623-631) and maize sucrose synthase-1 promoters (Yang., N-S. et al. (1990) *PNAS* 87:4144-4148), PP2 promoter from pumpkin (Guo, H. et al. (2004) *Transgenic Research* 13:559-566), At SUC2 promoter (Truernit, E. et al. (1995) *Planta* 196(3):564-70, At SAM1 (S-adenosylmethionine synthetase) (Mijnsbrugge K V. et al. (1996) *Planr. Cell. Physiol.* 37(8): 1108-1115), and the Rice tungro bacilliform virus (RTBV) promoter (Bhattacharyya-Pakrasi et al. (1993) *Plant J.* 4(1):71-79).

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Sci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference. The above list of selectable marker genes is not meant to be limiting. Any selectable marker gene can be used in the present invention.

VI. Compositions Comprising Silencing Elements

One or more of the polynucleotides comprising a silencing element can be provided as an external composition such as a spray or powder to the plant, plant part, seed, a pest, or an area of cultivation. In another example, a plant is transformed with a DNA construct or expression cassette for expression of at least one silencing element. In either composition, the silencing element, when ingested by an insect, can reduce the level of a target pest sequence and thereby control the pest (i.e., a Pentatomidae plant pest including a *N. viridula, Acrosternum hilare, Piezodorus guildini*, and/or *Halymorpha halys*). It is recognized that the composition can comprise a cell (such as plant cell or a bacterial cell), in which a polynucleotide encoding one or more silencing elements is stably incorporated into the genome and operably linked to promoters active in the cell. Compositions comprising a mixture of cells, some cells expressing at least one silencing element are also encompassed. In other embodiments, compositions comprising the silencing elements are not contained in a cell. In such embodiments, the composition can be applied to an area inhabited by a pest. In one embodiment, the composition is applied externally to a plant (i.e., by spraying a field or area of cultivation) to protect the plant from the pest. Methods of applying nucleotides in such a manner are known to those skilled in the art.

The composition of the invention can further be formulated as bait. In this embodiment, the compositions comprise a food substance or an attractant which enhances the attractiveness of the composition to the pest.

The composition comprising the silencing element can be formulated in an agriculturally suitable and/or environmentally acceptable carrier. Such carriers can be any material that the animal, plant or environment to be treated can tolerate. Furthermore, the carrier must be such that the composition remains effective at controlling a pest. Examples of such carriers include water, saline, Ringer's solution, dextrose or other sugar solutions, Hank's solution, and other aqueous physiologically balanced salt solutions, phosphate buffer, bicarbonate buffer and Tris buffer. In addition, the composition may include compounds that increase the half-life of a composition.

It is recognized that the polynucleotides comprising sequences encoding the silencing element(s) can be used to transform organisms to provide for host organism production of these components, and subsequent application of the host organism to the environment of the target pest(s). Such host organisms include baculoviruses, bacteria, and the like. In this manner, the combination of polynucleotides encoding the silencing element(s) may be introduced via a suitable vector into a microbial host, and said host applied to the environment, or to plants or animals.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be stably incorporated into the genome of the cell (e.g., chromosome, plasmid, plastid, or mitochondrial DNA), converted into an autonomous replicon, or transiently expressed (e.g., transfected mRNA).

Microbial hosts that are known to occupy the "phytosphere" (phylloplane, phyllosphere, rhizosphere, and/or rhizoplana) of one or more crops of interest may be selected. These microorganisms are selected so as to be capable of successfully competing in the particular environment with the wild-type microorganisms, provide for stable maintenance and expression of the sequences encoding the silencing element, and desirably, provide for improved protection of the components from environmental degradation and inactivation.

Such microorganisms include bacteria, algae, and fungi. Of particular interest are microorganisms such as bacteria, e.g., *Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc,* and *Alcaligenes,* fungi, particularly yeast, e.g., *Saccharomyces, Cryptococcus, Kluyveromyces, Sporobolomyces, Rhodotorula,* and *Aureobasidium*. Of particular interest are such phytosphere bacterial species as *Pseudomonas syringae, Pseudomonas fluorescens, Serratia marcescens, Acetobacter xylinum, Agrobacteria, Rhodopseudomonas spheroides, Xanthomonas campestris, Rhizobium melioti, Alcaligenes entrophus, Clavibacter xyli* and *Azotobacter vinlandir,* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces rosues, S. odorus, Kluyveromyces veronae,* and *Aureobasidium pollulans*. Of particular interest are the pigmented microorganisms.

A number of ways are available for introducing the polynucleotide comprising the silencing element(s) into the microbial host under conditions that allow for stable maintenance and expression of such nucleotide encoding sequences. For example, expression cassettes can be constructed which include the nucleotide constructs of interest operably linked with the transcriptional and translational regulatory signals for expression of the nucleotide constructs, and a nucleotide sequence homologous with a sequence in the host organism, whereby integration will occur, and/or a replication system that is functional in the host, whereby integration or stable maintenance will occur.

Transcriptional and translational regulatory signals include, but are not limited to, promoters, transcriptional initiation start sites, operators, activators, enhancers, other regulatory elements, ribosomal binding sites, an initiation codon, termination signals, and the like. See, for example, U.S. Pat. Nos. 5,039,523 and 4,853,331; EPO 0480762A2; Sambrook et al. (2000); *Molecular Cloning: A Laboratory Manual* (3$^{rd}$ ed.; Cold Spring Harbor Laboratory Press, Plainview, N.Y.); Davis et al. (1980) *Advanced Bacterial Genetics* (Cold Spring Harbor Laboratory, Cold Spring Harbor, N.Y.); and the references cited therein.

Suitable host cells include the prokaryotes and the lower eukaryotes, such as fungi. Illustrative prokaryotes, both Gram-negative and Gram-positive, include Enterobacteriaceae, such as *Escherichia, Erwinia, Shigella, Salmonella,* and *Proteus; Bacillaceae; Rhizobiceae,* such as *Rhizobium; Spirillaceae,* such as photobacterium, *Zymomonas, Serratia, Aeromonas, Vibrio, Desulfovibrio, Spirillum; Lactobacillaceae; Pseudomonadaceae,* such as *Pseudomonas* and *Acetobacter; Azotobacteraceae* and *Nitrobacteraceae*. Among eukaryotes are fungi, such as *Phycomycetes* and *Ascomycetes,* which includes yeast, such as *Saccharomyces* and *Schizosaccharomyces;* and *Basidiomycetes* yeast, such as *Rhodotorula, Aureobasidium, Sporobolomyces,* and the like.

Characteristics of particular interest in selecting a host cell for purposes of the invention include ease of introducing the coding sequence into the host, availability of expression systems, efficiency of expression, stability in the host, and the presence of auxiliary genetic capabilities. Characteristics of interest for use as a pesticide microcapsule include protective qualities, such as thick cell walls, pigmentation, and intracellular packaging or formation of inclusion bodies; leaf affinity; lack of mammalian toxicity; attractiveness to pests for ingestion; and the like. Other considerations include ease of formulation and handling, economics, storage stability, and the like.

Host organisms of particular interest include yeast, such as *Rhodotorula* spp., *Aureobasidium* spp., *Saccharomyces* spp., and *Sporobolomyces* spp., phylloplane organisms such as *Pseudomonas* spp., *Erwinia* spp., and *Flavobacterium* spp., and other such organisms, including *Pseudomonas aeruginosa, Pseudomonas fluorescens, Saccharomyces cerevisiae, Bacillus thuringiensis, Escherichia coli, Bacillus subtilis,* and the like.

The sequences encoding the silencing elements encompassed by the invention can be introduced into microorganisms that multiply on plants (epiphytes) to deliver these components to potential target pests. Epiphytes, for example, can be gram-positive or gram-negative bacteria.

The silencing element can be fermented in a bacterial host and the resulting bacteria processed and used as a microbial spray in the same manner that *Bacillus thuringiensis* strains have been used as insecticidal sprays. Any suitable microorganism can be used for this purpose. By way of example, *Pseudomonas* has been used to express *Bacillus thuringiensis* endotoxins as encapsulated proteins and the resulting cells processed and sprayed as an insecticide Gaertner et al. (1993), in *Advanced Engineered Pesticides*, ed. L. Kim (Marcel Decker, Inc.).

Alternatively, the components of the invention are produced by introducing heterologous genes into a cellular host. Expression of the heterologous sequences results, directly or indirectly, in the intracellular production of the silencing element. These compositions may then be formulated in accordance with conventional techniques for application to the environment hosting a target pest, e.g., soil, water, and foliage of plants. See, for example, EPA 0192319, and the references cited therein.

In the present invention, a transformed microorganism can be formulated with an acceptable carrier into separate or combined compositions that are, for example, a suspension, a solution, an emulsion, a dusting powder, a dispersible granule, a wettable powder, and an emulsifiable concentrate, an aerosol, an impregnated granule, an adjuvant, a coatable paste, and also encapsulations in, for example, polymer substances.

Such compositions disclosed above may be obtained by the addition of a surface-active agent, an inert carrier, a preservative, a humectant, a feeding stimulant, an attractant, an encapsulating agent, a binder, an emulsifier, a dye, a UV protectant, a buffer, a flow agent or fertilizers, micronutrient donors, or other preparations that influence plant growth. One or more agrochemicals including, but not limited to, herbicides, insecticides, fungicides, bactericides, nematicides, molluscicides, acaracides, plant growth regulators, harvest aids, and fertilizers, can be combined with carriers, surfactants or adjuvants customarily employed in the art of formulation or other components to facilitate product handling and application for particular target pests. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the present invention (i.e., at least one silencing element) are normally applied in the form of compositions and can be applied to the crop area, plant, or seed to be treated. For example, the compositions may be applied to grain in preparation for or during storage in a grain bin or silo, etc. The compositions may be applied simultaneously or in succession with other compounds. Methods of applying an active ingredient or a composition that contains at least one silencing element include, but are not limited to, foliar application, seed coating, and soil application. The number of applications and the rate of application depend on the intensity of infestation by the corresponding pest.

Suitable surface-active agents include, but are not limited to, anionic compounds such as a carboxylate of, for example, a metal; carboxylate of a long chain fatty acid; an N-acylsarcosinate; mono- or di-esters of phosphoric acid with fatty alcohol ethoxylates or salts of such esters; fatty alcohol sulfates such as sodium dodecyl sulfate, sodium octadecyl sulfate, or sodium cetyl sulfate; ethoxylated fatty alcohol sulfates; ethoxylated alkylphenol sulfates; lignin sulfonates; petroleum sulfonates; alkyl aryl sulfonates such as alkyl-benzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitan fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include, but are not limited to, inorganic minerals such as kaolin, phyllosilicates, carbonates, sulfates, phosphates, or botanical materials such as cork, powdered corncobs, peanut hulls, rice hulls, and walnut shells.

The compositions comprising the silencing element(s) can be in a suitable form for direct application or as a concentrate of primary composition that requires dilution with a suitable quantity of water or other dilutant before application.

The compositions (including the transformed microorganisms) can be applied to the environment of an insect pest (such as a Pentatomidae plant pest such as, for example, a *N. viridula, Acrosternum hilare, Piezodorus guildini*, and/or *Halymorpha halys* plant pest) by, for example, spraying, atomizing, dusting, scattering, coating or pouring, introducing into or on the soil, introducing into irrigation water, by seed treatment or general application or dusting at the time when the pest has begun to appear or before the appearance of pests as a protective measure. For example, the composition(s) and/or transformed microorganism(s) may be mixed with grain to protect the grain during storage. It is generally important to obtain good control of pests in the early stages of plant growth, as this is the time when the plant can be most severely damaged. The compositions can conveniently contain another insecticide if this is thought necessary. In an embodiment of the invention, the composition(s) is applied directly to the soil, at a time of planting, in granular form of a composition of a carrier and dead cells of a *Bacillus* strain or transformed microorganism of the invention. Another embodiment is a granular form of a composition comprising an agrochemical such as, for example, a herbicide, an insecticide, a fertilizer, in an inert carrier, and dead cells of a *Bacillus* strain or transformed microorganism of the invention.

VII. Plants, Plant Parts, and Methods of Introducing Sequences into Plants

In one embodiment, the methods of the invention involve introducing a polynucleotide into a plant. "Introducing" is intended to mean presenting to the plant the polynucleotide in such a manner that the sequence gains access to the interior of a cell of the plant. The methods of the invention do not depend on a particular method for introducing a sequence into a plant, only that the polynucleotides or polypeptides gain access to the interior of at least one cell of the plant. Methods for introducing polynucleotides into plants are known in the art including, but not limited to, stable transformation methods, transient transformation methods, and virus-mediated methods.

"Stable transformation" is intended to mean that the nucleotide construct introduced into a plant integrates into the genome of the plant and is capable of being inherited by the progeny thereof "Transient transformation" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. No. 5,563,055 and U.S. Pat. No. 5,981,840), direct gene transfer (Paszkowski et al. (1984) *EMBO J.* 3:2717-2722), and ballistic particle acceleration (see, for example, U.S. Pat. No. 4,945,050; U.S. Pat. No. 5,879,918; U.S. Pat. No. 5,886,244; and, 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In specific embodiments, the silencing element sequences of the invention can be provided to a plant using a variety of transient transformation methods. Such transient transformation methods include, but are not limited to, the introduction of the protein or variants and fragments thereof directly into the plant or the introduction of the transcript into the plant. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference. Alternatively, polynucleotides can be transiently transformed into the plant using techniques known in the art. Such techniques include viral vector systems and the precipitation of the polynucleotide in a manner that precludes subsequent release of the DNA. Thus, the transcription from the particle-bound DNA can occur, but the frequency with which it is released to become integrated into the genome is greatly reduced. Such methods include the use of particles coated with polyethyleneimine (PEI; Sigma-Aldrich Corp., St. Louis, Mo., Catalog No. P3143).

In other embodiments, the polynucleotide of the invention may be introduced into plants by contacting plants with a virus or viral nucleic acids. Generally, such methods involve incorporating a nucleotide construct of the invention within a viral DNA or RNA molecule. Further, it is recognized that promoters of the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316, 931, and Porta et al. (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the invention can be contained in a transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide of the invention, for example, an expression cassette of the invention, stably incorporated into their genome.

As used herein, the term plant also includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

The present invention may be used for transformation of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatas*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean plants and sugarcane plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

VIII. Methods of Use

Methods of the invention comprise methods for controlling a pest (i.e., a Pentatomidae plant pest, such as, *N. viridula, Acrosternum hilare, Piezodorus guildini*, and/or *Halymorpha halys* plant pest). In one embodiment, the method comprises feeding to a pest a composition comprising a silencing element of the invention, wherein said silencing element, when ingested by a pest (i.e., a Pentatomidae plant pest including *N. viridula, Acrosternum hilare, Piezodorus guildini*, and/or *Halymorpha halys*), reduces the level of a target polynucleotide of the pest and thereby controls the pest. The pest can be fed the silencing element(s) in a variety of ways. For example, in one embodiment, a polynucleotide comprising the silencing element(s) is introduced into a plant. As the Pentatomidae plant pest such as, for example, a *N. viridula, Acrosternum hilare, Piezodorus guildini*, and/or *Halymorpha halys* plant pest feeds on the plant or part thereof expressing these sequences, the silencing element is delivered to the pest. When the silencing element is delivered to the plant in this manner, it is recognized that the silencing element can be expressed constitutively or alternatively, it may be produced in a stage-specific manner by employing the various inducible or tissue-preferred or developmentally regulated promoters that are discussed elsewhere herein. In specific embodiments, the silencing element(s) is expressed in the roots, stalk or stem, leaf including pedicel, xylem and phloem, fruit or reproductive tissue, silk, flowers and all parts therein or any combination thereof.

In another method, a composition comprising at least one silencing element of the invention is applied to a plant. In such embodiments, the silencing element can be formulated in an agronomically suitable and/or environmentally acceptable carrier, which is preferably, suitable for dispersal in fields. In addition, the carrier can also include compounds that increase the half-life of the composition. In specific embodiments, the composition comprising the silencing element is formulated in such a manner such that it persists in the environment for a length of time sufficient to allow it to be delivered to a pest. In such embodiments, the composition can be applied to an area inhabited by a pest. In one embodiment, the composition is applied externally to a plant (i.e., by spraying a field) to protect the plant from pests.

In certain embodiments, the constructs of the present invention can be stacked with any combination of polynucleotide sequences of interest in order to create plants with a desired trait. A trait, as used herein, refers to the phenotype derived from a particular sequence or groups of sequences. For example, the polynucleotides of the present invention may be stacked with any other polynucleotides encoding polypeptides having pesticidal and/or insecticidal activity, such as other *Bacillus thuringiensis* toxic proteins (described in U.S. Pat. Nos. 5,366,892; 5,747,450; 5,737,514; 5,723,756; 5,593,881; and Geiser et al. (1986) Gene 48:109), lectins (Van Damme et al. (1994) *Plant Mol. Biol.* 24:825, pentin (described in U.S. Pat. No. 5,981,722), and the like. The combinations generated can also include multiple copies of any one of the polynucleotides of interest. The polynucleotides of the present invention can also be stacked with any other gene or combination of genes to produce plants with a variety of desired trait combinations including, but not limited to, traits desirable for animal feed such as high oil genes (e.g., U.S. Pat. No. 6,232,529); balanced amino acids (e.g., hordothionins (U.S. Pat. Nos. 5,990,389; 5,885,801; 5,885,802; and 5,703,409); barley high lysine (Williamson et al. (1987) *Eur. J. Biochem.* 165:99-106; and WO 98/20122) and high methionine proteins (Pedersen et al. (1986) *J Biol. Chem.* 261:6279; Kirihara et al. (1988) Gene 71:359; and Musumura et al. (1989) *Plant Mol. Biol.* 12:123)); increased digestibility (e.g., modified storage proteins (U.S. Pat. No. 6,858,778; and thioredoxins (U.S. Pat. No. 7,009,087; the disclosures of which are herein incorporated by reference.

The polynucleotides of the present invention can also be stacked with traits desirable for disease or herbicide resistance (e.g., fumonisin detoxification genes (U.S. Pat. No. 5,792,931); avirulence and disease resistance genes (Jones et al. (1994) *Science* 266:789; Martin et al. (1993) *Science* 262:1432; Mindrinos et al. (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)); the disclosures of which are herein incorporated by reference. One could also combine the polynucleotides of the present invention with polynucleotides providing agronomic traits such as male sterility (e.g., see U.S. Pat. No. 5,583,210), stalk strength, flowering time, or transformation technology traits such as cell cycle regulation or gene targeting (e.g., WO 99/61619, WO 00/17364, and WO 99/25821); the disclosures of which are herein incorporated by reference.

These stacked combinations can be created by any method including, but not limited to, cross-breeding plants by any conventional or TopCross methodology, or genetic transformation. If the sequences are stacked by genetically transforming the plants (i.e., molecular stacks), the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

The following examples are offered by way of illustration and not by way of limitation.

EXPERIMENTAL

Example 1: Selection of DNAs

DNAs were selected by two different methods. cDNA libraries were constructed using the SMART cDNA Synthesis Kit (Clontech) from mRNA isolated from second instar southern green stinkbug (*Nezara viridula* (Linnaeus)) or mRNA isolated from the head of second and third instar southern green stinkbugs. Select clones were sequenced and subject to BLAST analysis to create an expressed sequence tag (EST) library. The library was BLAST queried with sequences of interest and southern green stinkbug homologs were identified.

Additionally, a transcriptome of second instar southern green stinkbug was created using Illumina sequencing. Sequences were assembled using Oases (Schulz et al. 2012) and annotated using a proprietary functional annotation pipeline. The transcriptome was BLAST queried with sequences of interest and southern green stinkbug homologs were identified. DNAs were synthesized using RT-PCR. In brief, mRNA from second instar southern green stinkbug was reverse transcribed using the SuperScript® III First-Strand Synthesis System (Invitrogen; catalog #18080-051) using random primers. Sequences of interest were PCR amplified using gene specific primers and ReadyMix Taq PCR Reaction Mix (Sigma-Aldrich Corp., St. Louis, Mo., Catalog No. P4600). The resulting DNA was analyzed on TAE agarose gels and cloned into pCR2.1 (Invitrogen). The resulting clones were sequenced and sequence verified clones were used to produce double stranded RNA.

Example 2: Production of Double Stranded RNA

Either EST clones or clones derived from RT-PCR and cloned into pCR2.1 were used as template for PCR. Sequences flanking the insert were fused with the T7 promoter sequence (TAATACGACTCACTATAGGG, SEQ ID 1) and used to generate primers (Table 1) to PCR amplify DNA. This PCR amplified DNA was used to synthesize double stranded RNA (dsRNA) using the MEGAscript® kit (Ambion, Catalog No. AM1334) following the manufacturer's protocol. Products of PCR as well as dsRNA synthesis were run on 1% agarose gel to verify amplification. With the EST clones, after the initial screening, fragments of the EST clones were amplified using gene specific primers fused with the T7 promoter sequence.

TABLE 1

| EST PRIMER 1 | TAATACGACTCACTATAGGGATGCCCGGGAA TTCGGCCATTACG | SEQ ID 2 |
|---|---|---|
| EST PRIMER 2 | TAATACGACTCACTATAGGGCGCGCCAAACG AATGGTCTAGAAAGC | SEQ ID 3 |
| pCR2.1 Primer 1 | TAATACGACTCACTATAGGGCTAGTAACGGC CGCCAGTGTGCTG | SEQ ID 4 |
| pCR2.1 Primer 1 | TAATACGACTCACTATAGGGGGCCGCCAGTG TGATGGATATCTG | SEQ ID 5 |

Example 3: Selected Clones

The following clones (Table 2) were selected for use in the bioassay.

TABLE 2

| SEQ ID NO | Clone name | length bp | DESCRIPTION | Corresponding full-length DNA |
|---|---|---|---|---|
| SEQ ID NO 21 | ta01222.002 Fragment 1 | 362 | WD domain, G-beta repeat protein | ta01222.002_nezvi SEQ ID 6 |
| SEQ ID NO 22 | ta01222.002 Fragment 2 | 369 | WD domain, G-beta repeat protein | ta01222.002_nezvi SEQ ID 6 |
| SEQ ID NO 23 | ta01222.002 Fragment 3 | 374 | WD domain, G-beta repeat protein | ta01222.002_nezvi SEQ ID 6 |
| SEQ ID NO 24 | ta02948.001 Fragment 1 | 355 | Coatomer protein complex, subunit beta 1, | ta02948.001_nezvi SEQ ID 7 |
| SEQ ID NO 25 | ta02948.001 Fragment 2 | 382 | Coatomer protein complex, subunit beta 1, | ta02948.001_nezvi SEQ ID 7 |

TABLE 2-continued

| SEQ ID NO | Clone name | length bp | DESCRIPTION | Corresponding full-length DNA |
|---|---|---|---|---|
| SEQ ID NO 26 | ta02948.001 Fragment 3 | 376 | Coatomer protein complex, subunit beta 1, | ta02948.001_nezvi SEQ ID 7 |
| SEQ ID NO 27 | ta00781.001 Fragment 1 | 340 | Coatomer, gamma subunit, | ta00781.001_nezvi SEQ ID 8 |
| SEQ ID NO 28 | ta00781.001 Fragment 2 | 383 | Coatomer, gamma subunit, | ta00781.001_nezvi SEQ ID 8 |
| SEQ ID NO 29 | ta00781.001 Fragment 3 | 388 | Coatomer, gamma subunit, | ta00781.001_nezvi SEQ ID 8 |
| SEQ ID NO 30 | nezvi_22408.WL.1 Fragment 3 | 412 | Ryanodine receptor | nezvi_22408.WL.1 SEQ ID 9 |
| SEQ ID NO 31 | nezvi_22408.WL.1 Fragment 6 | 342 | Ryanodine receptor | nezvi_22408.WL.1 SEQ ID 9 |
| SEQ ID NO 32 | nezvi_22408.WL.1 Fragment 7 | 432 | Ryanodine receptor | nezvi_22408.WL.1 SEQ ID 9 |
| SEQ ID NO 33 | nezvi_22408.WL.1 Fragment 9 | 367 | Ryanodine receptor | nezvi_22408.WL.1 SEQ ID 9 |
| SEQ ID NO 34 | nezvi_22408.WL.1 Fragment 14 | 396 | Ryanodine receptor | nezvi_22408.WL.1 SEQ ID 9 |
| SEQ ID NO 10 | inv2c.pk011.b22.f | 965 | 26S proteasome non-ATPase regulatory subunit 7 | inv2c.pk011.b22.f SEQ ID 10 |
| SEQ ID NO 35 | inv2c.pk011.b22.f Fragment 1 | 557 | 26S proteasome non-ATPase regulatory subunit 7 | inv2c.pk011.b22.f SEQ ID 10 |
| SEQ ID NO 36 | inv2c.pk011.b22f Fragment 2 | 530 | 26S proteasome non-ATPase regulatory subunit 7 | inv2c.pk011.b22.f SEQ ID 10 |
| SEQ ID NO 11 | inv2c.pk020.119.f | 924 | Proteasome subunit alpha type-2 | inv2c.pk020.119.f SEQ ID 11 |
| SEQ ID NO 37 | inv2c.pk020.119.f Fragment 1 | 544 | Proteasome subunit alpha type-2 | inv2c.pk020.119.f SEQ ID 11 |
| SEQ ID NO 38 | inv2c.pk020.119.f Fragment 2 | 587 | Proteasome subunit alpha type-2 | inv2c.pk020.119.f SEQ ID 11 |
| SEQ ID NO 12 | inv3c.pk002.i8.f | 946 | 26S protease regulatory subunit 8-like | inv3c.pk002.i8.f SEQ ID 12 |
| SEQ ID NO 39 | inv3c.pk002.i8.f Fragment 1 | 550 | 26S protease regulatory subunit 8-like | inv3c.pk002.i8.f SEQ ID 12 |
| SEQ ID NO 40 | inv3c.pk002.i8.f Fragment 2 | 580 | 26S protease regulatory subunit 8-like | inv3c.pk002.i8.f SEQ ID 12 |

Example 4: Stinkbug Collection and Bioassay

Southern green stinkbug eggs were collected from a laboratory maintained colony and kept in an incubator at 27° C. with 65% relative humidity. After hatching, the insects were allowed to feed on green beans with or without the addition of green peas. Thereafter freshly molted second instar stinkbugs were transferred onto a modified artificial *Lygus* diet (Bioserve; *Lygus Hesperus* diet, catalog # F9644B) supplemented either with dsRNA or water (as control). Five second instar stinkbugs per bioassay were fed with 200 ppm dsRNA supplemented in the artificial diet. The diet with dsRNA or water was changed every two days and the bioassay observations on stunting and/or mortality were taken on day 7. All insects were weighed at the conclusion of the assay.

Example 5: Results of dsRNA Feeding

Five second instars per experiment were either fed upon a diet mixed with select dsRNA or water (control) and each experiment was replicated two to six times. The number of replicates is reported in column four (labeled N) of Table Three. Feeding of select dsRNAs to second instar southern green stinkbug significantly inhibited the growth when compared with controls. At the conclusion of the bioassay (day 7), the control stinkbugs developed into late third instars and weighed on an average 11.3±0.9 mg (group A) or 8.4±0.8 mg (group B). It is understood by those in the field that bioassay data can vary depending upon the time the assays are run which explains the differences in control weight. Insects fed selected dsRNA developed poorly and were still in second instar stage and only developed to 46-66% of the control weight. See Table 3.

TABLE 3

| DNA | SEQ ID NO | Group | % control weight | N |
|---|---|---|---|---|
| ta01222.002 Fragment 1 | 21 | A | 66 | 4 |
| ta01222.002 Fragment 2 | 22 | A | 59 | 4 |
| ta01222.002 Fragment 3 | 23 | A | 51 | 4 |
| ta02948.001 Fragment 1 | 24 | A | 49 | 4 |
| ta02948.001 Fragment 2 | 25 | A | 57 | 4 |
| ta02948.001 Fragment 3 | 26 | A | 63 | 4 |
| ta00781.001 Fragment 1 | 27 | A | 52 | 4 |
| ta00781.001 Fragment 2 | 28 | A | 59 | 4 |
| ta00781.001 Fragment 3 | 29 | A | 58 | 4 |
| nezvi_22408.WL.1 Fragment 7 | 32 | A | 58 | 3 |
| inv2c.pk011.b22.f | 10 | B | 46 | 2 |
| inv2c.pk011.b22.f Fragment 1 | 35 | B | 48 | 2 |
| inv2c.pk011.b22f Fragment 2 | 36 | B | 63 | 6 |
| inv2c.pk020.119.f | 11 | B | 48 | 2 |
| inv2c.pk020.119.f Fragment 1 | 37 | B | 61 | 2 |
| inv2c.pk020.119.f Fragment 2 | 38 | B | 50 | 6 |
| inv3c.pk002.i8.f | 12 | B | 49 | 2 |
| inv3c.pk002.i8.f Fragment 1 | 39 | B | 52 | 2 |
| inv3c.pk002.i8.f Fragment 2 | 40 | B | 55 | 2 |
| nezvi_22408.WL.1 Fragment 3 | 30 | B | 54 | 6 |
| nezvi_22408.WL.1 Fragment 6 | 31 | B | 55 | 6 |
| nezvi_22408.WL.1 Fragment 7 | 32 | B | 47 | 6 |

TABLE 3-continued

| DNA | SEQ ID NO | Group | % control weight | N |
|---|---|---|---|---|
| nezvi_22408.WL.1 Fragment 9 | 33 | B | 57 | 6 |
| nezvi_22408.WL.1 Fragment 14 | 34 | B | 60 | 6 |

Example 6: Construction of Hairpin Constructs for Plant Transformation

Figure 2:
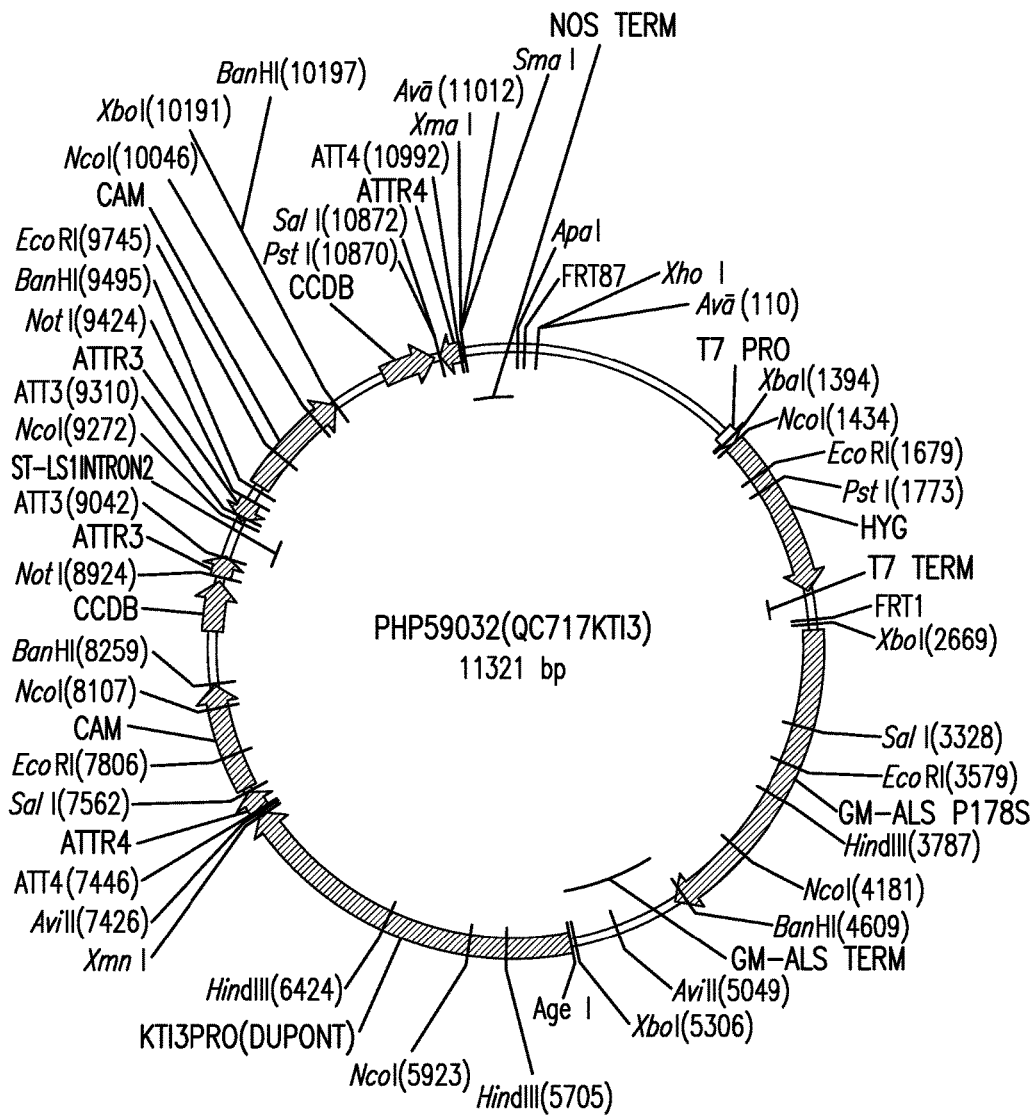
FIG. 2 is a map of plasmid PHP 59032.

A selection of the fragments that showed activity in the in vitro insect assay were used to make constructs for plant transformation. Fragments were amplified using gene specific primers flanked by sequence encoding an ATT B4 recombinase sequence (CAACTTTGTATAGAAAAGTTG; SEQ ID 13) on one side and an ATT B3 recombinase sequence (CAACTTTGTATAATAAAGTTG; SEQ ID 14) on the other side. The resulting amplified DNA was cloned into pCR2.1 and clones were sequenced. Sequence verified clones were recombined into plasmid PHP36164 (FIG. 1, SEQ ID 15) using a BP Gateway Reaction (Invitrogen). The resulting clones were then recombined into PHP59032 (FIG. 2, SEQ ID 16) using a LR Gateway Reaction (Invitrogen). The resulting plasmid contains a hairpin-structured transcript controlled by the seed specific promoter kit. The cassette comprising a promoter and terminator separated by a unique Not I restriction endonuclease site comprises the KTi3 promoter, a unique Not I restriction endonuclease site, and the KTi3 terminator region. This cassette comprises about 2088 nucleotides of the KTi3 promoter, a unique Not I restriction endonuclease site, and about 202 nucleotides of the KTi3 transcription terminator. The gene encoding KTi3 has been described (Jofuku, K. D. and Goldberg, R. B., *Plant Cell* 1:1079-1093 (1989)).

Figure 3:
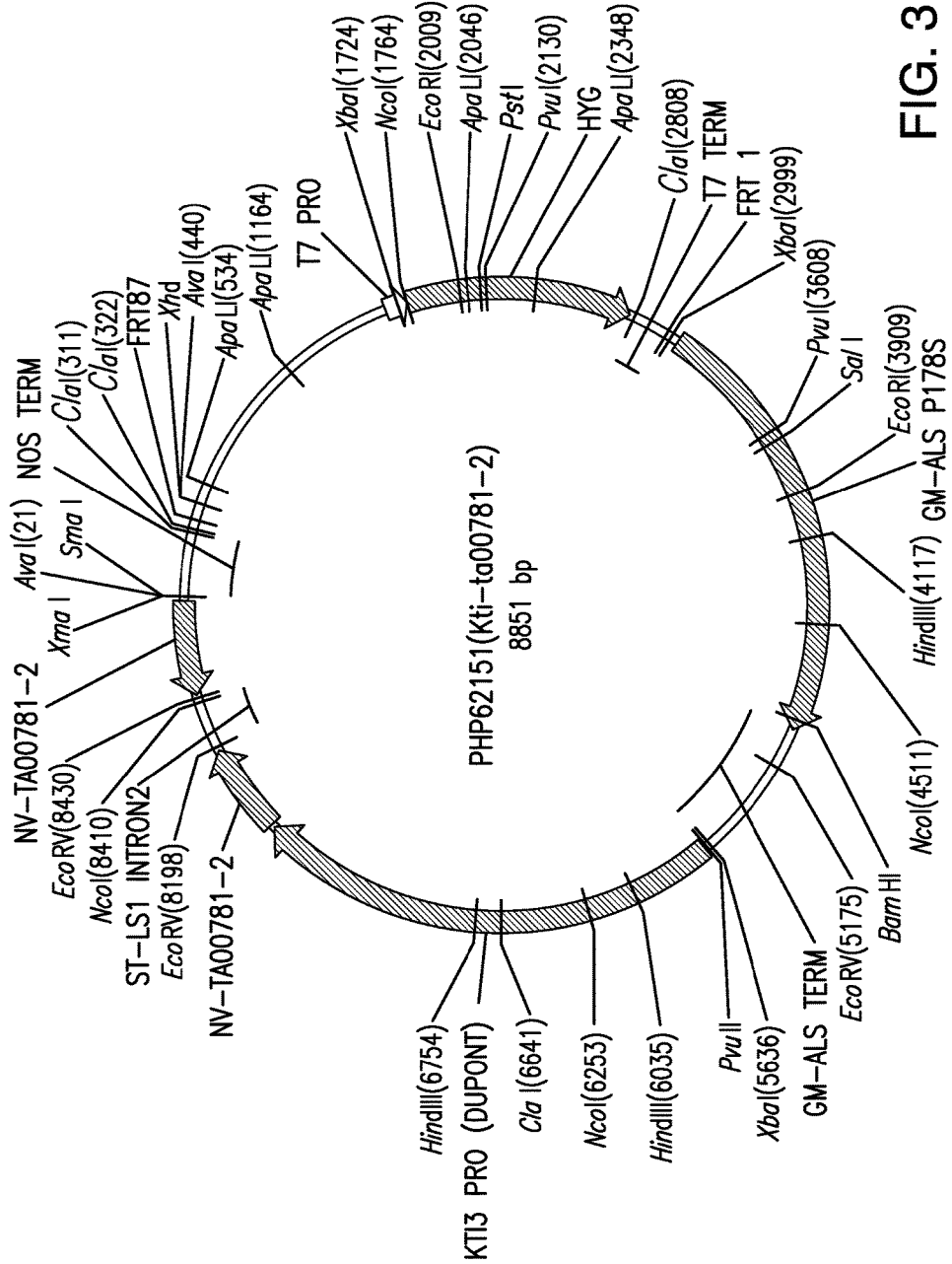
FIG. 3 is a map of plasmid PHP 62151.

It is understood that such a hairpin-structured transcript will form a dsRNA in vivo. The plasmid also contains a promoterless *Glycine max* acetolactate synthase (P178S) which is useful as a selectable marker. These two cassettes are flanked by FRT1 and FRT87 sites that are required for site specific integration during soybean transformation. An example of such a plasmid is PHP62151 (FIG. 3, SEQ ID 17).

Example 7: Transformation and Regeneration of Soybean (*Glycine max*)

Transgenic soybean lines are generated by the method of particle gun bombardment (Klein et al., *Nature* (London) 327:70-73 (1987); U.S. Pat. No. 4,945,050) using a BIO-RAD Biolistic PDS1000/He instrument and either plasmid or fragment DNA.

Integration of DNA into the soybean genome after particle gun-mediated transformation may be random, or it may be through site-specific integration (SSI), achieved by recombinase-mediated cassette exchange (RMCE) at a previously created transgenic target site (U.S. Pat. No. 7,102,055 issued Sep. 5, 2006). Recombinase-mediated DNA cassette exchange RMCE using different recombinase systems have been achieved successfully in several plants (Nanto K, Yamada-Watanabet K, Ebinuma H(2005) *Agrobacterium*-mediated RMCE approach for gene replacement. Plant Biotechnol J, 3: 203-214; Louwerse J D et al. 2007. Stable recombinase-mediated cassette exchange in *Arabidopsis* using *Agrobacterium tumefaciens*. Plant Physiol 145: 1282-1293; Li Z. et al. 2009, Site-specific integration of transgenes in soybean via recombinase-mediated DNA cassette exchange. Plant Physiol 151: 1087-1095). Groups of transgenes can be stacked to the same site through multiple rounds of RMCE (Li et al 2010, Published online before print August 2010, doi:10.1104/pp. 110.160093; Plant Physiology October 2010 vol. 154 no. 2 622-631). Taking advantage of reversible DNA cassette exchange in RMCE, an RMCE product can be used as a new target for subsequent SSI transformation.

The transgenic target site for RMCE may contain a promoter followed by recombination sites surrounding a selectable marker gene such as the hygromycin phosphotransferase (HPT) gene, with or without additional components. After bombardment with donor DNA, the target DNA previously integrated into the soybean genome recombines with the donor DNA at recombination sites such as FRT1 and FRT87 with the help of a transiently expressed recombinase such as the FLP recombinase. The portion of the DNA cassette in the target which contains the original selectable marker gene flanked by dissimilar recombination sites such as FRT1 and FRT87 is replaced by the donor DNA cassette flanked by the same FRT1 and FRT87 sites, resulting in site-specific integration of the donor cassette to the exact same genomic site of the target. The promoter existing upstream of the recombination sites in the transgenic target remains after RMCE to regulate expression of the new selectable marker gene delivered to the site as part of the donor cassette. Successful RMCE events may be identified by chemical selection for cells expressing the selectable marker gene of the donor.

Culture Media and Stock Solutions

The following stock solutions and media are used for transformation and regeneration of soybean plants:

Stock Solutions:

Sulfate 100× Stock:
37.0 g $MgSO_4.7H_2O$, 1.69 g $MnSO_4.H_2O$, 0.86 g $ZnSO_4.7H_2O$, 0.0025 g $CuSO_4.5H_2O$ Halides 100× Stock:
30.0 g $CaCl_2.2H_2O$, 0.083 g KI, 0.0025 g $CoCl_2.6H_2O$ P, B, Mo 100× Stock:
18.5 g $KH_2PO_4$, 0.62 g $H_3BO_3$, 0.025 g $Na_2MoO_4.2H_2O$ Fe EDTA 100× Stock:
3.724 g $Na_2EDTA$, 2.784 g $FeSO_4.7H_2O$ 2,4-D Stock:
10 mg/mL Vitamin B5 vitamins, 1000× Stock:
100.0 g myo-inositol, 1.0 g nicotinic acid, 1.0 g pyridoxine HCl, 10 g thiamine.HCL.

Media (Per Liter):

SB199 Solid Medium:
1 package MS salts (Gibco/BRL—Cat. No. 11117-066), 1 mL B5 vitamins 1000× stock, 30 g sucrose, 4 ml 2, 4-D (40 mg/L final concentration), pH 7.0, 2 g Gelrite™

SB1 Solid Medium:
1 package MS salts (Gibco/BRL—Cat. No. 11117-066), 1 mL B5 vitamins 1000× stock, 31.5 g Glucose, 2 mL 2, 4-D (20 mg/L final concentration), pH 5.7, 8 g TC agar SB196:
10 mL of each of the above stock solutions 1-4, 1 mL B5 Vitamin stock, 0.463 g $(NH_4)_2SO_4$, 2.83 g $KNO_3$, 1 mL 2.4 D stock, 1 g asparagine, 10 g sucrose, pH 5.7

SB71-4:
Gamborg's B5 salts, 20 g sucrose, 5 g TC agar, pH 5.7.

SB103:
1 pk. Murashige & Skoog salts mixture, 1 mL B5 Vitamin stock, 750 mg $MgCl_2$ hexahydrate, 60 g maltose, 2 g Gelrite™, pH 5.7.

SB166:
SB103 supplemented with 5 g per liter activated charcoal.
Soybean Embryogenic Suspension Culture Initiation:

Pods with immature seeds from available soybean plants 45-55 days after planting are picked, removed from their shells and placed into a sterilized magenta box. The soybean seeds are sterilized by shaking them for 15 min in a 5% Clorox solution with soap or other surfactants at 1 drop per 100 mL solution. Seeds are rinsed with sterile distilled water, and those less than 4 mm are placed on a sterile surface under microscope. The small ends of seeds are cut, and the cotyledons are pressed out of the seed coats. Cotyledons are transferred to plates containing SB199 medium (25-30 cotyledons per plate) for 2 weeks, then transferred to SB1 for 2-4 weeks. Plates are wrapped with fiber tape and cultured for 8 weeks in growth chamber room with temperature set at 24.4-26° C. and light on a 16:8 h day/night photoperiod at an intensity of 45-65 µE/m2/s. After this time, secondary embryos are cut and placed into SB196 liquid medium for 7 days.

Culture Conditions:

Soybean embryogenic suspension cultures are maintained in 50 mL liquid medium SB196 on a rotary shaker at a speed of 100-150 rpm. The cultures are set in a growth chamber with temperature set at 24.4-26° C. and light on a 16:8 h day/night photoperiod at intensity of 80-100 µE/m2/s for liquid culture and 80-120 µE/m2/s for maturation and germination. Cultures are subcultured every 7-14 days by inoculating up to ½ dime size quantity of tissue into 50 mL of fresh liquid SB196.

Preparation of DNA for Bombardment:

In particle gun bombardment procedures it is possible to use purified 1) entire plasmid DNA; or 2) DNA fragments containing only the recombinant DNA expression cassette(s) of interest. For every bombardment experiment, 85 µL of suspension is prepared containing 1 to 90 pg of plasmid DNA per base pair of DNA. To prepare for an SSI transformation, the donor plasmid is mixed with plasmid DNA containing the FLP recombinase gene cassette in a ratio such as 3:1. Both recombinant DNA plasmids are co-precipitated onto gold particles as follows. The DNAs in suspension are added to 50 µL of a 10-60 mg/mL 0.6 µm gold particle suspension and then combined with 50 µL $CaCl_2$ (2.5 M) and 20 µL spermidine (0.1 M). The mixture is vortexed for 5 sec, spun in a microcentrifuge for 5 sec, and the supernatant removed. The DNA-coated particles are then washed once with 150 µL of 100% ethanol, vortexed and spun in a microcentrifuge again, then resuspended in 85 µL of anhydrous ethanol. Five µL of the DNA-coated gold particles are then loaded onto each macrocarrier disk.

Tissue Preparation and Bombardment with DNA:

Approximately 100-200 mg of two-week-old suspension culture is placed in an empty 60 mm×15 mm petri plate and the residual liquid removed from the tissue using a pipette. The tissue is placed about 3.5 inches away from the retaining screen. Membrane rupture pressure is set at 650 psi and the bombardment chamber of the particle gun is evacuated to −28 inches of Hg prior to bombardment. Typically, each plate of tissue is bombarded once.

Selection of Transformed Embryos and Plant Regeneration:

After bombardment, tissue from each bombarded plate is divided and placed into one to two flasks of SB196 liquid culture maintenance medium per plate of tissue, one flask per 100 mg tissue. Seven days post bombardment, the liquid medium in each flask is replaced with fresh SB196 culture maintenance medium supplemented with 100 ng/ml selective agent (selection medium). For selection of transformed soybean cells after random transformation or RMCE, the selective agent used can be a sulfonylurea (SU) compound with the chemical name, 2-chloro-N-((4-methoxy-6 methyl-1,3,5-triazine-2-yl)aminocarbonyl) benzenesulfonamide (common names: DPX-W4189 and chlorsulfuron). Chlorsulfuron is the active ingredient in the DuPont sulfonylurea herbicide, GLEAN®. The selection medium containing SU is replaced every two weeks for 8 weeks. After the 8 week selection period, islands of green, transformed tissue are observed growing from untransformed, necrotic embryogenic clusters. The putative transgenic randomly integrated or RMCE events are isolated and kept in SB196 liquid medium with SU at 100 ng/ml for another 5 weeks with media changes every 1-2 weeks to generate new, clonally propagated, transformed embryogenic suspension cultures. Embryos spend a total of around 13 weeks in contact with SU. Suspension cultures are subcultured and maintained as clusters of immature transgenic embryos and also regenerated into whole plants by maturation and germination of individual somatic embryos.

Transgenic somatic embryos become suitable for germination after four weeks on maturation medium (1 week on SB166 followed by 3 weeks on SB103). They are then removed from the maturation medium and dried in empty petri dishes, or with a small amount of medium, for approximately seven days. The dried embryos are then planted in SB71-4 medium where they are allowed to germinate under the same light and temperature conditions as described above. Germinated embryos are allowed to develop into small plantlets and are then transferred to potting medium and grown to maturity for seed production.

Example 8: Bioassay of Soybean Plants

After transformation, transgenic soybean plants will be grown in the greenhouse and seeds will be harvested from these transformed plants and designated as T1 seeds. T1 seeds will be chipped manually and DNA extracted from the chips will be used to determine zygosity using a quantitative PCR assay. Homozygous seeds will be sown in 2.5 inch pots, maintained in the growth chambers in 16:8 (light:dark) cycle in an insecticide free environment. After about 4 weeks, these plants will be transplanted to a larger pot and maintained at 14:10 (light:dark) cycle for 2 weeks. After two weeks, the plants will be maintained in 12:12 (light:dark) cycle to induce flowering and delivered for bioassay at R3 stage. Fertilizer will be provided as needed and chambers are maintained at 50% relative humidity. Ten second instar southern green stinkbugs will be used to infest soybean pods at various stages: R3 (beginning pod), R4 (full pod), R5 (beginning seed), R6 (full seed) and R7 (beginning maturity). Insects will be maintained on the pods using enclosures. Developmental stage, stunting (% control as outlined in example 5) and mortality will be recorded at 8-10 days after initial infest of the transgenic soybean pods.

Example 9: Alternative Sequences for Nezvi_22408.WL.1 and inv2c.Pk011.b22.f

A transcriptome is a collection of all the transcripts present in a given cell. As such, a transcriptome includes alternative spliced variants that are present within the cell. For nezvi_22408. WL.1 two alternatively spliced variants are predicted: nezvi_22408. WL.2 (SEQ ID 18) and nezvi_22408. WL.3 (SEQ ID 19). RT-PCR as described in Example 1 along with primers that were designed to amplify transcript specific sequences as well as cloning and sequence verification show that all three transcripts are real and exist in second instar southern green stinkbug mRNA.

Similarly, it is understood that cDNA library sequences may not encode the entire transcript. The sequence for the clone inv2c.pk011.b22.f (SEQ ID 10) was used to BLAST query the transcriptome and a longer sequence named nezvi_3755. WL.1 (SEQ ID 20) was found.

What is claimed is:

1. An expression cassette, comprising a heterologous promoter operably linked to a polynucleotide encoding a double stranded RNA, wherein the double stranded RNA comprises the sense and antisense sequence of a nucleotide sequence selected from the group consisting of:

(a) a nucleotide sequence comprising any one of SEQ ID NOS: 9, or 30-34;
(b) a nucleotide sequence comprising at least 95% sequence identity to any one of SEQ ID NOS: 9, or 30-34; and
(c) a nucleotide sequence comprising at least 23 consecutive nucleotides of any one of SEQ ID NOS: 9, or 30-34;
wherein said double stranded RNA has insecticidal activity against a Pentatomidae plant pest.

2. The expression cassette of claim 1, wherein said Pentatomidae plant pest is a *N. viridula* plant pest.

3. The expression cassette of claim 1, wherein said double stranded RNA is expressed as a hairpin RNA.

4. The expression cassette of claim 3, wherein the double stranded RNA comprises, a first segment, a second segment, and a third segment, wherein
   a) said first segment comprises a sense or antisense nucleic acid sequence of at least 23 nucleotides of a target sequence set forth in SEQ ID NOS: 9, or 30-34;
   b) said second segment comprises a loop of sufficient length to allow the double stranded RNA to be transcribed as a hairpin RNA; and,
   c) said third segment comprises a sense or antisense nucleic acid sequence of at least 23 nucleotides having at least 95% complementarity to the first segment.

5. The expression cassette of claim 1, wherein said polynucleotide is flanked by a first operably linked convergent promoter at one terminus of the polynucleotide and a second operably linked convergent promoter at the opposing terminus of the polynucleotide, wherein the first and the second convergent promoters are capable of driving expression of the double stranded RNA.

6. A host cell comprising a heterologous expression cassette of claim 1.

7. A plant cell having stably incorporated into its genome a heterologous polynucleotide encoding a double stranded RNA, wherein the double stranded RNA comprises the sense and antisense sequence of a nucleotide sequence selected from the group consisting of:
   a) at least 23 consecutive nucleotides of SEQ ID NOS: 9, or 30-34; or,
   b) the nucleotide sequence comprising at least 95% sequence identity to any one of SEQ ID NOS: 9, or 30-34,
   wherein said polynucleotide encodes a double stranded RNA that controls the Pentatomidae plant pest.

8. The plant cell of claim 7, wherein the Pentatomidae plant pest is a *N. viridula* plant pest.

9. The plant cell of claim 7, wherein said double stranded RNA comprises
   a) a polynucleotide comprising a sense or antisense sequence of a nucleotide sequence as set forth in SEQ ID NOS: 9, or 30-34;
   b) a polynucleotide comprising a sense or antisense sequence of at least 75 consecutive nucleotides of a nucleotide sequence as set forth in SEQ ID NOS: 9, or 30-34.

10. The plant cell of claim 7, wherein said double stranded RNA expresses a hairpin RNA.

11. The plant cell of claim 10, wherein said polynucleotide comprising the double stranded RNA comprises a first segment, a second segment, and a third segment, wherein
   a) said first segment comprises a sense or antisense nucleic acid sequence of at least 23 nucleotides complementarity to a target sequence set forth in SEQ ID NOS: 9, or 30-34;
   b) said second segment comprises a loop of sufficient length to allow the silencing element to be transcribed as a hairpin RNA; and,
   c) said third segment comprises a sense or antisense nucleic acid sequence of at least 23 nucleotides having at least 95% complementarity to the first segment.

12. The plant cell of claim 7, wherein said polynucleotide is operably linked to a heterologous promoter.

13. The plant cell of claim 7, wherein said plant cell is from a monocot.

14. The plant cell of claim 13, wherein said monocot is maize, barley, millet, wheat or rice.

15. The plant cell of claim 7, wherein said plant cell is from a dicot.

16. The plant cell of claim 15, wherein said dicot is soybean, canola, alfalfa, sunflower, safflower, tobacco, *Arabidopsis*, or cotton.

17. A plant or plant part comprising a plant cell of claim 7.

18. A transgenic seed from the plant of claim 17.

19. A method for controlling a Pentatomidae plant pest comprising feeding to a Pentatomidae plant pest a composition comprising a double stranded RNA, wherein said double stranded RNA, when ingested by said Pentatomidae plant pest, reduces the level of a target Pentatomidae plant pest sequence and thereby controls the Pentatomidae plant pest, and wherein said double stranded RNA comprises
   a) the sense and antisense sequence of at least 23 consecutive nucleotides of SEQ ID NOS: 9, or 30-34; or,
   b) the sense and antisense sequence of a nucleotide sequence comprising at least 95% sequence identity to any one of SEQ ID NOS: 9, or 30-34.

20. The method of claim 19, wherein said Pentatomidae plant pest comprises a *N. viridula* plant pest.

21. The method of claim 19, wherein said composition comprises a plant or plant part having stably incorporated into its genome a polynucleotide encoding said double stranded RNA.

22. The method of claim 21, wherein said double stranded RNA comprises
   a) the sense or antisense sequence of the sequence set forth in SEQ ID NOS: 9, or 30-34;
   b) the sense or antisense sequence of a sequence having at least 95% sequence identity to the sequence set forth in SEQ ID NOS: 9, or 30-34;
   c) the sense or antisense sequence of a sequence having at least 75 contiguous nucleotides of SEQ ID NOS: 9, or 30-34.

23. The method of claim 22, wherein said double stranded RNA comprises a hairpin RNA.

24. The method of claim 23, wherein said polynucleotide encoding the double stranded RNA comprises a first segment, a second segment, and a third segment, wherein
   a) said first segment comprises a sense or antisense nucleic acid sequence of at least 23 nucleotides complementarity to the target polynucleotide;
   b) said second segment comprises a loop of sufficient length to allow the silencing element to be transcribed as a hairpin RNA; and,
   c) said third segment comprises a sense or antisense nucleic acid sequence of at least 23 nucleotides having at least 95% complementarity to the first segment
   wherein said double stranded RNA has insecticidal activity against a Pentatomidae plant pest.

25. The method of claim 21, wherein said polynucleotide is operably linked to a heterologous promoter.

26. The method of claim 21, wherein said polynucleotide is flanked by a first operably linked convergent promoter at one terminus of the polynucleotide and a second operably linked convergent promoter at the opposing terminus of the polynucleotide, wherein the first and the second convergent promoters are capable of driving expression of the double stranded RNA.

27. The method of claim 19, wherein said plant is a monocot.

28. The method of claim 27, wherein said monocot is maize, barley, millet, wheat or rice.

29. The method of claim 19, wherein said plant is a dicot.

30. The method of claim 27, wherein said dicot is soybean, canola, alfalfa, sunflower, safflower, tobacco, *Arabidopsis*, or cotton.

* * * * *

```
                            SEQUENCE LISTING

<160> NUMBER OF SEQ ID NOS: 40

<210> SEQ ID NO 1
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 1
taatacgact cactataggg                                                 20

<210> SEQ ID NO 2
<211> LENGTH: 44
<212> TYPE: DNA
<213> ORGANISM: Artificial Sequence
<220> FEATURE:
<223> OTHER INFORMATION: Description of artificial sequence note =
      synthetic construct

<400> SEQUENCE: 2
taatacgact cactataggg atgcccggga attcggccat tacg                       44

<210> SEQ ID NO 3
<211> LENGTH: 46
<212> TYPE: DNA
<213> ORGANISM: Artificial Sequence
<220> FEATURE:
<223> OTHER INFORMATION: Description of artificial sequence note =
      synthetic construct

<400> SEQUENCE: 3
taatacgact cactataggg cgcgccaaac gaatggtcta gaaagc                     46

<210> SEQ ID NO 4
<211> LENGTH: 44
<212> TYPE: DNA
<213> ORGANISM: Artificial Sequence
<220> FEATURE:
<223> OTHER INFORMATION: Description of artificial sequence note =
      synthetic construct

<400> SEQUENCE: 4
taatacgact cactataggg ctagtaacgg ccgccagtgt gctg                       44

<210> SEQ ID NO 5
<211> LENGTH: 44
<212> TYPE: DNA
<213> ORGANISM: Artificial Sequence
<220> FEATURE:
<223> OTHER INFORMATION: Description of artificial sequence note =
      synthetic construct

<400> SEQUENCE: 5
taatacgact cactataggg ggccgccagt gtgatggata tctg                       44

<210> SEQ ID NO 6
<211> LENGTH: 2969
<212> TYPE: DNA
<213> ORGANISM: Artificial Sequence
```

<220> FEATURE:
<223> OTHER INFORMATION: Description of artificial sequence note = synthetic construct

<400> SEQUENCE: 6

| | | | | | |
|---|---|---|---|---|---|
| cagagatggc | agagatggga | agttgatagc | cagatctgac | agagtcaagt | gtgttgactt | 60 |
| acatccatca | gaaccatgga | tgttggcttc | tttatacaat | ggaaacgttc | atatttggaa | 120 |
| tcatgagacc | cagcagctag | taaagtcttt | tgaagtatgc | gaccaaccag | ttcgtgctgc | 180 |
| agtatttgtt | cctcgcaaga | actggattgt | aacagggtca | gatgatatgc | agatcagagt | 240 |
| ttttaattac | aatactcttg | aaagagtaaa | tgcatttgaa | gctcattcag | actatgtcag | 300 |
| atgtatagca | gttcacccag | cccatcctta | tattctgaca | tcatcagatg | atatgttaat | 360 |
| caaattgtgg | aattggtcta | aggcttgggt | ctgccaacaa | atatttgaag | gacatacccac | 420 |
| ttatgtaatg | caagttgtta | taaatccaaa | agataataat | acatttgcat | ctgcttcatt | 480 |
| agatcggact | gttaaagttt | ggcagttagg | ctctgctgct | ccaaattta | ctttagaagg | 540 |
| tcatgaaaaa | ggagttaatt | ctgtcgatta | ttatcatggt | ggtgacaaac | cttatctcat | 600 |
| atctggcgcc | gacgatcatc | ttgtcaaaat | atgggattat | caaataaga | cttgtgttca | 660 |
| aaccttggag | ggccatgccc | agaatattac | tgcagttttgt | tttcacactg | aactacctat | 720 |
| tataataact | gggtcagaag | atggaactgt | tcgattatgg | cactcagcaa | cttacagatt | 780 |
| ggaatcatct | cttaactatg | gcctagaacg | tgtttggact | attgcgaggc | tgaaaggatc | 840 |
| aaacaatata | gctcttggat | atgatgaagg | gagtatcatg | gtgaagatag | gacgtgaaga | 900 |
| accagcaatt | tcaatggatg | tgaatggtga | aaaaatagtt | tgggccagac | attctgaaat | 960 |
| tgaacaggta | aacttgaagc | aagtttcagg | agaagtaaga | gatggcgaac | gtcttgctttt | 1020 |
| agctccaaaa | gaaatgggac | catgtgaaat | atatcctcaa | agtatttcac | ataatccaaa | 1080 |
| tggaagattt | gtcgttgttt | gtggagatgg | tgaatacata | atttatactg | ctatggcttt | 1140 |
| aagaaacaaa | agttttggat | cagcccaaga | atttgtatgg | gcacaagata | gttctgacta | 1200 |
| tgctataaga | gaaggaacat | ctactgtaaa | actatttaga | cagttcaagg | agcgcaagac | 1260 |
| acttaagcca | gagtttggtg | ctgaaggtat | atttggtgga | caattgcttg | gtgtcagatc | 1320 |
| agtctcagga | ttatgtttat | atgattggga | aactctggaa | ttaatcagaa | gaatagaaat | 1380 |
| tcaggcaaaa | tctctccatt | ggtctgattc | tggacatctt | cttgctattg | taacggatga | 1440 |
| ttcctattat | atattgaagt | atgattcatc | cgcaatcgcc | agtgctcaag | agagaactcc | 1500 |
| tgatggtgtt | gaagctgcat | tttctcttgt | cggagaagta | aatgacacag | taaagacagg | 1560 |
| tttgtgggtt | ggcgattgtt | ttatttacac | caatgctgtt | gggcgaataa | attattacgt | 1620 |
| tggaggagaa | atagtgactg | ttgctcactt | ggattgcact | atgtacctgt | tgggatatgt | 1680 |
| ggctaggcaa | aatctttat | acctttctga | taaacatcac | aatattgttt | gttatacatt | 1740 |
| attactttct | gttcttgaat | atcaaacagc | tgttatgaga | ggagattttg | aaacagctga | 1800 |
| ccgtgtgttg | ccaacaattc | cagttcagca | tcgttcccgg | tagcccactt | cttggaaaaa | 1860 |
| cagggctttta | aaaagaagc | tctggctgta | tctactgatc | cagaacataa | atttgaatta | 1920 |
| gctcttggac | taaagagct | cgatacggtt | gttcagttag | ctgaggaaat | aggtagcaca | 1980 |
| gccaagtggg | gtcaagccgc | tgaattagca | acgagacaag | ccaggcttga | tgttgcgcaa | 2040 |
| gcagctcttc | acagagccca | acattatggt | ggacttctgc | ttctctccac | atcagcagga | 2100 |
| aatcgggaaa | tgatgaaaaa | acaggaagag | gttcaggaga | aaatgaaaaa | aataatgtta | 2160 |
| gcttccttgc | atatttcctg | cttggagacc | ttgccaaatg | tcttcaaatt | cttattgaca | 2220 |

```
ctgatcgcat tccagaagct gccttttttg ccaggacata tttgccgagt gaggttcctc    2280
gagttgttgg gttatggcga ggtttagcaa aggcaggaca gagccttgca gatccttcgc    2340
agtatctaat ctcttttccag gttatgcaga tgctttaaaa actgaacagt atttagcaaa   2400
gaatcctgtg tgactaaacc agcttcttat cataaaaata ttaaggttat attttttatta  2460 gtattattca tatatattat gtatattata tagcatgtaa ttgggtactt gagcagaaaa    2520
aaatacatgt caatttgaga catagtagaa ataagtgac aaagagcata tatacattg     2580 agatagcatt ttttaaatta caaaaaaaag agctcatatt tgactaaaaa cttgaaataa   2640
cagtgtgcct gggggctacc aaagtggggc tggggtgtcc tgagaacaca cctgaaaaat   2700
attttagtat gaatgaaatt tctaggtaat gaaaaaatat atcaatatac attttatttg   2760
taaaaaaaaa gtggaaaaac ataaaatgta attttcatct aaaagaattc ttagtgtaca   2820
tttataaaaa tgggccatta ttaaattatt tcataaagcc atgaaaattc tatgtagaga   2880
ttttttttta aactttcgag atacagaggt ttgactattc ttcaggtcta accaatattt   2940
ttgtttgcta gaaacaaccct aatcgtaat                                     2969
```

```
<210> SEQ ID NO 7
<211> LENGTH: 4838
<212> TYPE: DNA
<213> ORGANISM: Artificial Sequence
<220> FEATURE:
<223> OTHER INFORMATION: Description of artificial sequence note =
      synthetic construct

<400> SEQUENCE: 7
```

```
aatattaaat tatgagagtt ttttttgttg atatgaaata acaagtgctt ggctgtttta     60
tttcccaaag aagtattgag tgaataaata tcaagatatt gaattataat ttcctattta   120
aggatggctg tggtggaaca accttgttat actctgatca attttccatc tgatttagag   180
cctcctaatg aaatgcagct aaaatctgat ttagaaaatg gagacactaa agcgaaaatt   240
gaagctttga aaaatattat tcatttaatt gcaaatggag agcgtctacc tggtttactt   300
atgcatatca tacgttttgt tttgccatca caagaccata ccataaaaaa attactgctt   360
atattttggg aaatcgttcc taaaactact ccagatggca aacttctcca ggaaatgatt   420
ttggtttgtg atgcctatcg gaaggactta caacatccta tgaatttgt cagggatct    480 acattacgtt ttctatgtaa acttaaagaa cctgaattgc ttgagccttt aatgcctgct   540
ataagagctt gtttagagca tcgggtttca tatgtacgaa gaaatgcagt acttgcaata   600
tttaccattt ataggaattt tgaattctta gctcctgatg caccagaact tattgctaat   660
ttcttagatg gggagcaaga catgtcatgt aaaagaaatg ctttcttaat gctcctacat   720
gctgaccaag aacgtgcctt atcctactta gcttcatgtc ttgatcaagt gacttccttt   780
ggcgatatac ttcaattagt tattgttgaa ttaattata aggtttgcca tgctaaccct    840
tctgaacgtt ctcgatttat acgttgcatt tataatttac tcaattctaa cagtcctgct   900
gtgcgatatg aagctgctgg aactttaatc acactttcga atgctcctac tgcaataaaa   960
gctgctgctt cttgttacat tgatttgata ataaggaaa gtgataataa tgttaaatta   1020
attgtattag atcgtcttat atctttaaaa gaaattccta ctcatgaacg ggttcttcaa   1080
gatttagtta tggatatatt acgtgtgcta gccagtcctg acatggaagt aaagaaaaaa   1140
gccttaagcc tagcactgga tctcactact tcacggtgtg ttgaagaaat ggttttaatg   1200
ttaaaaaaag aagttgctaa gacacataac ttgacagaac atgaagatgc tggaaaatat   1260
```

```
cgtcaacttc ttgttagaac tcttcattcc tgttgcatga agtttccaga tgttgctgct   1320
tcagttatac cagtattaat ggaatttctc tcagatacaa gtgaactagc ttcgtatgat   1380
gttcttatat ttgtccgaga agcaattcat aagtttgatt ctttaagggt tttgatcata   1440
gagaaattat tagaagcgtt tccaaccata aaatctatga aagttcatcg agctgctctt   1500
tggatattgg gtgaatatac tacttcagtt acagatatta agaagtcat gaaacaaata    1560 aaacatgccc ttgagagat accacttgtc gatgatgaaa taaaaagagc ttctggagag    1620
aaagttgagg aagttgatca tcgagatcaa gtaaaactgg ttacatctga tggaacatat   1680
gctacacaat caatatttaa caccattctg gcaattaaaa aagaggatcg acctcctctc   1740
agacaatact tgattgatgg agactttttt attggtgtat ctgtggcttc tacgcttgtg   1800
aaattagcat tacgttataa agagcttgtt cagcaggaaa atatgtacca taaattttt    1860 gctgagtgta tgctaatcat ttcatctata gttcgtctgg gtaaatctgg atatccttcg   1920
aaacagctga gctatgatga ttatgaacga atgttacttt gtctaaaggt tctctctgaa   1980
aataatgcac ctattgtaaa aattttcaac actgattgtc gcaatgctct tgctaatatg   2040
ttagttgctc aacagaatga ggagtactca cttattaagg ccaaagaaaa atccgtccat   2100
accatccaag ttgatgatcc tgtatcattt ttacaattat caacgatacg atcatctgat   2160
tttggttcag aaaatgtttt tgagcttagt ttaaatcaag ctgtcggggg gccaaataca   2220
gctacaaaca cagctgaact tccattttca gccagtaaat tgaataaagt aactcagctg   2280
acagggtttt cagatccagt ttatgcagaa gcatatgttc atgtcaacca gtatgacatt   2340
gtacttgatg ttttgatcgt taatcaaaca ggtgatacac ttcaaaactg tacgcttgaa   2400
ctagcaactc ttggtgatct gaagcttgtc gaaaaacctc aaccttgtgt tctagctcct   2460
tatgatttct gcaacattaa agcaaatgtg aaggttgcat ctactgaaaa tggaatcata   2520
tttggcaata ttgtttatga tattagtgga gctgcttctg acagaaacgt tgttgttctt   2580
aatgatatcc atatagatat catggattat attgttcctg ctatctgttc agacacagaa   2640
tttcgtcaga tgtgggctga atttgagtgg gaaaacaagg tgtcagttaa cacttatttg   2700
gtcgatcttc atgaatatct tggccatta ttgaagagca ctaatatgaa atgtttaaca    2760
ccagaaaaag ctctatgtgg gcaatgtgga tttatggctg ctaatatgta tgcccgttca   2820
atttttggtg aagatgcact tgctaactta agcatcgaaa aaccgtttaa taagcctaat   2880
gcacctgtta ctgggcatat tagaatcaga gctaaaagcc agggtatggc attaagctta   2940
ggagataaaa ttaatatgac ccagaagaaa cctactatca tggctcagtg aaacataata   3000
gtttcattgt taaaatgcat ttcaagattg tttagacttt ttatatctat tggtttataa   3060
gtatttggaa ttatgggatt cacaactctg aatttgttaa agtattttaa atcaagttat   3120
caaaaattat ttttacttca atctaatagt tgtacattat tattagatgt gagtacctac   3180
aaatatatag attttttgta cctttctatg acttattaaa atatttcatt tgatgtacat   3240
tatatattgt tgacctaaat taaaaagct tatgtatctt attcttaaat ttgtttttat    3300
tattcttaga ataatgctat tatattttgt gatatctcaa tttgaaaata gtatatatgt   3360
gtgtgtgtta atatacatgt gtatattatt aatattctaa taataaatat ttatatttaa   3420
aagtcagtaa aattatatgt atgtttgtat aactatactg ggtgtcctgt aaatagagag   3480 acattttgt aggagttata gcagatctca agaactacaa aaaaattcat ataaacaatg    3540
ggccttaatt ttcagctgaa aagtaggaaa ttcaatttct ttttttttag caacctacac   3600
```

| | |
|---|---|
| aaaatttacc tcaaattaaa atacagtttg tcatcgttaa aaccatttaa agaggacttt | 3660 |
| aaaatggcta aattaagctt aaaaaaatca taaataacta gtgatttttt tttgcaatta | 3720 |
| ttcatcatct aaagtggtac tttgttttta ataagatcta tattattgga attaattcat | 3780 |
| acttttaagt gatgcaataa ctgtttctag tcgtaacatt tacatttaaa ataaagaaac | 3840 |
| ctgctgattg cttcaattat tttcatgaaa acgtaaatat taggatcagg aacatttatt | 3900 |
| ttatcactta taaacacgaa tctattccta aatataata ttcctataat atagatctta | 3960 |
| gtaaaaaacg aattttagt accactttag atgatgaacc atcgcaaaaa cattatttta | 4020 |
| aacttttttt taaaatttt atttatgcat ttatatttat taataacat cccagatcat | 4080 |
| ggaaaaacat gaaattaaag ttttgcaaca gtttattgta gtcttttgc tgaaaatacg | 4140 |
| ggtattttt ggatgactgg ttaaaaaaac acaaattgtt tttacataac ttgatgtgga | 4200 |
| tctcaaatgt ttgcctaata aacctcaact taattaatat tgacttaaag gttattaaac | 4260 |
| ctcggaagtt tttctaaaag tgaggtatct gtagtacagt tagaggatga taaaaacaaa | 4320 |
| tcgtgaataa cttatgatta tttttaaaaa acagaactta ggttagttta gccatttaaa | 4380 |
| gatcctcttt aaatggtttt agcaatgaca aattgtattt tgatttgagg taaatttgt | 4440 |
| gtagtttgct gaggagcaat tgttaattat ataaataaaa tattttttta gttgtcgctt | 4500 |
| tattttacta aaaagaggc ttcattaaaa aatatataac ttggatttcc tactttttctg | 4560 |
| ctgaaaatta gcccattgtt tgtataacat ttttgtagct cttgaggtct gctatctctc | 4620 |
| ctataaaaat ttccctctac ttacaggaca tcctgtatat gtgttgaagt ttgcatgaat | 4680 |
| gttactttg tttttgttt tttaattttt tcaggtcaag ttaatacata tattattaat | 4740 |
| tttatataaa tatatatatg aattattttt ggaccattat taaaaatatg ttgtaactaa | 4800 |
| aataaataaa aataattat taaaagtcca aaaaaaa | 4838 |

<210> SEQ ID NO 8
<211> LENGTH: 3171
<212> TYPE: DNA
<213> ORGANISM: Artificial Sequence
<220> FEATURE:
<223> OTHER INFORMATION: Description of artificial sequence note = synthetic construct

<400> SEQUENCE: 8

| | |
|---|---|
| ctgttgacgt tgacgtggga tgtgtagtta atgtttaata attatttgtg taattttaa | 60 |
| tttgtaatat attaataaca tatttataac caataaaaat ggcaataaaa cgagataaga | 120 |
| aagaagaaga agatggtgga aacccctttc agagtcttga taagaccagt gttcttcagg | 180 |
| atgccagaac ttttaatgaa acaccagttg aacctcgcaa atgcaccca atattgacca | 240 |
| aaattctgta tcttttaaac caaggagaac agcttggtcc tgctgaagca acagaaacat | 300 |
| tttttgctgt tacgaagctt tttcaatcaa ataatacttt gcttcgacga atggtatatc | 360 |
| ttggcataaa agagttatct ctaattgctc aagatgttat catcgttact tctagcctta | 420 |
| caaaagacat gactgggaaa gaagatttat atcgagcagc tgcaattcga gcattatgca | 480 |
| gtataacaga tgctactatg ctgcagacga ttgaaagata tatgaaacaa gcaatcgttg | 540 |
| atagaaaccc agctgttgct agtgctgctc ttgttagttc actgcatatg agtaggatcg | 600 |
| ctagcgatgt cgtcaagaga tgggttaatg aagcacaaga agctgttaat tctgacagta | 660 |
| taatggtcca atatcatgct ctgggcctcc ttttccatat taggaaaaat gacagattgg | 720 |
| ctgtaacaaa attagttgct aaattaacta gaatgtcgtt gaaatctcca tttcgcagtt | 780 |

-continued

```
tgtatgttga ttcgaattgc atgtaaatta ttggaagaag aaagctctgg agaatatgca    840
gactctccac ttttttgattt tattgaagca tgtttacgcc acaaaagtga aacagttgtt    900
tatgaagcag ctgctgctct tgtaaactta cgccacacta ctaccagaca aatcacgcct    960
gcagtaagtg ttcttcaatt attttgttct tctccaaaac cagcgcttcg ttttgctgct   1020
gtgagaactc ttaataaggt agcaatgaca catcccactg ctgtaacgtc atgcaatatt   1080
gacttagaga accttataac ggattcaaat cggtccatag ctaccttggc cataactact   1140
cttctaaaaa ctggagctga atcagctgtg gacagactta tgaagcagat agcatctttc   1200
gtttcagaaa taagtgatga attcaagatt gttgtagtgc aggccattag agcactatgc   1260
ttgaaattcc ctcgaaaaca tggaacactc atgacgtttt tgtctgcgat gctgagggat   1320
gagggaggat tggagtataa ggcttcaatc gccgatacac ttatatctct tatcgaaggg   1380
aaccctgaag cgaaagagtc tggcctcgct catttgtgtg aattcatcga ggattgtgag   1440
catacttccc tggctgtcag gatactgcat ctgcttggta agaaggacc aaaaacaaaa    1500
cagccttcta ggtacataag attatctat aatagagtca ttctggaaaa tgcagtagta   1560
cgagcagctg ctgtttctgc attgtctcaa tttggagctc agtgccctga tcttcttgag   1620
aacatactag tcctcctcgc ccggtgccaa atggatacag acgatgaagt tagggacagg   1680
gccacatatt atttcagtat tttacaaaat caagatcgac atttgattaa taattacata   1740
gttgaaccac ctcaggtgtg tgtttccagt ttagaaaaag ccttaatgct gcatttgatg   1800
gaaactccag aagaagtatt tgacttgagt tctgttccgt tggcaccccc tcctctatcc   1860
gacgaagttc aggctgctcc aactgttgta caggaaccat tagcggcttt gggacgtcct   1920
gcggtctcca agaagagag tgcttctgat agacttcgag ctattccaga actttcttgg   1980
attcagggtc cactcttcaa aagttccgat cctatcagtc ttacggaatc tgagacagaa   2040
tatcaagtta gagtcacgaa gcatgttttc aaaaatcata ttgttcttca gtttgactgt   2100
acaaatacca tgagtgacca gctactggag aaagttcgag tgcagttaga agtgagcgaa   2160
ggttaccaga tcgtagctga ggtcccctgc caaagattag cctgttcgga aacatcacct   2220
acttatattg ccctgcaatt tccagatgcc cctaatctta ctgtcacaaa ctttgctgct   2280
actctgaggt ttgttgtaaa ggattgcgac ccaatgaccg gtatccctaa ctcagatgat   2340
ggttatgaag aagattatat gcttgaagat gtcgaagtga tgcttgctga ccaaatgcag   2400
cgacttacga agagcaactt cggtgctgca tgggaggaag gcgaatcgta tagtgagcta   2460
gaggacactt ataacttgtc aggaataaac agcctgaag aggcagtgag gagtgttgtc    2520
agtttcatgg ggatgcagcc tgctgacagg agcgacaggg tacagcctga taaatcttca   2580
cacactgtct acctcggagg catgttccgt ggtggagttg aagtgttagc tagagctaaa   2640
ctggccatgg gtaattcccc aggcgttgcc atgcaactta cagtccgctc tccaaatcca   2700
gatatttgtg aactgattat ttctgtagtc gggtaaaaaa aatatataaa tatatttgag   2760
aagtacacag tttcctctca gatgttgtac agaatcaaac attgaacata agtatatat    2820
catatgaact gtattagttg actagctgct tgggaaaatt ttggttacgc aataatcaat   2880
cttttatatg tatcagattt taattaaagt atttaaaata caagtgttgc tgtataaaat   2940
gatgttttga aacatttta aagtatttaa gttatatgtt ttaatttaag caacccagtt    3000
attttttatg ttatgcttat gggaatttta ttttatataa aatacatttt ttttctttcg   3060
agataggtgt aaatttaaac ttgaattttt tccaaaggca tttgtctaat ttattaaata   3120
atatatgatt tattatatat attttttatt aatccaataa atacttataa g            3171
```

<210> SEQ ID NO 9
<211> LENGTH: 15780
<212> TYPE: DNA
<213> ORGANISM: Artificial Sequence
<220> FEATURE:
<223> OTHER INFORMATION: Description of artificial sequence note = synthetic construct

<400> SEQUENCE: 9

```
caacttccta acgacgaggt agttcttgga tatgtaatac gggagagcca tccacttctt      60
tcactggtct gctaagtaga gaggatggcc gacagcgaag gaggatccga gcaggacgat     120
gtttcgttcc tgaggacgga ggatatggtg tgcctatcat gcacagcaac tggagagaga     180
gtttgcttag cagctgaggg cttttggtaac cgtcactgtt ttctagaaaa tattgctgat     240
aagaatatac caccagatct ttcaacatgt gtatttgtta ttgaacaagc tctatcagta     300
agagcacttc aggagttagt tacagcagct ggatctgaag agggaaaggg aactggatct     360
ggtcacagga ctcttcttta tggaaatgct atactactcc ggcaccaaaa cagtgacatg     420
tatctggctt gtttatctac cagttcatca aatgacaagc tctcatttga tgttggttta     480
caagaacatt cccaagggga agcttgttgg tggaccgtac accctgcttc taaacagaga     540
tcagaaggtg aaaagtgag agttggtgat gatttaattc ttgtgtctgt agccactgaa     600
agatatttgc atactgctaa agaaaacgat caatctattg taaatgcatc tttccatgta     660
actcattggt ctgttcagcc ttatggaact ggtatcagca aatgaagta tgttggttat     720
gtgttcggag gagatgtgtt aagattttc catggtgggg atgaatgcct taccattcca     780
tcaacttgga gtgaaacccc tggacaaaat gtggtagttt atgaaggagg gagtgttttg     840
agtcaagctc gttcactttg gagattgaa ctggctagga caaaatggtc tggtggtttc     900
attaattggt atcatccaat gaggatacga catctcacca ctggtagata cttaggagtt     960
aatgaaaata tgaattaca cctcgttgtt agggaggaag ccacaacagc attatctaca    1020
ttcattttaa gacaagaaaa agatgaccaa aaagtagtaa tggaagataa ggatttagaa    1080
gtaataggag ctccaataat aaaatatggt gacagtactg ttttagtcca acattcagaa    1140
agtggtttat ggttaactta taagtcattc gaaactaaga aaaaggtgt gggtaaagta    1200
gaagaaaaac aagctgtact tcatgaggag ggaaaaatgg atgatggatt agactttagt    1260
agaagtcaag aagaagaatc aaggactgct agagtaataa ggaaatgttc gtcacttttc    1320
actcaattta ttaggggtct agaaactctg caaatgaatc gaagcattc tctgttttgc    1380
gctagtgtaa atttaaatga aatggtcatg tgtttagaag atttaattaa ttactttgcc    1440
cagcctgagg aagatatgga acatgaggaa aaacaaaacc ggttaagagc tttgagaaac    1500
agacaagatt tgttccaaga agaaggaatt ttaaatctta tcttagaagc cattgataaa    1560
attaatgtta taacatccca aggtttctta gtcagtttag ctggagatga gtctggacag    1620
agctgggata taatctcagg atatttgtat caactgctag ctgccatcat aaaaggaaat    1680
catactaatt gtgctcagtt tgctaacaca aatagattaa actggttatt tagcagacta    1740
ggttctcaag cttcaagtga gggcacaggt atgttggatg tacttcattg cgtcttaatt    1800
gattctccag aagctttgaa tatgatgaga atgaacata aaaagtaat catttcactg    1860
ctagaaaaac atgggcgaga tccaagagtt ttagatgtac tttgttcact ttgtgttggt    1920
aatggtgtag cagtccgtag ctcacaaaac aacatctgtg atttccttct gccaggaaaa    1980
aacttgcttc tacaaacgca acttgtggat catgttgcca gtgtcaggcc aaatatttt    2040
```

```
gtgggtcgag tcgaaggttc tgctgtttat caaaaatggt attttgaagt gactttagat    2100
catatggagc aaaccaccca tatgacaccg catctaagaa ttggctgggc taacacttct    2160
ggttatgttc cctttcctgg cggtggtgaa aaatggggcg taatggagt tggtgatgat     2220 ctctactctt ttggttttga tggagctgca ttatggacag gtggaagaaa aactgtagtc    2280
cttcctcatg ctatggaacc ttacataaga aagggagatg ttattggttg tgctttcgat    2340
ctgactgttc caattattac atttactttt aatggaacat taatccgagg atcatttagg    2400
gattttaatc ttcaaggaat gttctttcca gttataagct gttcctcaaa acttagttgt    2460
cgttttttac tgggaggtga tcatggaaga ttaaaatatg cacctcctga agaattttct    2520
cctctcgttg aaagtttgct tcctcaacaa gtgctttcta ttgatccatg ttttatttt    2580 ggcaacctga ataaatgtgt attggctggt ccttatcctg ttgaagatga ttgtgctttt    2640
gttccagttc cagttgacac atctatggta aatttacccg ttcatgttga tacaatacgc    2700
gatcgtttag ctgaaaacat ccatgaaatg tgggctatga ataaaattga agcaggatgg    2760
atttatggag atgtaagaga tgatataaga agaatacatc catgtcttgt gcaatttgaa    2820
aaactacctc ctgcagaaaa gcgatatgac actcaacttg ctgtacaaac tttaaaaacc    2880
atcattgcac tgggctacca tataacaatg gaaaaaccac catctagaat aaagaacatt    2940
cgtttgccga atgaaccatt tttacaatct aatggttaca agccagctcc tcttgatctc    3000
agtgccataa cactaatacc taaaatggag gaacttgttg accaactcgc tgaaaatact    3060
cacaacttgt gggcaaaaga aagaatccaa caaggctgga cctatggtct taatgaggat    3120
cctgatttgt cccgaagtcc tcacctcgtc ccttacagta aagttgatga tttaattaaa    3180
aaagccaaca gggataccgc aagtgaaact gtcaggactc ttcttgttta tggttataat    3240
ttagaccctc ctacaggtga acaaactgaa gctctcttag cagaagcaag ccgtttgaag    3300
cagatgcagt ttagaaccta tcgggctgaa aagacatatg cagtaaccag tgcaaatgg    3360 tattttgaat ttgaaattct tactgctggg ccaatgagag taggttgggc cattgctgat    3420
tataatccag gttcccagat cggaagtgat gaagcatcct gggcatatga tggttataat    3480
gaggaaaagg tttattctgg ggttgctgaa acgtttggaa gacaatggca agttggagac    3540
gttgtaggag ttttcttga tctattggat catactatta gtttctctct aaatggtgaa    3600
ctgcttatgc atgcacttgg gggagaaaca tcttttgcag atgttcaggg agaaggattt    3660
gttccagcat ttacacttgg agtaggacaa aaagcaaaat tagtgtttgg gcaagatgtt    3720
aactcactta agttctttac tacctgtggt ttgcaagaag gttatgaacc tttctgtgta    3780
aacatgaaca gggcagttac cttttggtac accaaagatc atcctatatt tgaaaatact    3840
gatgattata ttgatactaa aattgatgca acgcgtattc ctgctggttc tgacacacca    3900
ccatgtctta aaattagtca taatactttt gagacaatgg agaaagccaa ttgggaattt    3960
cttagacttt ctttacctgt tcaatgttta ccatcattca taatgaacaa agaaaaagta    4020
cgtaggtggc aagaaataag gataagacaa cacagacttc ttgtggaagc tgaccaaacc    4080
actcctgctc acattgaaca gattatgaag tctggttttta gtatgagtga tattaagggt    4140
cttcaaagaa gttatacaga agatggaatg gaaggagaag aaggattggc accaagctca    4200
tcaccactta caaggactaa gtcaaaagtg actccagctc gtccacctag gaaaggctcc    4260
ttaccacgaa atggagatgt tattaatatg aacgggacat agaaccagg tggaggaaaa    4320 atgaaccgtt ctaatagtga gcttgatttc caacgtttca atggtgaaat gcccgatggc    4380
```

```
gataacaaga aaaagcgtgg gagatctcca tttaggttct tttcaagaaa aaggggggag      4440
cgtgatacta gtggagaaaa tgcaaaaaat gtacatatgt ctgagcctat gggtaatttc      4500
cttgagcctc caaggactcc aatgcagcaa agaggtggaa gtgctctgcg ttcttctcct      4560
caacctaaag tacaggagtt aactaagcca ccatccccat tagttgaaag aagtggaccc      4620
aaagcaatgt ctgtgcctgt tggaactggc atcgaaacta ttggaaatga aatatttgat      4680
gtagagtgtt tgaaattgat taatgaatac ttctacggtg tcaggatatt tccaggtcaa      4740
gacccaactc atgtatatgt cggttgggtt acaactcaat tccatctacg tagtaaagac      4800
tttaatcaga atcgagtgct aaagagcact gtagtagtat gtgatgaatt caatcgtgta      4860
atagacagta ttcagcggca gagttgtttt atggtaagag ctgatgaatt atacaatcaa      4920
gtaactcagg atgcctctgg taaaggtgct tcacaaggaa tgtttattgg atgtttcctg      4980
gatactgcta ctggttatgt gacgttcaca tgtgaaggaa agaaaactaa ccacaagtat      5040
aagatggaac ctgatacaaa attatttcca gctatatttg ttgaagctac aagcaaagaa      5100
attctacaaa ttgagcttgg tcgtacatca actacactgc ctttatcagc agctgttctc      5160
caaaattcag aaagacatgt cattcctcag tttccaccaa gacttaaagt tcagtgtcta      5220
aaaccacatc agtgggcacg tgttcctaat atttcattgc atgtccacgc tctgaaatta      5280
tcagatataa gaggttggag tatgctttgt gaagatccag tttcaatgtt agcattacat      5340
atacctgaag aagatagatg tattgatatt ttagaactta ttgaaatgga caaactactt      5400
tcattccatg ctcatacatt gacactttat gcagcactat gttaccaatc caattatcgt      5460
gcaggacatg ttctctgcaa acatgtagac caaaagcaac ttcagtatgc tattaggtct      5520
gaattcatat ctggatcttt acgcttggga ttttatgacc tcttgattgc tttacacatt      5580
gaatcacatg caacaacaat ggaagtttgt aaaaatgaat tcataatacc ccttggtcta      5640
gacttgaaag atttatatga agatccagat atgaagcaca gcttacgatc tttaaaaact      5700
gtctctattt tacctcaaat gagtatgaca gacattacgg aaaatattga aagcatcaat      5760
acattatata gtccttattt tcctcttgat gcagttaagg attatggaat gactgcatta      5820
gaagaggctg taagcatgaa tcaacttcac aatagagacc ctgtaggtgg ttcaaatgaa      5880
aacttgtttc taccccttgtt gaaactggta gatagattat tgcttgttgg gatactacga      5940
gatgaagatg ttacaaagct actaattatg tttgatcctg aaacttggga ttcaaatttt      6000
gaaaaggatg gcaaagatga acatcgtaag ggtttacttc aaatgaaaat ggcagagggg      6060
gcaaaactac agatgtgcta tctcttacag catttatgcg atatacaatt gcggcatcgg      6120
gttgaagcca ttattaattt tagttatgac tatattgctg atcttcagca ggatcagttg      6180
agaagatatg ttgatattaa gcagtctgat cttccatcat cagttgctgc aagaaaaaca      6240
agagagtttc gttgccctcc aagagaacag atgaatgcta tcataaattt taaaaattta      6300
gaagaagatg acaagaaaaa ctgtccatgt ggtgaagaac tgagggagag attaaacaca      6360
tttcatgaag aaactatgag taaagtttca cttgttgctc tccaagagcc acaagaagat      6420
gagaacggtg aaacaccaga aaagccgggt gttttcaaaa aattatacaa ttttattaat      6480
gctgttaaag aattggaaga acctcctaaa atagaagaag aacctgttaa gaaaactcct      6540
gaagaaatat ttagaaaagt attaattagt acaattgtta gatgggctga agaatcccag      6600
attgaaacac caaaattagt cagagaaatg ttcagtctat tggtaaggca gtacgacact      6660
gtaggtgaat taatcagatc tcttggaaac acttatgtga taaatgacaa aacgaaagaa      6720
gatgtagctc agatgtgggt agggttgagc cagatcagag ctctcctacc tgttcaaatg      6780
```

```
tctcaagatg aagaaggtct tatgcgaatg aggctatgga aattagttaa caatcacaca    6840
ttctttcaac atcctgattt gattagagtt cttcgtgttc atgaaaatgt tatggctgtt    6900
atgatcaata ccttgggtag aagatcacaa gcacaatctg atgcttctca agctggtcaa    6960
gaaggtgaac ctgcagctaa ggagaaagat acgtcccatg aaatggtggt agcatgttgt    7020
cgtttcctgt gttattttg cagaacttca cgtcaaaatc agaaagcaat gtttgaccat    7080
ttaacatttt tattagaaaa cagtaatatt ttactttcaa gaccttcact tagaggaagt    7140
acccctcttg atgttgccta ttcctctctc atggaaaata ccgaactggc attagctctt    7200
agagaacatt atttagagaa gatagctgtt tacttgtctc gctgtggatt acaatctaat    7260
tcagaattgg tagaaaaggg ttaccctgat ttgggttggg atccagttga gggagaaaga    7320
tatttagact ttttacgctt ctgtgtttgg gttaacggtg aaagtgttga agaaaatgca    7380
aatctggtta tacggctcct tatacgtcga ccagaatgtt tgggtcctgc acttcgtgga    7440
gaaggtgaag gattactgag agcaattata gatgctaata gatgtctga aagaatttca    7500 gatcgcagaa aaatgatgga ggaacctgaa aattctgccc atcatcagtt tgaacatcca    7560
cttcctgagt ctgatgaaga tgaggactat attgatacag gagcagcaat actggcattc    7620
tattgtactc tggtcgatct tttaggtcgc tgtgctccag atgctagtgt gattgctcag    7680
ggaaagaatg agtctcttag agctagagct attttgagat ctttagtacc tcttgaagat    7740
ttatttggtg tcttgagttt aaagtttaca cttaccaatc cagctattgg agaagaaagg    7800
ccaaaaagtg atataccatc tggtctaata ccatctcata agcaaagtat tgttttattt    7860
ttagagagag tatatggtat tgaacagcaa gatctcttct tcagattact cgaggaagca    7920
tttttacctg atttaagagc agcaactatg ctagatagaa ctgatggttc tgaatcagaa    7980
atggcattag ctatgaatcg ctatattgga aattctattc tcccttttgtt gataaagcat    8040 taccagtttt atagtggtgc agataactat gcaagtcttt tagatgctac acttcataca    8100
gtgtatcgcc tatcaaaaaa tcgaatgcta actaaaggtc agcgagaggc agtatcagat    8160 ttttggttg ctctcacaag tcaattacag ccaagcatgt tactcaaact tcttcgaaag    8220
ttaaccgttg atgtatcaaa gctttctgag tataccacag ttgctttaag gttgcttact    8280
ttacactatg agcgttgtgc aaaatattat ggaactactg gtggacaagc tggtggatct    8340
agtgatgaag aaaaaaggct cactatgtta ctcttcagta atattttga ttctttatca    8400 aaaatggatt atgatcctga attatttgga aaagcgcttc cctgcttgag tgctatagga    8460
tgtgcacttc cacccgatta ttcactgtcc aagaattatg atgaagaatg gtatagttca    8520
aagggttcag aaccgactga tgggccttat aatccactgc ccatcaatac ttctatggtt    8580
tctctaaata atgatttaaa cacaattgtt caaaaatttt ctgaacatta tcatgatgca    8640
tgggctagtc gaaaaatgga aaatggttgg gtatatggtg agcagtggtc tgacagctct    8700
aaaactcatc ctcgttttaaa accttataca ttgcttaatg attatgaaaa agagagatac    8760
aaagaaccgg ttagagagtc attgaaagct ctgttagcta taggatggaa tgtagagcat    8820
actgaagttg atattccttc taataacaga ggatcatcag tcagaagatc ttctaaagca    8880
aatacatctg atggttcaac accatttaat tatcatccca acccaattga tatgactaat    8940
ttaacattga gtagagaaat gcaaaatatg gcagagaggt tagctgaaaa ctcacatgat    9000
atttgggcaa aaagaagaa agaagaactt gtttcatgtg gtggtggtat acacccacag    9060
cttgttccat atgatctttt aacagacaaa gagaagagga aagatagaga aagatctcaa    9120
```

-continued

```
gaatttttga aatatttaca atatcaagga tacaaactcc acaggcctac tcgaggaagt    9180
gctgatgagc aacaggccgc tgcagctgct gccacaggag agtccagatt tgcttacagt    9240
ctactcgaga aacttataca atatactgat aaagcttcta ttaatatgaa actactaaag    9300
ccttctggta cattcagtag acgctccagt tttaaaactt gttcaagaga cataaaattc    9360
ttttccaaag tggtattgct attggttgag aagtatttca gcactcacag aaattacttc    9420
attgctgttg ccactgcttc taataatgta ggagcagcct cttaaaaga aaagaaatg     9480 gttgccagtt tgttctgtaa gctggcaaat ttaattcgaa caaagctggc tgcttttggt    9540
gcagatgttc gaattactgt ccgttgtcta caagtgctag tgaaagctat agatgccaag    9600
tcattggtaa agaattgtcc tgaatttata aggacttcaa tgctgacatt tttcaataat    9660
acagctgatg acttaggcca aactattcag tgtttgcaag agggtcgtta cagtcacctt    9720
agaggcactc atcttaaaac atctacttct ttattttata taaatgatgt tgtactacct    9780
gttctcactt ctatgtttga tcatttggct gtgtgtgatt atggtagcga cttgttactt    9840
gatgaaattc aagtggcctc atatagaatg ttgggtagtt tatataattt aggaattgat    9900
ccaactttaa ctcatgacag aaaatattta aaaacagaaa ttgaaaggca taggcctgcc    9960
attggtgctt gtcttggtgc attttcatca acatttccag tcgcttatct tgaacccccat   10020 ttaaataaac ataatcagtt ttcattagtt aatagaattg ctgaacattc tcttgaagca   10080
caggatattc tagctagaat ggaaaacacc atgcctacat tggatgcgat ccttctgaa    10140 gttgatcagt tcattgaatc cgaaaagagt catacttcag caccacatgt tattgatgtg   10200
attttgcctc tgctttgtgc ttatttgcca agttggtgga gtcaaggtcc tgataatgtc   10260
agtctcacag cagggaatta tgtaacaatg gttactagtg atcatatgaa tcaactccta   10320
aaaaatgtac taaaattaat caaaaataat attggaaatg aaaatgctcc ctggatgacg   10380
agaatagcag cttacaccca gcagatcatc ataaactctt ctgaagaact gttgaaagat   10440
ccattccttc cattaacaca agttgttaag aagaggatag acaatatgtt tcaccgtgaa   10500
gaatctcttc gaggatttct aaaatcttca actgaagata cctctcaagt tgaagcagaa   10560
attcaggagg gctggcatct tattgttaga gatatatatt cttttttatcc actactaatt   10620 aaatatgttg atttacaaag aaatcactgg ttacgtaata atattccgga agctgaatac   10680
ttgtatactc atgttgctga tatatttaat atttggtcta aatcacagta ctttctaaaa   10740
gaagaacaga atttcatatc tgccaacgaa atagacaata tggctctaat tatgcccact   10800
gcaactagga gatctgcagt tgttttggat ggaacagctc ctgctggagg tggaaagaag   10860 aaaagaagc atcgtgataa gaaaagagat aagaataaag aaatccaagc aagcttaatg   10920
gtagcttgct taaacgtttt attaccagtt ggtcttaacc tattcgctgg aagagaacaa   10980
gagttagttc agcattgtaa agacagatat ttgaagaaaa tgccagaata tgaaatagtg   11040
gattttgcca aaatccaatt aactcttcct gacaagatag atcctggaga tgagatgtct   11100
tggcagcatt atttgtactc aaaactggga aataaaaaag atatcagctc tgaaaaacca   11160
cagcaaatcg atgaggtagt tgataggatt gtggctatgg caaaagttct ttttgggctt   11220
catatgattg atcatccaca actacagagc aagacacaat acagatctgt tgtatccaca   11280
cagagaaagc gtgctgtcat agcttgtttc cggcaactat cactacatgc cttaccaagc   11340
atgcaaataa acctccacct caccaatctg atggaaaag agttcttttca gcagcgagaa   11400 aacgggctgc tattgcttgt cttagaactc aaccttttgta tacccttcca aggcatcgag   11460
taattaacat atttgctcgc gcttattgtg agctgtggct gcaagaagag aatgttggtc   11520
```

```
aagaaatcat gattgaagat cttacacaaa cttttgaaga tgctgaattg aaaaaaagag    11580
attctgaaga agatgaaagc aaacctgatc cacttaccca attagttaca acattttgtc    11640
ggggtgcaat gactgaaagg agtggagctt tgcaagaaga cccactttat atgtcctatg    11700
cagaaattac tgcaaaatca tgtggagaag aagaagaaga aggtggagat gaggaagaag    11760
gtggagacga agaaggaggg gcatctatcc ataagacaat ggcaaaatta gtggaacaag    11820
aaatggaaaa acagaaactc ttattccatc aagctcggct agccaacaga ggtgttgcag    11880
aaatggtatt gttacatatt tcagcttgta aaggtgttcc cagtgaaatg ttatgaaaa     11940 ctctccagct gggtatttct gttttacgtg gtggtaatct tgatattcaa atgggtatgc    12000
taaatcattt gaaagaaaaa aaggatgttg gatttttttac ttctatagct ggcttgatga   12060
actcctgcag tgtgttggat ttagatgcat ttgaaagaaa cacaaaagct gaaggcttag    12120
gagttggttc agaaggtgct gctggtgaaa agaacatgca tgatgctgaa ttcacctgta    12180
ctcttttcag atttattcaa cttacctgtg aagggcataa cttagaatgg cagaattatc    12240
ttagaaccca agctggaaat acaacaacag ttaatgttgt tatttgtact gttgattacc    12300
ttttgagatt acaggaatca attatggact tctattggca ctattcgagt aaagaattaa    12360
ttgatcctgc tggaaaagcc aacttttttca aagcaattgg tgtggctagt caagtattta    12420
atacactctc tgaagtaatt caaggcgctt gcccacaaaa tcaacaagct ctggctcatt    12480
caagattgtg ggatgctgtt ggaggatttt tgtttctttt ctctcatatg caagataagc    12540
tatcaaaaca ttctagtcaa gtagacttac tgaaagaact tttgaattta cagaaagata    12600
tgataacaat gatgctatca atgttggaag gtaatgttgt gaatggtact attggaaaac    12660
agatggtaga cacattagtt gaatctgcct caaatgtgga attgattttg aagtacttcg    12720
acatgttttt gaaattgaaa gatttgacat cctctgctag cttcttggaa cttgatccaa    12780
accatgaagg ctgggtaaca cctaaagatt ttaaagaaaa aatggaacag cagaaaagtt    12840
atactccaga agaaatagac ttcatgttac agtgctgtga aaccaatcat gacggtaaaa    12900
ttgactatgt tggcttcacg gatagattcc atgagccggc caaggaaatt ggttttaacc    12960
tagctgttct tctcacaaat ttatctgagc atatgccaaa tgaaccgaga cttgctcgct    13020
ttttagaaac agctggtagt gttcttaact actttgaacc tttcctggga cgaattgaaa    13080
tattaggtag tagtaaacga atcgagcgtg tatatttcga gattaaagaa tcaaatattg    13140
aacagtggga aaaacctcaa atcaaggaat ctaaacgagc attttttctat tcaattgtca    13200 ctgaaggagg tgacaaagaa aaattggaag cttttgttaa tttttgtgaa gatgccatat    13260
ttgagatgac acatgccagt gggcttatgg caactgatga tggtacaggc tctggaggag    13320
gaaaacaaag agcatcctct tattcttata tggaagatga agatgaagaa aggaatccaa    13380
tcagacgtgg ttggcaagca actaaagatg gaatttactt tatgttctca atgttatctc    13440
ctagcaatat taaacataaa attattgaaa tgcaacaaat gtcaattatt gaactaatga    13500
ttggttttat aaaactattt ttctacatgt tttattactc aggatattct gtatcagttg    13560
tactgaagta tattggtggt attatatttt cattgatgag gggaccacaa attgaagagc    13620
cagttgtaga agttaaagag gaagaaaaat ctggacctct gaggataatg cctgctttgc    13680
caccacctga agatagctct ctgcttccat ctgatgggtc aagagacatg aaaaaagaag    13740
acagtcagcc tccatcaaaa gtcatagaag gggctattcc catagaagaa ggaggtgaga    13800
ggagctcaga ggaacatgcg ggagaccatg taaaaccaga aaatgaagag caacctccaa    13860
```

```
caccaacact tgctgatata ttgggtggag aagcagcaag aaaagaagca gcacaaagag    13920
cagaagtcgc tgctgaacaa gaagcagtta tggctgcttt tgaggcagaa tctaaaatag    13980
aaaaagtttc agagccttct gctgtctctc aaattgattt taacaagtat actcaccggg    14040
ctgtcagttt ccttgctcgt aatttctata atcttaaata tgtagcattg gttttggctt    14100
tctgcattaa ctttatttta ttgttctaca aggtaacaac attgggtgaa gatgatgatg    14160
ctgctagcgg agaagggagt gttgaacaac taatggaaga attaacaggc gaaggtgatg    14220
atgtgagtgg cggaggaagt agtggtggag aaagtggtga agaggatcca attgaaatgg    14280
ttcatgtgga tgaggatttc ttttatatgg cacatgttat gcgattggct gcaatcctac    14340
attctcttgt ttcttttagct atgttgattg catattatca tttgaaggtc cctctagcta    14400
tattcaagag agaaaaagaa atagctcgtc gacttgagtt tgatggtttg tacattgctg    14460
agcaaccaga agatgatgat attaaatcac attgggataa actggttatc tgtgcaaaat    14520
catttcctgt taattactgg gataaatttg tgaagaaaaa ggttcgacag aaatacagtg    14580
aaacttatga ctttgattca ataagtaatc ttttgggaat ggaaaaaaca tctttcagtg    14640
cccaagatac tgaagaagga tcgggactta ttcattacat tttgaacttt gactggaggt    14700
atcagctttg gaaagcagga gtcacaatca cagataatgc attttttgtac agtttattat    14760 acttcatctt ttcaattttg ggaaacttca ataacttttt ctttgctgcc catttacttg    14820
atgttgcagt tggttttaaa acattgagga ctattttgca atcagtcaca cacaatggaa    14880
aacagcttgt attgactgta atgctgctaa ccatcatagt atacatctat actgtcattg    14940
ctttcaactt cttccgaaaa ttttatgtcc aagaagagga tgaggaagtg gataaaaaat    15000
gccacgatat gttaacttgt tttgtattcc acctttacaa aggagttaga gctggtggtg    15060
gtattggtga tgagattgaa cctcctgatg gtgatgatta tgaagtttac aggataatgt    15120
ttgatattac gttttttcttt tttgttattg tcatcttgct agccatcatt caaggtttga    15180
tcattgatgc atttggtgaa ttgagagatc agttagaaag tgtaaaagaa gacatggaat    15240
ctaactgctt catttgtggg ataggaaaag attattttga taaagttccc catggttttg    15300
acactcatgt tcaacaagaa cataacttgg ctaattacat gttctttctt atgcatctga    15360
ttaacaagcc agatactgaa tacacaggtc aagaaaccta tgtctggaac atgtatcagc    15420
aacgttgttg ggatttcttc ccagttggtg actgttttcg taaacagtat gaagatgaac    15480
tgggaggtgg tggtggttaa ttcatttggg tgggtggtgg ctaaatttat attattaaaa    15540
caaaattaat gctgggaact atcaaacatc cttcaatttt attaaaattt cagctaaatt    15600
caacaatata tcttatgata ttgtatttgt ctaatgaagg aatagaacta tcgtgttatg    15660
aatcagtgaa gttttcactt gtttagcata atttatgcta agtttactat tgcaaaatac    15720
tttctttata tccgaaaatg ttgtaaaata aatgtaaatg gtgtggcctt aaatataatg    15780
```

<210> SEQ ID NO 10
<211> LENGTH: 965
<212> TYPE: DNA
<213> ORGANISM: Artificial Sequence
<220> FEATURE:
<223> OTHER INFORMATION: Description of artificial sequence note =
      synthetic construct

<400> SEQUENCE: 10

```
aatttagaat caaatattat tgatactatt tcttttttcat actttacatt aatattcttc      60
aaaattaaaa atgccaggag tagagcatgt tactaacaaa gtcgttgttc atcctttagt     120
```

```
tctattaagt gttgttgatc atttcaatag aatgggtaaa attgggaatc agaagagagt    180
agttggcgta ttattaggat gctggaaggc aaaaggtgtt ttagacgtat ctaatagttt    240
tgcagtgcca tttgatgaag atgataaaga caaatcagtt tggttttag accatgatta     300 tttagaaaat atgtatggca tgtttaagaa agttaatgca agagaaaaag ttgttggctg    360
gtatcataca ggcccaaagt tacatcaaaa tgatgttgca attaatgaac ttatacgccg    420
ttactgccct aactcagttc ttgttattat cgatgcaaaa ccaaaggatc ttggtttacc    480
tacagaagca tatagagcag ttgaagaagt acatgatgat ggttctccta cgacaaaaac    540
atttgagcat gttcccagtg aaataggggc tgaagaagca gaggaagtgg gtgttgaaca    600
tctgctgaga gatataaaag atacaactgt cggctcactt tcgcaaaggg ttactaatca    660
atttcttggt ctcaaaggcc ttaatcaaca aattcaagac atcagggatt accttatgca    720
ggttgttgaa ggaaaattgc ccatcaacca tcaaataata tatcagcttc aagacatatt    780
taatctcctt cctgacatga accatgggaa ctttgttgat tcattataca taaaaacaaa    840
tgatcagatg cttgtcgttt atctcgctgc cctcgttaga gctattgttg ccttgcataa    900
tctgatcaat aataaactca gtaatcgtga tgccgaaaaa aaaaaaaaa  aaaaaaaaa     960 aaaaa                                                                965
```

<210> SEQ ID NO 11
<211> LENGTH: 924
<212> TYPE: DNA
<213> ORGANISM: Artificial Sequence
<220> FEATURE:
<223> OTHER INFORMATION: Description of artificial sequence note = synthetic construct

<400> SEQUENCE: 11

```
tacttcattg tcataaaggg gtaacattgc tgaatccagc gtaaaggtta cagtgactct     60
cacctggtta taacagtttt gctttgtaat catgggttct gagagatata gcttttcttt    120
gactactttc agtccatctg gaaaattagt tcaaattgag tatgcacttg ccgcagtcgc    180
agctggagct ccatcaatcg gtatcagagc atccaatgga gttgtattgg ctactgaaaa    240
caaatacaaa tcaatttttat atgaagaaca tactattcaa aaagtagaaa tgataactaa    300
acacattgga atggtctaca gtggaatggg acctgattat aggctactag tgaagagagc    360
tagaaaaatg gctcaacaat aacagttagt ttacggtgag cctattccta ctgcacagct    420
tgttcaacga gttgccatgg ttatgcagga gtacactcaa tctggaggtg ttagaccttt    480 tggagttttct ttactcattg ccgggtggga tggggataaa ccatctctgt ttcaatgtga    540
tccatctgga gcatactttg cctggaaagc tactgcaatg ggaaaaaatt ttgtcactgg    600
caaaacattt ctagaaaaga ggtacagtga aactttagag ctggatgatg cagtacatac    660
tgcaattctc actcttaaag aaaactttga aggccaaatg acttcggaca atatcgaggt    720
cggagtttgt gatgatcaag ggttcagagt tttagatcct acaacagtga aggattatct    780
ggctaatatt ccataaattt attattaaaa tttgatttta taattaataa aaaggtgatt    840
gcttatggat atgtgtgatg cctaaataaa atattatttt ttattggttt aatgctaaaa    900
aaaaaaaaaa aaaaaaaaa  aaaa                                           924
```

<210> SEQ ID NO 12
<211> LENGTH: 946
<212> TYPE: DNA
<213> ORGANISM: Artificial Sequence
<220> FEATURE:

<223> OTHER INFORMATION: Description of artificial sequence note = synthetic construct

<400> SEQUENCE: 12

| | | | | | |
|---|---|---|---|---|---|
| atcattgatg | atggttgaga | aagttccaga | ctctacatat | gaaatggttg | gaggtcttga | 60 |
| taagcaaatt | aaggaaatca | aagaagtaat | tgaacctcct | gtaaaacatc | agaactgtt | 120 |
| tgatgcacta | ggaatagctc | agcccaaagg | agttttatta | tatggaccac | ctggaacagg | 180 |
| taaaacactt | ttggcaagag | cagttgccca | tcacactgag | tgcacgttca | ttcgtgtgtc | 240 |
| aggatctgag | ttggttcaga | aattcattgg | ggaaggatcc | agaatggtta | gagaattgtt | 300 |
| cgtcatggca | agggaacatg | ctccatctat | catatttatg | gatgaaatcg | attcaatagg | 360 |
| ttcatcacgt | atcgaatctg | ggagtggtgg | tgattctgaa | gtccagagaa | caatgttaga | 420 |
| gttattgaac | caattggatg | gcttcgaagc | cacaaaaaat | attaaggtca | taatggccac | 480 |
| taataggatt | gatattttgg | accctgctct | tctgcgtcct | ggaaggatag | atcgtaagat | 540 |
| tgagttcccc | ccaccaaatg | aggaagctcg | tttagatatc | cttagaattc | attcacgtaa | 600 |
| aatgaatctt | acccggggta | tcaacttgcg | taaaattgcc | gagctcatgc | ctggagcttc | 660 |
| aggtgcagaa | gtaaagggtg | tctgtactga | agcaggatg | tatgccctga | gggagaggag | 720 |
| aatccatgtc | acccaagaag | atttcgaaat | ggctgtggcc | aaggttatgc | aaaaggactc | 780 |
| cgagaagaat | atgtcaatca | agaaattatg | gaaataaacg | actcacttat | tttttttttt | 840 |
| ttttactctg | tttaaaaagc | tttaaatata | tagatgtttg | tgaggttttg | ttaaaaataa | 900 |
| atatatacta | taatcataaa | aaaaaaaaaa | aaaaaaaaaa | aaaaaa | | 946 |

<210> SEQ ID NO 13
<211> LENGTH: 21
<212> TYPE: DNA
<213> ORGANISM: Artificial Sequence
<220> FEATURE:
<223> OTHER INFORMATION: Description of artificial sequence note = synthetic construct

<400> SEQUENCE: 13
caactttgta tagaaaagtt g                                          21

<210> SEQ ID NO 14
<211> LENGTH: 21
<212> TYPE: DNA
<213> ORGANISM: Artificial Sequence
<220> FEATURE:
<223> OTHER INFORMATION: Description of artificial sequence note = synthetic construct

<400> SEQUENCE: 14
caactttgta taataaagtt g                                          21

<210> SEQ ID NO 15
<211> LENGTH: 4855
<212> TYPE: DNA
<213> ORGANISM: Artificial Sequence
<220> FEATURE:
<223> OTHER INFORMATION: Description of artificial sequence note = synthetic construct

<400> SEQUENCE: 15

| | | | | | |
|---|---|---|---|---|---|
| agattatcaa | aaaggatctt | cacctagatc | cttttaaatt | aaaaatgaag | ttttaaatca | 60 |
| atctaaagta | tatatgagta | aacttggtct | gacagttacc | aatgcttaat | cagtgaggca | 120 |
| cctatctcag | cgatctgtct | atttcgttca | tccatagttg | cctgactccc | cgtcgtgtag | 180 |

```
ataactacga tacgggaggg cttaccatct ggcccagtg ctgcaatgat accgcgagac      240
ccacgctcac cggctccaga tttatcagca ataaaccagc cagccggaag ggccgagcgc      300
agaagtggtc ctgcaacttt atccgcctcc atccagtcta ttaattgttg ccgggaagct      360
agagtaagta gttcgccagt taatagtttg cgcaacgttg ttgccattgc tacaggcatc      420
gtggtgtcac gctcgtcgtt tggtatggct tcattcagct ccggttccca acgatcaagg      480
cgagttacat gatcccccat gttgtgcaaa aaagcggtta gctccttcgg tcctccgatc      540
gttgtcagaa gtaagttggc cgcagtgtta tcactcatgg ttatggcagc acttacggat      600
ggcatgacag taagagaatt atgcagatgc ttttctgtga ctggtgagta ctcaaccaag      660
tcattctgag aatagtgtat gcggcgaccg agttgctctt gcccggcgtc aatacgggat      720
aataccgcgc cacatagcag aactttaaaa gtgctcatca ttggaaaacg ttcttcgggg      780
cgaaaactct caaggatctt accgctgttg agatccagtt cgatgtaacc cactcgtgca      840
cccaactgat cttcagcatc ttttactttc accagcgttt ctgggtgagc aaaaacagga      900
aggcaaaatg ccgcaaaaaa gggaataagg gcgacacgga aatgttgaat actcatactc      960 ttccttttc aatattattg aagcatttat cagggttatt gtctcatgat gatatatttt     1020
tatcttgtgc aatgtaacat cagagatttt gagacacggg ccagagctgc aggaaacag     1080 ctatgaccat gtaatacgac tcactatagg ggatatcgcg gccgccctgc agctggatgg     1140
caaataatga ttttattttg actgatagtg acctgttcgt tgcaacaaat tgataagcaa     1200
tgctttctta taatgccaac tttgtataga aagttgaac gagaaacgta aaatgatata     1260
aatatcaata tattaaatta gattttgcat aaaaaacaga ctacataata ctgtaaaaca     1320
caacatatcc agtcactatg aatcaactac ttagatggta ttagtgacct gtagtcgact     1380
aagttggcag catcacccga cgcactttgc gccgaataaa tacctgtgac ggaagatcac     1440
ttcgcagaat aaataaatcc tggtgtccct gttgataccg ggaagccctg gccaactt     1500 tggcgaaaat gagacgttga tcggcacgta agaggttcca actttcacca taatgaaata     1560
agatcactac cgggcgtatt ttttgagtta tcgagatttt caggagctaa ggaagctaaa     1620
atggagaaaa aaatcactgg atataccacc gttgatatat cccaatggca tcgtaaagaa     1680
cattttgagg catttcagtc agttgctcaa tgtacctata accagaccgt tcagctggat     1740
attacggcct ttttaaagac cgtaaagaaa aataagcaca gtttttatcc ggcctttatt     1800
cacattcttg cccgcctgat gaatgctcat ccggaattcc gtatggcaat gaaagacggt     1860
gagctggtga tatgggatag tgttcaccct tgttacaccg ttttccatga gcaaactgaa     1920
acgttttcat cgctctggag tgaataccac gacgatttcc ggcagtttct acacatatat     1980
tcgcaagatg tggcgtgtta cggtgaaaac ctggcctatt tccctaaagg gtttattgag     2040
aatatgtttt tcgtctcagc caatccctgg gtgagtttca ccagttttga tttaaacgtg     2100
gccaatatgg acaacttctt cgccccgtt ttcaccatgg gcaaatatta tacgcaaggc     2160
gacaaggtgc tgatgccgct ggcgattcag gttcatcatg ccgtttgtga tggcttccat     2220
gtcggcagaa tgcttaatga attacaacag tactgcgatg agtggcaggg ggggcgtaaa     2280
cgccgcgtgg atccggctta ctaaaagcca gataacagta tgcgtatttg cgcgctgatt     2340
tttgcggtat aagaatatat actgatatgt atacccgaag tatgtcaaaa agaggtatgc     2400
tatgaagcag cgtattacag tgacagttga cagcgacagc tatcagttgc tcaaggcata     2460
tatgatgtca atatctccgg tctggtaagc acaaccatgc agaatgaagc ccgtcgtctg     2520
```

```
cgtgccgaac gctggaaagc ggaaaatcag gaagggatgg ctgaggtcgc ccggtttatt   2580
gaaatgaacg gctcttttgc tgacgagaac aggggctggt gaaatgcagt ttaaggttta   2640
cacctataaa agagagagcc gttatcgtct gtttgtggat gtacagagtg atattattga   2700
cacgcccggg cgacggatgg tgatcccccct ggccagtgca cgtctgctgt cagataaagt   2760
ctcccgtgaa ctttacccgg tggtgcatat cggggatgaa agctggcgca tgatgaccac   2820
cgatatggcc agtgtgccgg tctccgttat cggggaagaa gtggctgatc tcagccaccg   2880
cgaaaatgac atcaaaaacg ccattaacct gatgttctgg ggaatataaa tgtcaggctc   2940
ccttatacac agccagtctg caggtcgata cagtagaaat tacagaaact ttatcacgtt   3000
tagtaagtat agaggctgaa atccagatg aagccgaacg acttgtaaga gaaaagtata   3060
agagttgtga aattgttctt gatgcagatg attttcagga ctatgacact agcgtatatg   3120
aataggtaga tgttttatt ttgtcacaca aaaaagaggc tcgcacctct ttttcttatt   3180
tcttttatg atttaatacg gcattgagga caatagcgag taggctggat acgacgattc   3240
cgtttgagaa gaacatttgg aaggctgtcg gtcgactaag ttggcagcat cacccgaaga   3300
acatttggaa ggctgtcggt cgactacagg tcactaatac catctaagta gttgattcat   3360
agtgactgga tatgttgtgt tttacagtat tatgtagtct gttttttatg caaaatctaa   3420
tttaatatat tgatatttat atcatttac gtttctcgtt caactttatt atacaaagtt   3480
ggcattataa aaaagcattg ctcatcaatt tgttgcaacg aacaggtcac tatcagtcaa   3540
aataaaatca ttatttgggg cccgagctta agactggccg tcgttttaca acgtcgtgac   3600
tgggaaaaca tccatgctag cgttaacgcg agagtaggga actgccaggc atcaaataaa   3660
acgaaaggct cagtcggaag actgggcctt tcgttttatc tgttgtttgt cggtgaacgc   3720
tctcctgagt aggacaaatc cgccgggagc ggatttgaac gttgtgaagc aacgcccgg   3780
agggtggcgg gcaggacgcc cgccataaac tgccaggcat caaactaagc agaaggccat   3840
cctgacggat ggccttttg cgtttctaca aactcttcct ggctagcggt acgcgtatta   3900
attgcgttgc gctcactgcc cgctttccag tcgggaaacc tgtcgtgcca gctgcattaa   3960
tgaatcggcc aacgcgcggg gagaggcggt ttgcgtattg ggcgctcttc cgcttcctcg   4020
ctcactgact cgctgcgctc ggtcgttcgg ctgcggcgag cggtatcagc tcactcaaag   4080
gcggtaatac ggttatccac agaatcaggg gataacgcag gaaagaacat gtgagcaaaa   4140
ggccagcaaa aggccaggaa ccgtaaaaag gccgcgttgc tggcgttttt ccataggctc   4200
cgcccccctg acgagcatca caaaaatcga cgctcaagtc agaggtggcg aaacccgaca   4260
ggactataaa gataccaggc gtttccccct ggaagctccc tcgtgcgctc tcctgttccg   4320
accctgccgc ttaccggata cctgtccgcc tttctccctt cgggaagcgt ggcgctttct   4380
catagctcac gctgtaggta tctcagttcg gtgtaggtcg ttcgctccaa gctgggctgt   4440
gtgcacgaac cccccgttca gcccgaccgc tgcgccttat ccggtaacta tcgtcttgag   4500
tccaacccgg taagacacga cttatcgcca ctggcagcag ccactggtaa caggattagc   4560
agagcgaggt atgtaggcgg tgctacagag ttcttgaagt ggtggcctaa ctacggctac   4620
actagaagaa cagtatttgg tatctgcgct ctgctgaagc cagttacctt cggaaaaaga   4680
gttggtagct cttgatccgg caaacaaacc accgctggta gcggtggttt ttttgtttgc   4740
aagcagcaga ttacgcgcag aaaaaaagga tctcaagaag atcctttgat cttttctacg   4800
gggtctgacg ctcagtggaa cgacgcgtaa ctcacgttaa gggattttgg tcatg         4855
```

-continued

```
<210> SEQ ID NO 16
<211> LENGTH: 11321
<212> TYPE: DNA
<213> ORGANISM: Artificial Sequence
<220> FEATURE:
<223> OTHER INFORMATION: Description of artificial sequence note =
      synthetic construct
<220> FEATURE:
<221> NAME/KEY: misc_feature
<222> LOCATION: (6511)..(6511)
<223> OTHER INFORMATION: n is a, c, g, or t

<400> SEQUENCE: 16
cgtaccggcc ggcctctgcc tgcgttctgc tgtggaagtt cctattccga agttcctatt      60
ctccagaaag tataggaact tcacatgctg cctcgtgcaa gtcacgatct cgagttctat     120
agtgtcacct aaatcgtatg tgtatgatac ataaggttat gtattaattg tagccgcgtt     180
ctaacgacaa tatgtccata tggtgcactc tcagtacaat ctgctctgat gccgcatagt     240
taagccagcc ccgacacccg ccaacacccg ctgacgcgcc ctgacgggct tgtctgctcc     300
cggcatccgc ttacagacaa gctgtgaccg tctccgggag ctgcatgtgt cagaggtttt     360
caccgtcatc accgaaacgc gcgagacgaa agggcctcgt gatacgccta tttttatagg     420
ttaatgtcat gaccaaaatc ccttaacgtg agttttcgtt ccactgagcg tcagaccccg     480
tagaaaagat caaaggatct tcttgagatc cttttttct gcgcgtaatc tgctgcttgc      540
aaacaaaaaa accaccgcta ccagcggtgg tttgtttgcc ggatcaagag ctaccaactc     600 ttttccgaa ggtaactggc ttcagcagag cgcagatacc aaatactgtc cttctagtgt      660
agccgtagtt aggccaccac ttcaagaact ctgtagcacc gcctacatac ctcgctctgc     720
taatcctgtt accagtggct gctgccagtg gcgataagtc gtgtcttacc gggttggact     780
caagacgata gttaccggat aaggcgcagc ggtcgggctg aacggggggt tcgtgcacac     840
agcccagctt ggagcgaacg acctacaccg aactgagata cctacagcgt gagcattgag     900
aaagcgccac gcttcccgaa gggagaaagg cggacaggta tccggtaagc ggcagggtcg     960
gaacaggaga gcgcacgagg gagcttccag ggggaaacgc ctggtatctt tatagtcctg    1020
tcgggtttcg ccacctctga cttgagcgtc gatttttgtg atgctcgtca gggggggcgga    1080 gcctatggaa aaacgccagc aacgcggcct ttttacggtt cctggccttt tgctggcctt    1140
ttgctcacat gttctttcct gcgttatccc ctgattctgt ggataaccgt attaccgcct    1200
ttgagtgagc tgataccgct cgccgcagcc gaacgaccga gcgcagcgag tcagtgagcg    1260
aggaagcgga agagcgccca atacgcaaac cgcctctccc cgcgcgttgg ccgattcatt    1320
aatgcaggtt gatcagatct cgatcccgcg aaattaatac gactcactat agggagacca    1380
caacggtttc cctctagaaa taattttgtt taactttaag aaggagatat acccatggaa    1440
aagcctgaac tcaccgcgac gtctgtcgag aagtttctga tcgaaaagtt cgacagcgtc    1500
tccgacctga tgcagctctc ggagggcgaa gaatctcgtg ctttcagctt cgatgtagga    1560
gggcgtggat atgtcctgcg ggtaaatagc tgcgccgatg gtttctacaa agatcgttat    1620
gtttatcggc actttgcatc ggccgcgctc ccgattccgg aagtgcttga cattggggaa    1680
ttcagcgaga gcctgaccta ttgcatctcc cgccgtgcac agggtgtcac gttgcaagac    1740
ctgcctgaaa ccgaactgcc cgctgttctg cagccggtcg cggaggctat ggatgcgatc    1800
gctgcggccg atcttagcca dacgagcggg ttcggcccat tcggaccgca aggaatcggt    1860
caatacacta catggcgtga tttcatatgc gcgattgctg atccccatgt gtatcactgg    1920
caaactgtga tggacgacac cgtcagtgcg tccgtcgcgc aggctctcga tgagctgatg    1980
```

```
ctttgggccg aggactgccc cgaagtccgg cacctcgtgc acgcggattt cggctccaac    2040
aatgtcctga cggacaatgg ccgcataaca gcggtcattg actggagcga ggcgatgttc    2100
ggggattccc aatacgaggt cgccaacatc ttcttctgga ggccgtggtt ggcttgtatg    2160
gagcagcaga cgcgctactt cgagcggagg catccggagc ttgcaggatc gccgcggctc    2220
cgggcgtata tgctccgcat tggtcttgac caactctatc agagcttggt tgacggcaat    2280
ttcgatgatg cagcttgggc gcagggtcga tgcgacgcaa tcgtccgatc cggagccggg    2340
actgtcgggc gtacacaaat cgcccgcaga agcgcggccg tctggaccga tggctgtgta    2400
gaagtactcg ccgatagtgg aaaccgacgc cccagcactc gtccgagggc aaaggaatag    2460
tgaggtacag cttggatcga tccggctgct aacaaagccc gaaaggaagc tgagttggct    2520
gctgccaccg ctgagcaata actagcataa ccccttgggg cctctaaacg ggtcttgagg    2580
ggttttttgc tgaaaggagg aactatatcc ggatgatcgt cgaggcctca cgtgttaaca    2640
gaagttccta ttccgaagtt cctattctct agaaagtata ggaacttcca ccacacaaca    2700
caatggcggc caccgcttcc agaaccaccc gattctcttc ttcctcttca cccccacct    2760
tccccaaacg cattactaga tccacctcc ctctctctca tcaaaccctc accaaaccca    2820
accacgctct caaaatcaaa tgttccatct ccaaaccccc cacggcggcg cccttcacca    2880
aggaagcgcc gaccacggag cccttcgtgt cacggttcgc ctccggcgaa cctcgcaagg    2940
gcgcggacat ccttgtggag gcgctggaga ggcagggcgt gacgacggtg ttcgcgtacc    3000
ccggcggtgc gtcgatggag atccaccagg cgctcacgcg ctccgccgcc atccgcaacg    3060
tgctcccgcg ccacgagcag ggcggcgtct tcgccgccga aggctacgcg cgttcctccg    3120
gcctccccgg cgtctgcatt gccacctccg gccccggcgc caccaacctc gtgagcggcc    3180
tcgccgacgc tttaatggac agcgtcccag tcgtcgccat caccggccag gtcagccgcc    3240
ggatgatcgg caccgacgcc ttccaagaaa ccccgatcgt ggaggtgagc agatccatca    3300
cgaagcacaa ctacctcatc ctcgacgtcg acgacatccc ccgcgtcgtc gccgaggctt    3360
tcttcgtcgc cacctccggc cgccccggtc cggtcctcat cgacattccc aaagacgttc    3420
agcagcaact cgccgtgcct aattgggacg agcccgttaa cctccccggt tacctcgcca    3480
ggctgcccag gccccccgcc gaggcccaat tggaacacat tgtcagactc atcatggagg    3540
cccaaaagcc cgttctctac gtcggcggtg gcagtttgaa ttccagtgct gaattgaggc    3600
gctttgttga actcactggt attcccgttg ctagcacttt aatgggtctt ggaactttc    3660
ctattggtga tgaatattcc cttcagatgc tgggtatgca tggtactgtt tatgctaact    3720
atgctgttga caatagtgat ttgttgcttg cctttgggt aaggtttgat gaccgtgtta    3780
ctgggaagct tgaggctttt gctagtaggg ctaagattgt tcacattgat attgattctg    3840
ccgagattgg gaagaacaag caggcgcacg tgtcggtttg cgcggatttg aagttggcct    3900
tgaagggaat taatatgatt ttggaggaga aggagtgga gggtaagttt gatcttggag    3960
gttggagaga agagattaat gtgcagaaac acaagtttcc attgggttac aagacattcc    4020
aggacgcgat ttctccgcag catgctatcg aggttcttga tgagttgact aatggagatg    4080
ctattgttag tactgggggtt gggcagcatc aaatgtgggc tgcgcagttt tacaagtaca    4140
agagaccgag gcagtggttg acctcagggg gtcttggagc catgggtttt ggattgcctg    4200
cggctattgg tgctgctgtt gctaaccctg ggctgttgt ggttgacatt gatggggatg    4260
gtagtttcat catgaatgtt caggagttgg ccactataag agtggagaat ctcccagtta    4320
```

```
agatattgtt gttgaacaat cagcatttgg gtatggtggt tcagtgggag gataggttct    4380
acaagtccaa tagagctcac acctatcttg gagatccgtc tagcgagagc gagatattcc    4440
caaacatgct caagtttgct gatgcttgtg ggataccggc agcgcgagtg acgaagaagg    4500
aagagcttag agcggcaatt cagagaatgt tggacacccc tggcccctac cttcttgatg    4560
tcattgtgcc ccatcaggag catgtgttgc cgatgattcc cagtaatgga tccttcaagg    4620
atgtgataac tgagggtgat ggtagaacga ggtactgatt gcctagacca aatgttcctt    4680
gatgcttgtt ttgtacaata tatataagat aatgctgtcc tagttgcagg atttggcctg    4740
tggtgagcat catagtctgt agtagttttg gtagcaagac attttatttt ccttttattt    4800
aacttactac atgcagtagc atctatctat ctctgtagtc tgatatctcc tgttgtctgt    4860
attgtgccgt tggattttt gctgtagtga gactgaaaat gatgtgctag taataatatt    4920
tctgttagaa atcaagtag agaatctgtt gaagaagtca aaagctaatg gaatcaggtt    4980
acatattcaa tgttttctt tttttagcgg ttggtagacg tgtagattca acttctcttg    5040
gagctcacct aggcaatcag taaaatgcat attccttttt taacttgcca tttatttact    5100
tttagtggaa attgtgacca atttgttcat gtagaacgga tttggaccat tgcgtccaca    5160
aaacgtctct tttgctcgat cttcacaaag cgataccgaa atccagagat agttttcaaa    5220
agtcagaaat ggcaaagtta taaatagtaa aacagaatag atgctgtaat cgacttcaat    5280
aacaagtggc atcacgtttc tagttctaga cccatcagct gaggtacacc ggtgatcctc    5340
gaagagaagg gttaataaca cactttttta acatttttaa cacaaatttt agttatttaa    5400
aaatttatta aaaatttaa ataagaaga ggaactcttt aaataaatct aacttacaaa    5460
atttatgatt tttaataagt tttcaccaat aaaaaatgtc ataaaaatat gttaaaaagt    5520
atattatcaa tattctcttt atgataaata aaagaaaaa aaaataaaa gttaagtgaa    5580
aatgagattg aagtgacttt aggtgtgtat aaatatatca accccgccaa caatttattt    5640
aatccaaata tattgaagta tattattcca tagcctttat ttatttatat atttattata    5700
taaaagcttt atttgttcta ggttgttcat gaaatatttt tttggtttta tctccgttgt    5760
aagaaaatca tgtgctttgt gtcgccactc actattgcag cttttcatg cattggtcag    5820
attgacggtt gattgtattt ttgttttta tggttttgtg ttatgactta agtcttcatc    5880
tcttatctc ttcatcaggt ttgatggtta cctaatatgg tccatgggta catgcatggt    5940
taaattaggt ggccaacttt gttgtgaacg atagaatttt tttttatatt aagtaaacta    6000
ttttatatt atgaaataat aataaaaaaa atatttatc attattaaca aaatcatatt    6060
agttaatttg ttaactctat aataaaagaa atactgtaac attcacatta catggtaaca    6120
tcttccacc ctttcatttg ttttttgttt gatgactttt tttcttgttt aaatttattt    6180
cccttctttt aaatttggaa tacattatca tcatatataa actaaaatac taaaaacagg    6240
attacacaaa tgataaataa taacacaaat atttataaat ctagctgcaa tatatttaaa    6300
ctagctatat cgatattgta aaataaaact agctgcattg atactgataa aaaaatatca    6360
tgtgctttct ggactgatga tgcagtatac ttttgacatt gcctttattt tattttcag    6420
aaaagctttc ttagttctgg gttcttcatt atttgtttcc catctccatt gtgaattgaa    6480
tcatttgctt cgtgtcacaa atacatttag ntaggtacat gcattggtca gattcacggt    6540
ttattatgtc atgacttaag ttcatggtag tacattacct gccacgcatg cattatattg    6600
gttagatttg ataggcaaat ttggttgtca acaatataaa tataaataat gttttatat    6660
tacgaaataa cagtgatcaa aacaaacagt tttatctttta ttaacaagat tttgttttg    6720
```

```
tttgatgacg ttttttaatg tttacgcttt cccccttctt ttgaatttag aacactttat    6780
catcataaaa tcaaatacta aaaaaattac atatttcata ataataaca caaatatttt    6840 taaaaaatct gaaataataa tgaacaatat tacatattat cacgaaaatt cattaataaa    6900
aatattatat aaataaaatg taatagtagt tatatgtagg aaaaaagtac tgcacgcata    6960
atatatacaa aaagattaaa atgaactatt ataaataata acactaaatt aatggtgaat    7020
catatcaaaa taatgaaaaa gtaaataaaa tttgtaatta acttctatat gtattacaca    7080
cacaaataat aaataatagt aaaaaaaatt atgataaata tttaccatct cataaagata    7140
tttaaaataa tgataaaaat atagattatt ttttatgcaa ctagctagcc aaaaagagaa    7200
cacgggtata tataaaaaga gtacctttaa attctactgt acttccttta ttcctgacgt    7260
ttttatatca agtggacata cgtgaagatt ttaattatca gtctaaatat ttcattagca    7320
cttaatactt ttctgtttta ttcctatcct ataagtagtc ccgattctcc caacattgct    7380
tattcacaca actaactaag aaagtcttcc atagcccccc aagccctagg cgctatcaac    7440
tttgtataga aaagttgaac gagaaacgta aaatgatata aatatcaata tattaaatta    7500
gattttgcat aaaaaacaga ctacataata ctgtaaaaca caacatatcc agtcactatg    7560
gtcgacattt tcaggagcta aggaagctaa aatggagaaa aaaatcactg gatataccac    7620
cgttgatata tcccaatggc atcgtaaaga acattttgag gcatttcagt cagttgctca    7680
atgtacctat aaccagaccg ttcagctgga tattacggcc ttttttaaga ccgtaaagaa    7740
aaataagcac aagttttatc cggcctttat tcacattctt gcccgcctga tgaatgctca    7800
tccggaattc cgtatggcaa tgaaagacgg tgagctggtg atatgggata gtgttcaccc    7860
ttgttacacc gttttccatg agcaaactga acgttttca tcgctctgga gtgaatacca    7920
cgacgatttc cggcagtttc tacacatata ttcgcaagat gtggcgtgtt acggtgaaaa    7980
cctggcctat ttccctaaag ggtttattga gaatatgttt ttcgtctcag ccaatccctg    8040
ggtgagtttc accagttttg atttaaacgt ggccaatatg gacaacttct tcgcccccgt    8100
tttcaccatg ggcaaatatt atacgcaagg cgacaaggtg ctgatgccgc tggcgattca    8160
ggttcatcat gccgtctgtg atggcttcca tgtcggcaga atgcttaatg aattacaaca    8220
gtactgcgat gagtggcagg gcggggcgta aacgcgtgga tccggcttac taaaagccag    8280
ataacagtat gcgtatttgc gcgctgattt ttgcggtata agaatatata ctgatatgta    8340
tacccgaagt atgtcaaaaa gaggtgtgct atgaagcagc gtattacagt gacagttgac    8400
agcgacagct atcagttgct caaggcatat atgatgtcaa tatctccggt ctggtaagca    8460
caaccatgca gaatgaagcc cgtcgtctgc gtgccgaacg ctggaaagcg gaaaatcagg    8520
aagggatggc tgaggtcgcc cggtttattg aaatgaacgg ctcttttgct gacgagaaca    8580
gggactggtg aaatgcagtt taaggtttac acctataaaa gagagagccg ttatcgtctg    8640
tttgtggatg tacagagtga tattattgac acgccagggc gacggatggt gatcccctg    8700 gccagtgcac gtctgctgtc agataaagtc tcccgtgaac tttacccggt ggtgcatatc    8760
ggggatgaaa gctggcgcat gatgaccacc gatatggcca gtgtgccggt ctccgttatc    8820
ggggaagaag tggctgatct cagccaccgc gaaaatgaca tcaaaaacgc cattaacctg    8880
atgttctggg gaatataaat gtcaggctcc cttatacaca ggcggccgcc atagtgactg    8940
gatatgttgt gttttacagt attatgtagt ctgtttttta tgcaaaatct aatttaatat    9000
attgatattt atatcatttt acgtttctcg ttcaacttta ttatacaaag ttgatagata    9060
```

```
tcggtccgag atccatcagg taagtttctg cttctacctt tgatatatat ataataatta    9120
tcattaatta gtagtaatat aatatttcaa atattttttt caaaataaaa gaatgtagta    9180
tatagcaatt gcttttctgt agtttataag tgtgtatatt ttaatttata acttttctaa    9240
tatatgacca aacatggtg atgtgcaggt ccatggtgga gctcgaccga tatctatcaa     9300
ctttgtataa taaagttgaa cgagaaacgt aaaatgatat aaatatcaat atattaaatt   9360
agattttgca taaaaacag actacataat actgtaaaac acaacatatc cagtcactat    9420
ggcggccgca ttagggcacc ccaggcttta cactttatgc ttccggctcg tataatgtgt   9480
ggattttgag ttaggatccg tcgagatttt caggagctaa ggaagctaaa atggagaaaa   9540
aaatcactgg atataccacc gttgatatat cccaatggca tcgtaaagaa catttttgagg  9600
catttcagtc agttgctcaa tgtacctata accagaccgt tcagctggat attacggcct   9660
ttttaaagac cgtaaagaaa aataagcaca agttttatcc ggcctttatt cacattcttg   9720
cccgcctgat gaatgctcat ccggaattcc gtatggcaat gaaagacggt gagctggtga   9780
tatgggatag tgttcaccct tgttacaccg ttttccatga gcaaactgaa acgttttcat   9840
cgctctggag tgaataccac gacgatttcc ggcagtttct acacatatat tcgcaagatg   9900
tggcgtgtta cggtgaaaac ctggcctatt tccctaaagg gtttattgag aatatgtttt   9960
tcgtctcagc caatccctgg gtgagtttca ccagttttga tttaaacgtg gccaatatgg  10020
acaacttctt cgcccccgtt ttcaccatgg gcaaatatta tacgcaaggc gacaaggtgc   10080
tgatgccgct ggcgattcag gttcatcatg ccgtttgtga tggcttccat gtcggcagaa   10140
tgcttaatga attacaacag tactgcgatg agtggcaggc ggggcgtaat ctagaggatc   10200
cggcttacta aaagccagat aacagtatgc gtatttgcgc gctgattttt gcggtataag   10260
aatatatact gatatgtata cccgaagtat gtcaaaaaga ggtatgctat gaagcagcgt   10320
attacagtga cagttgacag cgacagctat cagttgctca aggcatatat gatgtcaata   10380
tctccggttc ggtaagcaca accatgcaga atgaagcccg tcgtctgcgt gccgaacgct   10440
ggaaagcgga aaatcaggaa gggatggctg aggtcgcccg gtttattgaa atgaacggct   10500
cttttgccga cgagaacagg ggctggtgaa atgcagttta aggtttacac ctataaaaga   10560
gagagccgtt atcgtctgtt tgtggatgta cagagtgata ttattgacac gccagggcga   10620
cggatggtga tcccctggc cagtgcacgt ctgctgtcag ataaagtccc ccgtgaactt    10680
tacccggtgg tgcatatcgg ggatgaaagc tggcgcatga tgaccaccga tatggccagt   10740
gtgccggtct ccgttatcgg ggaagaagtg gctgatctca gccaccgcga aaatgacatc   10800
aaaaacgcca ttaacctgat gttctgggga atataaatgt caggctccct tatacacagc   10860
cagtctgcag gtcgaccata tgactggat atgttgtgtt ttacagtatt atgtagtctg   10920
tttttatgc aaaatctaat ttaatatatt gatatttata tcattttacg tttctcgttc    10980
aacttttcta tacaaagttg atagcgttaa cccgggtaac tgtacctaaa gaaggagtgc   11040
gtcgaagcag atcgttcaaa catttggcaa taaagtttct taagattgaa tcctgttgcc   11100
ggtcttgcga tgattatcat ataatttctg ttgaattacg ttaagcatgt aataattaac   11160
atgtaatgca tgacgttatt tatgagatgg gttttttatga ttagagtccc gcaattatac   11220
atttaatacg cgatagaaaa caaaatatag cgcgcaaact aggataaatt atcgcgcgcg  11280
gtgtcatcta tgttactaga tcgatgtcga atcgatgggc c                       11321
```

<210> SEQ ID NO 17
<211> LENGTH: 8851

<212> TYPE: DNA
<213> ORGANISM: Artificial Sequence
<220> FEATURE:
<223> OTHER INFORMATION: Description of artificial sequence note = synthetic construct
<220> FEATURE:
<221> NAME/KEY: misc_feature
<222> LOCATION: (6841)..(6841)
<223> OTHER INFORMATION: n is a, c, g, or t

<400> SEQUENCE: 17

```
acaaagttga tagcgttaac ccgggtaact gtacctaaag aaggagtgcg tcgaagcaga      60
tcgttcaaac atttggcaat aaagtttctt aagattgaat cctgttgccg gtcttgcgat     120
gattatcata taatttctgt tgaattacgt taagcatgta ataattaaca tgtaatgcat     180
gacgttattt atgagatggg ttttatgat tagagtcccg caattataca tttaatacgc      240
gatagaaaac aaaatatagc gcgcaaacta ggataaatta tcgcgcgcgg tgtcatctat     300
gttactagat cgatgtcgaa tcgatgggcc cgtaccggcc ggcctctgcc tgcgttctgc     360
tgtggaagtt cctattccga agttcctatt ctccagaaag tataggaact tcacatgctg     420
cctcgtgcaa gtcacgatct cgagttctat agtgtcacct aaatcgtatg tgtatgatac     480
ataaggttat gtattaattg tagccgcgtt ctaacgacaa tatgtccata tggtgcactc     540
tcagtacaat ctgctctgat gccgcatagt taagccagcc ccgacacccg ccaacacccg     600
ctgacgcgcc ctgacgggct tgtctgctcc cggcatccgc ttacagacaa gctgtgaccg     660
tctccgggag ctgcatgtgt cagaggtttt caccgtcatc accgaaacgc gcgagacgaa     720
agggcctcgt gatacgccta tttttatagg ttaatgtcat gaccaaaatc ccttaacgtg     780
agttttcgtt ccactgagcg tcagaccccg tagaaaagat caaaggatct tcttgagatc     840
cttttttct gcgcgtaatc tgctgcttgc aaacaaaaaa accaccgcta ccagcggtgg      900
tttgtttgcc ggatcaagag ctaccaactc tttttccgaa ggtaactggc ttcagcagag     960
cgcagatacc aaatactgtc cttctagtgt agccgtagtt aggccaccac ttcaagaact    1020
ctgtagcacc gcctacatac ctcgctctgc taatcctgtt accagtggct gctgccagtg    1080
gcgataagtc gtgtcttacc gggttggact caagacgata gttaccggat aaggcgcagc    1140
ggtcgggctg aacggggggt tcgtgcacac agcccagctt ggagcgaacg acctacaccg    1200
aactgagata cctacagcgt gagcattgag aaagcgccac gcttcccgaa gggagaaagg    1260
cggacaggta tccggtaagc ggcagggtcg gaacaggaga gcgcacgagg gagcttccag    1320
ggggaaacgc ctggtatctt tatagtcctg tcgggtttcg ccacctctga cttgagcgtc    1380
gatttttgtg atgctcgtca ggggggcgga gcctatggaa aaacgccagc aacgcggcct    1440
ttttacggtt cctggccttt tgctggcctt tgctcacat gttctttcct gcgttatccc     1500
ctgattctgt ggataaccgt attaccgcct ttgagtgagc tgataccgct cgccgcagcc    1560
gaacgaccga gcgcagcgag tcagtgagcg aggaagcgga agagcgccca atacgcaaac    1620
cgcctctccc cgcgcgttgg ccgattcatt aatgcaggtt gatcagatct cgatcccgcg    1680
aaattaatac gactcactat agggagacca caacggtttc cctctagaaa taattttgtt    1740
taactttaag aaggagatat acccatggaa aagcctgaac tcaccgcgac gtctgtcgag    1800
aagtttctga tcgaaaagtt cgacagcgtc tccgacctga tgcagctctc ggagggcgaa    1860
gaatctcgtg ctttcagctt cgatgtagga gggcgtggat atgtcctgcg ggtaaatagc    1920
tgcgccgatg gtttctacaa agatcgttat gtttatcggc actttgcatc ggccgcgctc    1980
ccgattccgg aagtgcttga cattggggaa ttcagcgaga gcctgaccta ttgcatctcc    2040
```

```
cgccgtgcac agggtgtcac gttgcaagac ctgcctgaaa ccgaactgcc cgctgttctg    2100
cagccggtcg cggaggctat ggatgcgatc gctgcggccg atcttagcca gacgagcggg    2160
ttcggcccat tcggaccgca aggaatcggt caatacacta catggcgtga tttcatatgc    2220
gcgattgctg atccccatgt gtatcactgg caaactgtga tggacgacac cgtcagtgcg    2280
tccgtcgcgc aggctctcga tgagctgatg ctttgggccg aggactgccc cgaagtccgg    2340
cacctcgtgc acgcggattt cggctccaac aatgtcctga cggacaatgg ccgcataaca    2400
gcggtcattg actggagcga ggcgatgttc ggggattccc aatacgaggt cgccaacatc    2460
ttcttctgga ggccgtggtt ggcttgtatg agcagcaga cgcgctactt cgagcggagg    2520
catccggagc ttgcaggatc gccgcggctc cgggcgtata tgctccgcat tggtcttgac    2580
caactctatc agagcttggt tgacggcaat ttcgatgatg cagcttgggc gcagggtcga    2640
tgcgacgcaa tcgtccgatc cggagccggg actgtcgggc gtacacaaat cgcccgcaga    2700
agcgcggccg tctggaccga tggctgtgta gaagtactcg ccgatagtgg aaaccgacgc    2760
cccagcactc gtccgagggc aaaggaatag tgaggtacag cttggatcga tccggctgct    2820
aacaaagccc gaaaggaagc tgagttggct gctgccaccg ctgagcaata actagcataa    2880
ccccttgggg cctctaaacg ggtcttgagg ggttttttgc tgaaaggagg aactatatcc    2940
ggatgatcgt cgaggcctca cgtgttaaca gaagttccta ttccgaagtt cctattctct    3000
agaaagtata ggaacttcca ccacacaaca caatggcggc caccgcttcc agaaccaccc    3060
gattctcttc ttcctcttca cccccacctt tccccaaacg cattactaga tccaccctcc    3120
ctctctctca tcaaaccctc accaaaccca accacgctct caaaatcaaa tgttccatct    3180
ccaaaccccc cacggcggcg cccttcacca aggaagcgcc gaccacgagc ccttcgtgt    3240 cacggttcgc ctccggcgaa cctcgcaagg gcgcggacat ccttgtggag gcgctggaga    3300
ggcagggcgt gacgacggtg ttcgcgtacc ccggcggtgc gtcgatggag atccaccagg    3360
cgctcacgcg ctccgccgcc atccgcaacg tgctcccgcg ccacgagcag ggcggcgtct    3420
tcgccgccga aggctacgcg cgttcctccg gcctccccgg cgtctgcatt gccacctccg    3480
gccccggcgc caccaacctc gtgagcggcc tcgccgacgc tttaatggac agcgtcccag    3540
tcgtcgccat caccggccag gtcagccgcc ggatgatcgg caccgacgcc ttccagaaaa    3600
ccccgatcgt ggaggtgagc agatccatca cgaagcacaa ctacctcatc ctcgacgtcg    3660
acgacatccc ccgcgtcgtc gccgaggctt tcttcgtcgc cacctccggc cgccccggtc    3720
cggtcctcat cgacattccc aaagacgttc agcagcaact cgccgtgcct aattgggacg    3780
agcccgttaa cctccccggt tacctcgcca ggctgcccag gccccccgcc gaggcccaat    3840
tggaacacat tgtcagactc atcatggagg cccaaaagcc cgttctctac gtcggcggtg    3900
gcagtttgaa ttccagtgct gaattgaggc gctttgttga actcactggt attcccgttg    3960
ctagcacttt aatgggtctt ggaactttc ctattggtga tgaatattcc cttcagatgc    4020
tgggtatgca tggtactgtt tatgctaact atgctgttga caatagtgat tgttgcttg    4080 cctttggggt aaggtttgat gaccgtgtta ctgggaagct tgaggctttt gctagtaggg    4140
ctaagattgt tcacattgat attgattctg ccgagattgg gaagaacaag caggcgcacg    4200
tgtcggtttg cgcggatttg aagttggcct tgaagggaat taatatgatt ttggaggaga    4260
aaggagtgga gggtaagttt gatcttggag gttggagaga agagattaat gtgcagaaac    4320
acaagtttcc attgggttac aagacattcc aggacgcgat ttctccgcag catgctatcg    4380
```

```
aggttcttga tgagttgact aatggagatg ctattgttag tactgggggtt gggcagcatc    4440 aaatgtgggc tgcgcagttt tacaagtaca agagaccgag gcagtggttg acctcagggg    4500
gtcttggagc catgggtttt ggattgcctg cggctattgg tgctgctgtt gctaaccctg    4560
gggctgttgt ggttgacatt gatggggatg gtagtttcat catgaatgtt caggagttgg    4620
ccactataag agtggagaat ctcccagtta agatattgtt gttgaacaat cagcatttgg    4680
gtatggtggt tcagtgggag gataggttct acaagtccaa tagagctcac acctatcttg    4740
gagatccgtc tagcgagagc gagatattcc caaacatgct caagtttgct gatgcttgtg    4800
ggataccggc agcgcgagtg acgaagaagg aagagcttag agcggcaatt cagagaatgt    4860
tggacacccc tggcccctac cttcttgatg tcattgtgcc ccatcaggag catgtgttgc    4920
cgatgattcc cagtaatgga tccttcaagg atgtgataac tgagggtgat ggtagaacga    4980
ggtactgatt gcctagacca aatgttcctt gatgcttgtt ttgtacaata tatataagat    5040
aatgctgtcc tagttgcagg atttggcctg tggtgagcat catagtctgt agtagttttg    5100
gtagcaagac atttattttt ccttttattt aacttactac atgcagtagc atctatctat    5160
ctctgtagtc tgatatctcc tgttgtctgt attgtgccgt tggatttttt gctgtagtga    5220
gactgaaaat gatgtgctag taataatatt tctgttagaa atctaagtag agaatctgtt    5280
gaagaagtca aaagctaatg gaatcaggtt acatattcaa tgttttttctt tttttagcgg    5340 ttggtagacg tgtagattca acttctcttg gagctcacct aggcaatcag taaaatgcat    5400 attcctttt taacttgcca tttatttact tttagtggaa attgtgacca atttgttcat    5460
gtagaacgga tttggaccat tgcgtccaca aaacgtctct tttgctcgat cttcacaaag    5520
cgataccgaa atccagagat agttttcaaa agtcagaaat ggcaaagtta taaatagtaa    5580
aacagaatag atgctgtaat cgacttcaat aacaagtggc atcacgtttc tagttctaga    5640
cccatcagct gaggtacacc ggtgatcctc gaagagaagg gttaataaca cactttttta    5700 acattttaa cacaaattt agttatttaa aaatttatta aaaatttaa ataagaaga    5760 ggaactcttt aaataaatct aacttacaaa atttatgatt tttaataagt tttcaccaat    5820
aaaaaatgtc ataaaaatat gttaaaaagt atattatcaa tattctcttt atgataaata    5880
aaagaaaaaa aaaataaaa gttaagtgaa aatgagattg aagtgacttt aggtgtgtat    5940
aaatatatca accccgccaa caatttattt aatccaaata tattgaagta tattattcca    6000
tagcctttat ttatttatat atttattata taaaagcttt atttgttcta ggttgttcat    6060
gaaatatttt tttggtttta tctccgttgt aagaaaatca tgtgctttgt gtcgccactc    6120
actattgcag cttttttcatg cattggtcag attgacggtt gattgtattt ttgtttttta    6180
tggttttgtg ttatgactta agtcttcatc tctttatctc ttcatcaggt ttgatggtta    6240
cctaatatgg tccatgggta catgcatggt taaattaggt ggccaacttt gttgtgaacg    6300
atagaatttt tttttatatt aagtaaacta ttttttatatt atgaaataat aataaaaaaa    6360 atatttatc attattaaca aaatcatatt agttaatttg ttaactctat aataaaagaa    6420
atactgtaac attcacatta catggtaaca tcttttccacc ctttcatttg ttttttgttt    6480
gatgactttt tttcttgttt aaatttattt cccttctttt aaatttggaa tacattatca    6540
tcatatataa actaaaatac taaaaacagg attacacaaa tgataaataa taacacaaat    6600
atttataaat ctagctgcaa tatatttaaa ctagctatat cgatattgta aaataaaact    6660
agctgcattg atactgataa aaaaatatca tgtgctttct ggactgatga tgcagtatac    6720
ttttgacatt gcctttattt tattttttcag aaaagctttc ttagttctgg gttcttcatt    6780
```

```
atttgtttcc catctccatt gtgaattgaa tcatttgctt cgtgtcacaa atacatttag    6840
ntaggtacat gcattggtca gattcacggt ttattatgtc atgacttaag ttcatggtag    6900
tacattacct gccacgcatg cattatattg gttagatttg ataggcaaat ttggttgtca    6960
acaatataaa tataaataat gttttttatat tacgaaataa cagtgatcaa aacaaacagt   7020
tttatcttta ttaacaagat tttgtttttg tttgatgacg ttttttaatg tttacgcttt    7080
cccccttctt ttgaatttag aacactttat catcataaaa tcaaatacta aaaaattac    7140 atatttcata aataataaca caaatatttt taaaaaatct gaaataataa tgaacaatat   7200
tacatattat cacgaaaatt cattaataaa aatattatat aaataaaatg taatagtagt   7260
tatatgtagg aaaaaagtac tgcacgcata atatatacaa aaagattaaa atgaactatt   7320
ataaataata acactaaatt aatggtgaat catatcaaaa taatgaaaaa gtaaataaaa   7380
tttgtaatta acttctatat gtattacaca cacaaataat aaataatagt aaaaaaaatt   7440
atgataaata tttaccatct cataaagata tttaaaataa tgataaaaat atagattatt   7500
ttttatgcaa ctagctagcc aaaaagagaa cacgggtata tataaaaaga gtacctttaa   7560
attctactgt acttcctta ttcctgacgt ttttatatca agtggacata cgtgaagatt    7620
ttaattatca gtctaaatat ttcattagca cttaatactt ttctgtttta ttcctatcct   7680
ataagtagtc ccgattctcc caacattgct tattcacaca actaactaag aaagtcttcc   7740 atagccccc aagccctagg cgctatcaac tttgtataga aaagttgaag catcacttcg    7800
acatcttcaa gcatataatc ttcttcataa ccatcatctg agttagggat accggtcatt   7860
gggtcgcaat cctttacaac aaacctcaga gtagcagcaa agtttgtgac agtaagatta   7920
ggggcatctg gaaattgcag gcaatataa gtaggtgatg tttccgaaca ggctaatctt    7980
tggcagggga cctcagctac gatctggtaa ccttcgctca cttctaactg cactcgaact   8040
ttctccagta gctggtcact catggtattt gtacagtcaa actgaagaac aatatgattt   8100
ttgaaaacat gcttcgtgac tctaacttga tattctgtct cagattccgt aagactgata   8160
ggatcggaac caactttatt atacaaagtt gatagatatc ggtccgagat ccatcaggta   8220
agtttctgct tctacctttg atatatatat aataattatc attaattagt agtaatataa   8280
tatttcaaat attttttttca aaataaaaga atgtagtata tagcaattgc ttttctgtag   8340
tttataagtg tgtatatttt aatttataac ttttctaata tatgaccaaa acatggtgat   8400
gtgcaggtcc atggtggagc tcgaccgata tctatcaact ttgtataata aagttggttc   8460
cgatcctatc agtcttacgg aatctgagac agaatatcaa gttagagtca cgaagcatgt   8520
tttcaaaaat catattgttc ttcagtttga ctgtacaaat accatgagtg accagctact   8580
ggagaaagtt cgagtgcagt tagaagtgag cgaaggttac cagatcgtag ctgaggtccc   8640
ctgccaaaga ttagcctgtt cggaaacatc acctacttat attgccctgc aatttccaga   8700
tgcccctaat cttactgtca caaactttgc tgctactctg aggtttgttg taaaggattg   8760
cgacccaatg accggtatcc ctaactcaga tgatggttat gaagaagatt atatgcttga   8820
agatgtcgaa gtgatgcttc aacttttcta t                                  8851
```

<210> SEQ ID NO 18
<211> LENGTH: 15759
<212> TYPE: DNA
<213> ORGANISM: Artificial Sequence
<220> FEATURE:
<223> OTHER INFORMATION: Description of artificial sequence note = synthetic construct

<400> SEQUENCE: 18

```
caacttccta acgacgaggt agttcttgga tatgtaatac gggagagcca tccacttctt      60
tcactggtct gctaagtaga gaggatggcc gacagcgaag gaggatccga gcaggacgat     120
gtttcgttcc tgaggacgga ggatatggtg tgcctatcat gcacagcaac tggagagaga     180
gtttgcttag cagctgaggg ctttggtaac cgtcactgtt ttctagaaaa tattgctgat     240
aagaatatac caccagatct ttcaacatgt gtatttgtta ttgaacaagc tctatcagta     300
agagcacttc aggagttagt tacagcagct ggatctgaag agggaaaggg aactggatct     360
ggtcacagga ctcttctttta tggaaatgct atactactcc ggcaccaaaa cagtgacatg     420
tatctggctt gtttatctac cagttcatca aatgacaagc tctcatttga tgttggttta     480
caagaacatt cccaagggga agcttgttgg tggaccgtac accctgcttc taaacagaga     540
tcagaaggtg aaaaagtgag agttggtgat gatttaattc ttgtgtctgt agccactgaa     600
agatatttgc atactgctaa agaaaacgat caatctattg taaatgcatc tttccatgta     660
actcattggt ctgttcagcc ttatggaact ggtatcagca aaatgaagta tgttggttat     720
gtgttcggag gagatgtgtt aagatttttc catggtgggg atgaatgcct taccattcca     780
tcaacttgga gtgaaacccc tggacaaaat gtggtagttt atgaaggagg gagtgttttg     840
agtcaagctc gttcactttg gagattggaa ctggctagga caaaatggtc tggtggtttc     900
attaattggt atcatccaat gaggatacga catctcacca ctggtagata cttaggagtt     960
aatgaaaata tgaattaca cctcgttgtt agggaggaag ccacaacagc attatctaca    1020
ttcattttaa gacaagaaaa agatgaccaa aagtagtaa tggaagataa ggatttagaa    1080
gtaataggag ctccaataat aaaatatggt gacagtactg ttttagtcca acattcagaa    1140
agtggtttat ggttaactta taagtcattc gaaactaaga aaaaaggtgt gggtaaagta    1200
gaagaaaaac aagctgtact tcatgaggag ggaaaaatgg atgatggatt agactttagt    1260
agaagtcaag aagaagaatc aaggactgct agagtaataa ggaaatgttc gtcacttttc    1320
actcaattta ttaggggtct agaaactctg caaatgaatc gaagacattc tctgttttgc    1380
gctagtgtaa atttaaatga aatggtcatg tgtttagaag atttaattaa ttactttgcc    1440
cagcctgagg aagatatgga acatgaggaa aaacaaaacc ggttaagagc tttgagaaac    1500
agacaagatt tgttccaaga agaaggaatt ttaaatctta tcttagaagc cattgataaa    1560
attaatgtta taacatccca aggtttctta gtcagtttag ctggagatga gtctggacag    1620
agctgggata taatctcagg atatttgtat caactgctag ctgccatcat aaaaggaaat    1680
catactaatt gtgctcagtt tgctaacaca aatagattaa actggttatt tagcagacta    1740
ggttctcaag cttcaagtga gggcacaggt atgttggatg tacttcattg cgtcttaatt    1800
gattctccag aagctttgaa tatgatgaga gatgaacata taaaagtaat catttcactg    1860
ctagaaaaac atgggcgaga tccaagagtt ttagatgtac tttgttcact ttgtgttggt    1920
aatggtgtag cagtccgtag ctcacaaaac aacatctgtg atttccttct gccaggaaaa    1980
aacttgcttc tacaaacgca acttgtggat catgttgcca gtgtcaggcc aaatattttt    2040
gtgggtcgag tcgaaggttc tgctgtttat caaaaatggt attttgaagt gactttagat    2100
catatggagc aaaccacccca tatgacaccg catctaagaa ttggctgggc taacacttct    2160
ggttatgttc cctttcctgg cggtggtgaa aaatggggcg gtaatggagt tggtgatgat    2220
ctctactctt ttggttttga tggagctgca ttatggacag gtggaagaaa aactgtagtc    2280
```

```
cttcctcatg ctatggaacc ttacataaga aagggagatg ttattggttg tgctttcgat    2340
ctgactgttc caattattac atttactttt aatggaacat taatccgagg atcatttagg    2400
gattttaatc ttcaaggaat gttctttcca gttataagct gttcctcaaa acttagttgt    2460
cgttttttac tgggaggtga tcatggaaga ttaaaatatg cacctcctga agaattttct    2520
cctctcgttg aaagtttgct tcctcaacaa gtgctttcta ttgatccatg ttttttatttt   2580 ggcaacctga ataaatgtgt attggctggt ccttatcctg ttgaagatga ttgtgctttt    2640
gttccagttc cagttgacac atctatggta aatttacccg ttcatgttga tacaatacgc    2700
gatcgtttag ctgaaaacat ccatgaaatg tgggctatga ataaaattga agcaggatgg    2760
atttatggag atgtaagaga tgatataaga agaatacatc catgtcttgt gcaatttgaa    2820
aaactacctc ctgcagaaaa gcgatatgac actcaacttg ctgtacaaac tttaaaaacc    2880
atcattgcac tgggctacca tataacaatg gaaaaaccac catctagaat aaagaacatt    2940
cgtttgccga atgaaccatt tttacaatct aatggttaca agccagctcc tcttgatctc    3000
agtgccataa cactaatacc taaaatggag gaacttgttg accaactcgc tgaaaatact    3060
cacaacttgt gggcaaaaga aagaatccaa caaggctgga cctatggtct aatgaggat    3120 cctgatttgt cccgaagtcc tcacctcgtc ccttacagta aagttgatga tttaattaaa    3180
aaagccaaca gggataccgc aagtgaaact gtcaggactc ttcttgttta tggttataat    3240
ttagaccctc ctacaggtga acaaactgaa gctctcttag cagaagcaag ccgtttgaag    3300
cagatgcagt ttagaaccta tcgggctgaa aagacatatg cagtaaccag tggcaaatgg    3360
tattttgaat ttgaaattct tactgctggg ccaatgagag taggttgggc cattgctgat    3420
tataatccag gttcccagat cggaagtgat gaagcatcct gggcatatga tggttataat    3480
gaggaaaagg tttattctgg ggttgctgaa acgtttggaa gacaatggca agttggagac    3540
gttgtaggag ttttttcttga tctattggat catactatta gtttctctct aaatggtgaa    3600
ctgcttatgg atgcacttgg gggagaaaca tcttttgcag atgttcaggg agaaggatt    3660 gttccagcat ttacacttgg agtaggacaa aaagcaaaat tagtgtttgg gcaagatgtt    3720
aactcactta agttctttac tacctgtggt ttgcaagaag gttatgaacc tttctgtgta    3780
aacatgaaca gggcagttac cttttggtac accaaagatc atcctatatt tgaaaatact    3840
gatgattata ttgatactaa aattgatgca acgcgtattc ctgctggttc tgacacacca    3900
ccatgtctta aaattagtca taatactttt gagacaatgg agaaagccaa ttgggaattt    3960
cttagacttt ctttacctgt tcaatgttta ccatcattca taaatgaaca agaaaaagta    4020
cgtaggtggc aagaaataag gataagacaa cacagacttc ttgtggaagc tgaccaaacc    4080
actcctgctc acattgaaca gattatgaag tctggttttta gtatgagtga tattaagggt    4140
cttcaaagaa gttatacaga agatggaatg gaaggagaag aaggattggc accaagctca    4200
tcaccactta caaggactaa gtcaaaagtg actccagctc gtccacctag gaaaggctcc    4260
ttaccacgaa atggagatgt tattaatatg aacgggacat tagaaccagg tggaggaaaa    4320
atgaaccgtt ctaatagtga gcttgatttc caacgtttca atggtgaaat gcccgatggc    4380
gataacaaga aaaagcgtgg gagatctcca tttaggttct tttcaagaaa aaggggggag    4440
cgtgatacta gtggagaaaa tgcaaaaaat gtacatatgt ctgagcctat gggtaatttc    4500
cttgagcctc caaggactcc aatgcagcaa agaggtggaa gtgctctgcg ttcttctcct    4560
caacctaaag tacaggagtt aactaagcca ccatcccat tagttgaaag aagtggaccc    4620
aaagcaatgt ctgtgcctgt tggaactggc atcgaaacta ttggaaatga aatatttgat    4680
```

```
gtagagtgtt tgaaattgat taatgaatac ttctacggtg tcaggatatt tccaggtcaa    4740
gacccaactc atgtatatgt cggttgggtt acaactcaat tccatctacg tagtaaagac    4800
tttaatcaga atcgagtgct aaagagcact gtagtagtat gtgatgaatt caatcgtgta    4860
atagacagta ttcagcggca gagttgtttt atggtaagag ctgatgaatt atacaatcaa    4920
gtaactcagg atgcctctgg taaaggtgct tcacaaggaa tgtttattgg atgtttcctg    4980
gatactgcta ctggttatgt gacgttcaca tgtgaaggaa aagaaactaa ccacaagtat    5040
aagatggaac ctgatacaaa attatttcca gctatatttg ttgaagctac aagcaaagaa    5100
attctacaaa ttgagcttgg tcgtacatca actacactgc ctttatcagc agctgttctc    5160
caaaattcag aaagacatgt cattcctcag tttccaccaa gacttaaagt tcagtgtcta    5220
aaaccacatc agtgggcacg tgttcctaat atttcattgc atgtccacgc tctgaaatta    5280
tcagatataa gaggttggag tatgctttgt gaagatccag tttcaatgtt agcattacat    5340
atacctgaag aagatagatg tattgatatt ttagaactta ttgaaatgga caaactactt    5400
tcattccatg ctcatacatt gacactttat gcagcactat gttaccaatc caattatcgt    5460
gcaggacatg ttctctgcaa acatgtagac caaaagcaac ttcagtatgc tattaggtct    5520
gaattcatat ctggatcttt acgcttggga ttttatgacc tcttgattgc tttacacatt    5580
gaatcacatg caacaacaat ggaagttttgt aaaaatgaat tcataatacc ccttggtcta    5640
gacttgaaag atttatatga agatccagat atgaagcaca gcttacgatc tttaaaaact    5700
gtctctattt tacctcaaat gagtatgaca gacattacgg aaaatattga aagcatcaat    5760
acattatata gtccttattt tcctcttgat gcagttaagg attatggaat gactgcatta    5820
gaagaggctg taagcatgaa tcaacttcac aatagagacc ctgtaggtgg ttcaaatgaa    5880
aacttgtttc taccccttgtt gaaactggta gatagattat tgcttgttgg gatactacga    5940
gatgaagatg ttacaaagct actaattatg tttgatcctg aaacttggga ttcaaatttt    6000
gaaaaggatg gcaaagatga acatcgtaag ggtttacttc aaatgaaaat ggcagagggg    6060
gcaaaactac agatgtgcta tctcttacag catttatgcg atatacaatt gcggcatcgg    6120
gttgaagcca ttattaattt tagttatgac tatattgctg atcttcagca ggatcagttg    6180
agaagatatg ttgatattaa gcagtctgat cttccatcat cagttgctgc aagaaaaaca    6240
agagagtttc gttgccctcc aagagaacag atgaatgcta tcataaattt taaaaattta    6300
gaagaagatg acaaagaaaa ctgtccatgt ggtgaagaac tgagggagag attaaacaca    6360
tttcatgaag aaactatgag taaagtttca cttgttgctc tccaagagcc acaagaagat    6420
gagaacggtg aaacaccaga aaagccgggt gttttcaaaa aattatacaa ttttattaat    6480
gctgttaaag aattggaaga acctcctaaa atagaagaag aacctgttaa gaaaactcct    6540
gaagaaatat ttagaaaagt attaattagt acaattgtta gatgggctga agaatcccag    6600
attgaaacac caaaattagt cagagaaatg ttcagtctat ggtaaggca gtacgacact    6660 gtaggtgaat taatcagatc tcttggaaac acttatgtga taaatgacaa aacgaaagaa    6720
gatgtagctc agatgtgggt agggttgagc cagatcagag ctctcctacc tgttcaaatg    6780
tctcaagatg aagaaggtct tatgcgaatg aggctatgga aattagttaa caatcacaca    6840 ttcttttcaac atcctgattt gattagagtt cttcgtgttc atgaaaatgt tatggctgtt    6900
atgatcaata ccttgggtag aagatcacaa gcacaatctg atgcttctca agctggtcaa    6960
gaaggtgaac ctgcagctaa ggagaaagat acgtcccatg aaatggtggt agcatgttgt    7020
```

```
cgtttcctgt gttattttg cagaacttca cgtcaaaatc agaaagcaat gtttgaccat    7080
ttaacatttt tattagaaaa cagtaatatt ttactttcaa gaccttcact tagaggaagt    7140
accccctcttg atgttgccta ttcctctctc atggaaaata ccgaactggc attagctctt    7200
agagaacatt atttagagaa gatagctgtt tacttgtctc gctgtggatt acaatctaat    7260
tcagaattgg tagaaaaggg ttaccctgat ttgggttggg atccagttga gggagaaaga    7320
tatttagact tttacgctt ctgtgtttgg gttaacggtg aaagtgttga agaaaatgca    7380
aatctggtta tacggctcct tatacgtcga ccagaatgtt tgggtcctgc acttcgtgga    7440
gaaggtgaag gattactgag agcaattata gatgctaata agatgtctga aagaatttca    7500
gatcgcagaa aaatgatgga ggaacctgaa aattctgccc atcatcagtt tgaacatcca    7560
cttcctgagt ctgatgaaga tgaggactat attgatacag gagcagcaat actggcattc    7620
tattgtactc tggtcgatct tttaggtcgc tgtgctccag atgctagtgt gattgctcag    7680
ggaaagaatg agtctcttag agctagagct attttgagat ctttagtacc tcttgaagat    7740
ttatttggtg tcttgagttt aaagtttaca cttaccaatc cagctattgg agaagaaagg    7800
ccaaaaagtg atataccatc tggtctaata ccatctcata agcaaagtat tgtttattt    7860
ttagagagag tatatggtat tgaacagcaa gatctcttct tcagattact cgaggaagca    7920
tttttacctg atttaagagc agcaactatg ctagatagaa ctgatggttc tgaatcagaa    7980
atggcattag ctatgaatcg ctatattgga aattctattc tcccttttgtt gataaagcat    8040
taccagtttt atagtggtgc agataactat gcaagtcttt tagatgctac acttcataca    8100
gtgtatcgcc tatcaaaaaa tcgaatgcta actaaaggtc agcgagaggc agtatcagat    8160
tttttggttg ctctcacaag tcaattacag ccaagcatgt tactcaaact tcttcgaaag    8220
ttaacagttg atgtatcaaa gctttctgag tataccacag tcgctttaag gttgcttact    8280
ttacactatg agcgttgtgc aaaatattat ggaactactg gaggacaagc tggtggatct    8340
agtgatgaag aaaaaaggct cactatgtta ctcttcagta atattttga ttctttatca    8400
aaaatggatt atgatcctga attatttgga aaagcgcttc cctgcttgag tgctatagga    8460
tgtgcacttc caccgatta ttcactgtcc aagaattatg atgaagaatg gtatagctca    8520
aagggttcag aaccgactga tgggccttat aatccactgc ccatcaatac ttctatggtt    8580
tctctaaata atgatttaaa cacaattgtt caaaaatttt ctgaacatta tcatgatgca    8640
tgggctagtc gaaaaatgga aaatggttgg gtatatggcg aacagtggtc tgacagctct    8700
aaaactcatc ctcgttttaaa accttataca ttgcttaatg attatgaaaa agagagatac    8760
aaagaaccgg ttagagagtc attgaaagct ctgttagcta taggatggaa tgtagagcat    8820
actgaagttg atattccttc taataacaga ggatcatcag tcagaagatc ttctaaagca    8880
aatacatctg atggttcaac accatttaat tatcatccca acccaattga tatgactaat    8940
ttaacattga gtagagaaat gcaaaatatg cagagaggt tagctgaaaa ctcacatgat    9000
atttgggcaa aaagaagaa agaagaactt gtttcatgtg gtggtggtat acacccacag    9060
cttgttccat atgatctttt aacagacaaa gagaagagga aagatagaga aagatctcaa    9120
gaatttttga atatttaca atatcaagga tacaaactcc acaggcctac tcgaggaagt    9180
gctgatgagc aacaggccgc tgcagctgct gccacaggag agtccagatt tgcttacagt    9240
ctactcgaga aacttataca atatactgat aaagcttcta ttaatatgaa actactaaag    9300
ccttctggta cattcagtag acgctccagt ttaaaactt gttcaagaga cataaaattc    9360
ttttccaaag tggtattgct attggttgag aagtatttca gcactcacag aaattacttc    9420
```

```
attgctgttg ccactgcttc taataatgta ggagcagcct ctttaaaaga aaaagaaatg    9480
gttgccagtt tgttctgtaa gctggcaaat ttaattcgaa caaagctggc tgcttttggt    9540
gcagatgttc gaattactgt ccgttgtcta caagtgctag tgaaagctat agatgccaag    9600
tcattggtaa agaattgtcc tgaatttata aggacttcaa tgctgacatt tttcaataat    9660
acagctgatg acttaggcca aactattcag tgtttgcaag agggtcgtta cagtcacctt    9720
agaggcactc atcttaaaac atctacttct ttattttata taaatgatgt tgtactacct    9780
gttctcactt ctatgtttga tcatttggct gtgtgtgatt atggtagcga cttgttactt    9840
gatgaaattc aagtggcctc atatagaatg ttgggtagtt tatataattt aggaattgat    9900
ccaactttaa ctcatgacag aaaatattta aaaacagaaa ttgaaaggca taggcctgcc    9960
attggtgctt gtcttggtgc attttcatca acatttccag tcgcttatct tgaaccccat   10020
ttaaataaac ataatcagtt ttcattagtt aatagaattg ctgaacattc tcttgaagca   10080
caggatattc tagctagaat ggaaaacacc atgcctacat tggatgcgat cctttctgaa   10140
gttgatcagt tcattgaatc cgaaaagagt catacttcag caccacatgt tattgatgtg   10200
attttgcctc tgctttgtgc ttatttgcca agttggtgga gtcaaggtcc tgataatgtc   10260
agtctcacag cagggaatta tgtaacaatg gttactagtg atcatatgaa tcaactccta   10320
aaaaatgtac taaaattaat caaaaataat attggaaatg aaaatgctcc ctggatgacg   10380
agaatagcag cttacaccca gcagatcatc ataaactctt ctgaagaact gttgaaagat   10440
ccattccttc cattaacaca agttgttaag aagaggatag acaatatgtt tcaccgtgaa   10500
gaatctcttc gaggatttct aaaatcttca actgaagata cctctcaagt tgaagcagaa   10560
attcaggagg gctggcatct tattgttaga gatatatatt cttttttatcc actactaatt   10620
aaatatgttg atttacaaag aaatcactgg ttacgtaata atattccgga agctgaatac   10680
ttgtatactc atgttgctga tatatttaat atttggtcta aatcacagta ctttctaaaa   10740
gaagaacaga atttcatatc tgccaacgaa atagacaata tggctctaat tatgcccact   10800
gcaactagga gatctgcagt tgttttggat ggaacagctc ctgctggagg tggaaagaag   10860
aaaaagaagc atcgtgataa gaaaagagat aagaataaag aaatccaagc aagcttaatg   10920
gtagcttgct taaaacgttt attaccagtt ggtcttaacc tattcgctgg aagagaacaa   10980
gagttagttc agcattgtaa agacagatat ttgaagaaaa tgccagaata tgaaatagtg   11040
gattttgcca aaatccaatt aactcttcct gacaagatag atcctggaga tgagatgtct   11100
tggcagcatt atttgtactc aaaactggga aataaaaaag atatcagctc tgaaaaacca   11160
cagcaaatcg atgaggtagt tgataggatt gtggctatgg caaaagttct ttttgggctt   11220
catatgatta tcatccaca actacagagc aagacacaat acagatctgt tgtatccaca   11280
cagagaaagc gtgctgtcat agcttgtttc cggcaactat cactacatgc cttaccaagc   11340
atgcaaataa acctccacct caccaatctg atgaaaag agttctttca gcagcgaaa   11400
aacgggctgc tattgcttgt cttagaactc aacctttgta tacccttcca aggcatcgag   11460
taattaacat atttgctcgc gcttattgtg agctgtggct gcaagaagag aatgttggtc   11520
aagaaatcat gattgaagat cttacacaaa cttttgaaga tgctgaattg aaaaaaagag   11580
attctgaaga agatgaaagc aaacctgatc cacttaccca attagttaca acattttgtc   11640
ggggtgcaat gactgaaagg agtggagctt tgcaagaaga cccactttat atgtcctatg   11700
cagaaattac tgcaaaatca tgtggagaag aagaagaaga aggtggagat gaggaagaag   11760
```

```
gtggagacga agaaggaggg gcatctatcc atgaacaaga aatggaaaaa cagaaactct    11820
tattccatca agctcggcta gccaacagag gtgttgcaga aatggtattg ttacatattt    11880
cagcttgtaa aggtgttccc agtgaaatgg ttatgaaaac tctccagctg gtatttctg     11940
ttttacgtgg tggtaatctt gatattcaaa tgggtatgct aaatcatttg aaagaaaaaa    12000
aggatgttgg attttttact tctatagctg gcttgatgaa ctcctgcagt gtgttggatt    12060
tagatgcatt tgaaagaaac acaaaagctg aaggcttagg agttggttca gaaggtgctg    12120
ctggtgaaaa gaacatgcat gatgctgaat tcacctgtac tcttttcaga tttattcaac    12180
ttacctgtga agggcataac ttagaatggc agaattatct tagaacccaa gctggaaata    12240
caacaacagt taatgttgtt atttgtactg ttgattacct tttgagatta caggaatcaa    12300
ttatggactt ctattggcac tattcgagta aagaattaat tgatcctgct ggaaaagcca    12360
acttttcaa agcaattggt gtggctagtc aagtatttaa tacactctct gaagtaattc     12420
aagggccttg cccacaaaat caacaagctc tggctcattc aagattgtgg gatgctgttg    12480
gaggattttt gtttctttc tctcatatgc aagataagct atcaaaacat tctagtcaag      12540
tagacttact gaaagaactt ttgaatttac agaaagatat gataacaatg atgctatcaa    12600
tgttggaagg taatgttgtg aatggtacta ttggaaaaca gatggtagac acattagttg    12660
aatctgcctc aaatgtggaa ttgatttga agtacttcga catgttttg aaattgaaag       12720
atttgacatc ctctgctagc ttcttggaac ttgatccaaa ccatgaaggc tgggtaacac    12780
ctaaagattt taaagaaaaa atggaacagc agaaaagtta tactccagaa gaaatagact    12840
tcatgttaca gtgctgtgaa accaatcatg acggtaaaat tgactatgtt ggcttcacgg    12900
atagattcca tgagccggcc aaggaaattg gttttaacct agctgttctt ctcacaaatt    12960
tatctgagca tatgccaaat gaaccgagac ttgctcgctt tttagaaaca gctggtagtg    13020
ttcttaacta ctttgaacct ttcctgggac gaattgaaat attaggtagt agtaaacgaa    13080
tcgagcgtgt atatttcgag attaaagaat caaatattga acagtgggaa aaacctcaaa    13140
tcaaggaatc taaacgagca ttttttctatt caattgtcac tgaaggaggt gacaaagaaa   13200
aattggaagc ttttgttaat ttttgtgaag atgccatatt tgagatgaca catgccagtg    13260
ggcttatggc aactgatgat ggtacaggct ctggaggagg aaaacaaaga gcatcctctt    13320
attcttatat ggaagatgaa gatgaagaaa ggaatccaat cagacgtggt tgcaagcaa     13380
ctaaagatgg aatttacttt atgttctcaa tgttatctcc tagcaatatt aaacataaaa    13440
ttattgaaat gcaacaaatg tcaattattg aactaatgat tggttttata aaactatttt    13500
tctacatgtt ttattactca ggatattctg tatcagttgt actgaagtat attggtggta    13560
ttatattttc attgatgagg ggaccacaaa ttgaagagcc agttgtagaa gttaaagagg    13620
aagaaaaatc tggacctctg aggataatgc ctgctttgcc accacctgaa gatagctctc    13680
tgcttccatc tgatgggtca agagacatga aaaaagaaga cagtcagcct ccatcaaaag    13740
tcatagaagg ggctattccc atagaagaag gaggtgagag gagctcagag gaacatgcgg    13800
gagaccatgt aaaaccagaa aatgaagagc aacctccaac accaacactt gctgatatat    13860
tgggtggaga agcagcaaga aaagaagcag cacaaagagc agaagtcgct gctgaacaag    13920
aagcagttat ggctgctttt gaggcagaat ctaaaataga aaaagtttca gagccttctg    13980
ctgtctctca aattgatttt aacaagtata ctcaccgggc tgtcagtttc cttgctcgta    14040
atttctataa tcttaaatat gtagcattgg ttttggcttt ctgcattaac tttatttat     14100
tgttctacaa ggtaacaaca ttgggtgaag atgatgatgc tgctagcgga gaagggagtg    14160
```

```
ttgaacaact aatggaagaa ttaacaggcg aaggtgatga tgtgagtggc ggaggaagta    14220
gtggtggaga aagtggtgaa gaggatccaa ttgaaatggt tcatgtggat gaggatttct    14280
tttatatggc acatgttatg cgattggctg caatcctaca ttctcttgtt tctttagcta    14340
tgttgattgc atattatcat ttgaaggtcc ctctagctat attcaagaga gaaaagaaa     14400 tagctcgtcg acttgagttt gatggtttgt acattgctga gcaaccagaa gatgatgata    14460
ttaaatcaca ttgggataaa ctggttatct gtgcaaaatc atttcctgtt aattactggg    14520
ataaatttgt gaagaaaaag gttcgacaga aatacagtga aacttatgac tttgattcaa    14580
taagtaatct tttgggaatg gaaaaaacat ctttcagtgc ccaagatact gaagaaggat    14640
cgggacttat tcattacatt ttgaactttg actggaggta tcagctttgg aaagcaggag    14700
tcacaatcac agataatgca tttttgtaca gttattata  cttcatcttt tcaatttgg     14760 gaaacttcaa taacttttc  tttgctgccc atttacttga tgttgcagtt ggttttaaaa    14820
cattgaggac tattttgcaa tcagtcacac acaatgaaaa acagcttgta ttgactgtaa    14880
tgctgctaac catcatagta tacatctata ctgtcattgc tttcaacttc ttccgaaaat    14940
tttatgtcca agaagaggat gaggaagtgg ataaaaaatg ccacgatatg ttaacttgtt    15000
ttgtattcca cctttacaaa ggagttagag ctggtggtgg tattggtgat gagattgaac    15060
ctcctgatgg tgatgattat gaagtttaca ggataatgtt tgatattacg ttttctttt     15120 ttgttattgt catcttgcta gccatcattc aaggtttgat cattgatgca tttggtgaat    15180
tgagagatca gttagaaagt gtaaaagaag acatggaatc taactgcttc atttgtggga    15240
taggaaaaga ttattttgat aaagttcccc atggttttga cactcatgtt caacaagaac    15300
ataacttggc taattacatg ttctttctta tgcatctgat taacaagcca gatactgaat    15360
acacaggtca agaaacctat gtctggaaca tgtatcagca acgttgttgg gatttcttcc    15420
cagttggtga ctgttttcgt aaacagtatg aagatgaact gggaggtggt ggtggttaat    15480
tcatttgggt gggtggtggc taaatttata ttattaaaac aaaattaatg ctgggaacta    15540
tcaaacatcc ttcaatttta ttaaaatttc agctaaattc aacaatatat cttatgatat    15600
tgtatttgtc taatgaagga atagaactat cgtgttatga atcagtgaag ttttcacttg    15660
tttagcataa tttatgctaa gtttactatt gcaaatact  ttctttatat ccgaaaatgt    15720
tgtaaaataa atgtaaatgg tgtggcctta aatataatg                           15759
```

<210> SEQ ID NO 19
<211> LENGTH: 15667
<212> TYPE: DNA
<213> ORGANISM: Artificial Sequence
<220> FEATURE:
<223> OTHER INFORMATION: Description of artificial sequence note = synthetic construct

<400> SEQUENCE: 19

```
caacttccta acgacgaggt agttcttgga tatgtaatac gggagagcca tccacttctt      60
tcactggtct gctaagtaga gaggatggcc gacagcgaag gaggatccga gcaggacgat     120
gtttcgttcc tgaggacgga ggatatggtg tgcctatcat gcacagcaac tggagagaga    180
gtttgcttag cagctgaggg cttttggtaac cgtcactgtt ttctagaaaa tattgctgat    240
aagaatatac caccagatct ttcaacatgt gtatttgtta ttgaacaagc tctatcagta    300
agagcacttc aggagttagt tacagcagct ggatctgaag agggaaaggg aactggatct    360
ggtcacagga ctcttctttta tggaaatgct atactactcc ggcaccaaaa cagtgacatg    420
```

```
tatctggctt gtttatctac cagttcatca aatgacaagc tctcatttga tgttggttta    480
caagaacatt cccaagggga agcttgttgg tggaccgtac accctgcttc taaacagaga    540
tcagaaggtg aaaaagtgag agttggtgat gatttaattc ttgtgtctgt agccactgaa    600
agatatttgc atactgctaa agaaaacgat caatctattg taaatgcatc tttccatgta    660
actcattggt ctgttcagcc ttatggaact ggtatcagca aatgaagta tgttggttat     720 gtgttcggag gagatgtgtt aagatttttc catggtgggg atgaatgcct taccattcca    780
tcaacttgga gtgaaacccc tggacaaaat gtggtagttt atgaaggagg gagtgttttg    840
agtcaagctc gttcactttg gagattggaa ctggctagga caaaatggtc tggtggtttc    900
attaattggt atcatccaat gaggatacga catctcacca ctggtagata cttaggagtt    960
aatgaaaata tgaattaca cctcgttgtt agggaggaag ccacaacagc attatctaca   1020
ttcattttaa gacaagaaaa agatgaccaa aaagtagtaa tggaagataa ggatttagaa   1080
gtaataggag ctccaataat aaaatatggt gacagtactg ttttagtcca acattcagaa   1140
agtggtttat ggttaactta taagtcattc gaaactaaga aaaaggtgt gggtaaagta    1200 gaagaaaaac aagctgtact tcatgaggag ggaaaaatgg atgatggatt agactttagt   1260
agaagtcaag aagaagaatc aaggactgct agagtaataa ggaaatgttc gtcacttttc   1320
actcaattta ttaggggtct agaaactctg caaatgaatc gaagacattc tctgttttgc   1380
gctagtgtaa atttaaatga aatggtcatg tgtttagaag atttaattaa ttactttgcc   1440
cagcctgagg aagatatgga acatgaggaa aaacaaaacc ggttaagagc tttgagaaac   1500
agacaagatt tgttccaaga agaaggaatt ttaaatctta tcttagaagc cattgataaa   1560
attaatgtta taacatccca aggtttctta gtcagtttag ctggagatga gtctggacag   1620
agctgggata taatctcagg atatttgtat caactgctag ctgccatcat aaaaggaaat   1680
catactaatt gtgctcagtt tgctaacaca aatagattaa actggttatt tagcagacta   1740
ggttctcaag cttcaagtga gggcacaggt atgttggatg tacttcattg cgtcttaatt   1800
gattctccag aagctttgaa tatgatgaga gatgaacata taaaagtaat catttcactg   1860
ctagaaaaac atgggcgaga tccaagagtt ttagatgtac tttgttcact ttgtgttggt   1920
aatggtgtag cagtccgtag ctcacaaaac aacatctgtg atttccttct gccaggaaaa   1980
aacttgcttc tacaaacgca acttgtggat catgttgcca gtgtcaggcc aaatattttt   2040
gtgggtcgag tcgaaggttc tgctgtttat caaaaatggt attttgaagt gactttagat   2100
catatggagc aaaccaccca tatgacaccg catctaagaa ttggctgggc taacacttct   2160
ggttatgttc cctttcctgg cggtggtgaa aaatgggcg taatggagt tggtgatgat    2220 ctctactctt ttggttttga tggagctgca ttatggacag gtggaagaaa aactgtagtc   2280
cttcctcatg ctatggaacc ttacataaga aagggagatg ttattggttg tgctttcgat   2340
ctgactgttc caattattac atttactttt aatggaacat taatccgagg atcatttagg   2400
gattttaatc ttcaaggaat gttctttcca gttataagct gttcctcaaa acttagttgt   2460
cgttttttac tgggaggtga tcatggaaga ttaaaatatg cacctcctga agaattttct   2520
cctctcgttg aaagtttgct tcctcaacaa gtgcttttcta ttgatccatg tttttatttt   2580
ggcaacctga ataaatgtgt attggctggt cctatcctg ttgaagatga ttgtgctttt    2640
gttccagttc cagttgacac atctatgta aatttacccg ttcatgttga tacaatacgc   2700
gatcgtttag ctgaaaacat ccatgaaatg tgggctatga ataaaattga agcaggatgg   2760
```

-continued

```
atttatggag atgtaagaga tgatataaga agaatacatc catgtcttgt gcaatttgaa    2820
aaactacctc ctgcagaaaa gcgatatgac actcaacttg ctgtacaaac tttaaaaacc    2880
atcattgcac tgggctacca tataacaatg gaaaaaccac catctagaat aaagaacatt    2940
cgtttgccga atgaaccatt tttacaatct aatggttaca agccagctcc tcttgatctc    3000
agtgccataa cactaatacc taaaatggag gaacttgttg accaactcgc tgaaaatact    3060
cacaacttgt gggcaaaaga aagaatccaa caaggctgga cctatggtct taatgaggat    3120
cctgatttgt cccgaagtcc tcacctcgtc ccttacagta aagttgatga tttaattaaa    3180
aaagccaaca gggataccgc aagtgaaact gtcaggactc ttcttgttta tggttataat    3240
ttagaccctc ctacaggtga acaaactgaa gctctcttag cagaagcaag ccgtttgaag    3300
cagatgcagt ttagaaccta tcgggctgaa aagacatatg cagtaaccag tgcaaatgg     3360
tattttgaat ttgaaattct tactgctggg ccaatgagag taggttgggc cattgctgat    3420
tataatccag gttcccagat cggaagtgat gaagcatcct gggcatatga tggttataat    3480
gaggaaaagg tttattctgg ggttgctgaa acgtttggaa gacaatggca agttggagac    3540
gttgtaggag tttttcttga tctattggat catactatta gtttctctct aaatggtgaa    3600
ctgcttatga atgcacttgg gggagaaaca tcttttgcag atgttcaggg agaaggatt    3660
gttccagcat ttacacttgg agtaggacaa aaagcaaaat tagtgtttgg gcaagatgtt    3720
aactcactta agttctttac tacctgtggt ttgcaagaag gttatgaacc tttctgtgta    3780
aacatgaaca gggcagttac cttttggtac accaaagatc atcctatatt tgaaaatact    3840
gatgattata ttgatactaa aattgatgca acgcgtattc ctgctggttc tgacacacca    3900
ccatgtctta aaattagtca taatactttt gagacaatgg agaaagccaa ttgggaattt    3960
cttagacttt ctttacctgt tcaatgttta ccatcattca taaatgaaca agaaaaagta    4020
cgtaggtggc aagaaataag gataagacaa cacagacttc ttgtggaagc tgaccaaacc    4080
actcctgctc acattgaaca gattatgaag tctggtttta gtatgagtga tattaagggt    4140
cttcaaagaa gttatacaga agatggaatg gaaggagaag aaggattggc accaagctca    4200
tcaccactta caaggactaa gtcaaaagtg actccagctc gtccacctag gaaaggctcc    4260
ttaccacgaa atggagatgt tattaatatg aacgggacat tagaaccagg tggaggaaaa    4320
atgaaccgtt ctaatagtga gcttgatttc caacgtttca atggtgaaat gcccgatggc    4380
gataacaaga aaaagcgtgg gagatctcca tttaggttct tttcaagaaa aaggggggag    4440
cgtgatacta gtggagaaaa tgcaaaaaat gtacatatgt ctgagcctat gggtaatttc    4500
cttgagcctc caaggactcc aatgcagcaa agaggtggaa gtgctctgcg ttcttctcct    4560
caacctaaag tacaggagtt aactaagcca ccatcccccat tagttgaaag aagtggaccc    4620
aaagcaatgt ctgtgcctgt tggaactggc atcgaaacta ttggaaatga aatatttgat    4680
gtagagtgtt tgaaattgat taatgaatac ttctacggtg tcaggatatt tccaggtcaa    4740
gacccaactc atgtatatgt cggttgggtt acaactcaat tccatctacg tagtaaagac    4800
tttaatcaga atcgagtgct aaagagcact gtagtagtat gtgatgaatt caatcgtgta    4860
atagacagta ttcagcggca gagttgtttt atggtaagag ctgatgaatt atacaatcaa    4920
gtaactcagg atgcctctgg taaaggtgct tcacaaggaa tgtttattgg atgtttcctg    4980
gatactgcta ctggttatgt gacgttcaca tgtgaaggaa aagaaactaa ccacaagtat    5040
aagatggaac ctgatacaaa attatttcca gctatatttg ttgaagctac aagcaaagaa    5100
attctacaaa ttgagcttgg tcgtacatca actacactgc ctttatcagc agctgttctc    5160
```

```
caaaattcag aaagacatgt cattcctcag tttccaccaa gacttaaagt tcagtgtcta    5220
aaaccacatc agtgggcacg tgttcctaat atttcattgc atgtccacgc tctgaaatta    5280
tcagatataa gaggttggag tatgctttgt gaagatccag tttcaatgtt agcattacat    5340 ataccctgaag aagatagatg tattgatatt ttagaactta ttgaaatgga caaactactt    5400
tcattccatg ctcatacatt gacactttat gcagcactat gttaccaatc caattatcgt    5460
gcaggacatg ttctctgcaa acatgtagac caaaagcaac ttcagtatgc tattaggtct    5520
gaattcatat ctggatcttt acgcttggga ttttatgacc tcttgattgc tttacacatt    5580
gaatcacatg caacaacaat ggaagtttgt aaaaatgaat tcataatacc ccttggtcta    5640
gacttgaaag atttatatga agatccagat atgaagcaca gcttacgatc tttaaaaact    5700 gtctctatttt tacctcaaat gagtatgaca gacattacgg aaaatattga aagcatcaat    5760
acattatata gtccttatttt tcctcttgat gcagttaagg attatggaat gactgcatta    5820
gaagaggctg taagcatgaa tcaacttcac aatagagacc ctgtaggtgg ttcaaatgaa    5880
aacttgtttc taccccttgtt gaaactggta gatagattat tgcttgttgg gatactacga    5940
gatgaagatg ttacaaagct actaattatg tttgatcctg aaacttggga ttcaaatttt    6000
gaaaaggatg gcaaagatga acatcgtaag ggtttacttc aaatgaaaat ggcagagggg    6060
gcaaaactac agatgtgcta tctcttacag catttttatgcg atatacaatt gcggcatcgg    6120
gttgaagcca ttattaattt tagttatgac tatattgctg atcttcagca ggatcagttg    6180
agaagatatg ttgatattaa gcagtctgat cttccatcat cagttgctgc aagaaaaaca    6240
agagagtttc gttgccctcc aagagaacag atgaatgcta tcataaatttt taaaaattta    6300 gaagaagatg acaaagaaaa ctgtccatgt ggtgaagaac tgagggagag attaaacaca    6360
tttcatgaag aaactatgag taaagtttca cttgttgctc tccaagagcc acaagaagat    6420
gagaacggtg aaacaccaga aaagccgggt gttttcaaaa aattatacaa tttttattaat    6480 gctgttaaag aattggaaga acctcctaaa atagaagaag aacctgttaa gaaaactcct    6540
gaagaaatat ttagaaaagt attaattagt acaattgtta gatgggctga agaatcccag    6600
attgaaacac caaaattagt cagagaaatg ttcagtctat tggtaaggca gtacgacact    6660
gtaggtgaat taatcagatc tcttggaaac acttatgtga taaatgacaa aacgaaagaa    6720
gatgtagctc agatgtgggt aggggttgagc cagatcagag ctctcctacc tgttcaaatg    6780
tctcaagatg aagaaggtct tatgcgaatg aggctatgga aattagttaa caatcacaca    6840
ttctttcaac atcctgattt gattagagtt cttcgtgttc atgaaaatgt tatggctgtt    6900
atgatcaata ccttgggtag aagatcacaa gcacaatctg atgcttctca agctggtcaa    6960
gaaggtgaac ctgcagctaa ggagaaagat acgtcccatg aaatggtggt agcatgttgt    7020
cgtttcctgt gttattttg cagaacttca cgtcaaaatc agaaagcaat gtttgaccat    7080
ttaacatttt tattagaaaa cagtaatatt ttactttcaa gaccttcact tagaggaagt    7140
acccctcttg atgttgccta ttcctctctc atggaaaata ccgaactggc attagctctt    7200
agaacacatt atttagagaa gatagctgtt tacttgtctc gctgtggatt acaatctaat    7260
tcagaattgg tagaaaaggg ttaccctgat ttgggttggg atccagttga gggagaaaga    7320
tatttagact ttttacgctt ctgtgttttgg gttaacggtg aaagtgttga agaaaatgca    7380
aatctggtta tacggctcct tatacgtcga ccagaatgtt tgggtcctgc acttcgtgga    7440
gaaggtgaag gattactgag agcaattata gatgctaata agatgtctga aagaatttca    7500
```

```
gatcgcagaa aaatgatgga ggaacctgaa aattctgccc atcatcagtt tgaacatcca    7560
cttcctgagt ctgatgaaga tgaggactat attgatacag gagcagcaat actggcattc    7620
tattgtactc tggtcgatct tttaggtcgc tgtgctccag atgctagtgt gattgctcag    7680
ggaaagaatg agtctcttag agctagagct attttgagat ctttagtacc tcttgaagat    7740
ttatttggtg tcttgagttt aaagtttaca cttaccaatc cagctattgg agaagaaagg    7800
ccaaaaagtg atataccatc tggtctaata ccatctcata agcaaagtat tgttttattt    7860
ttagagagag tatatggtat tgaacagcaa gatctcttct tcagattact cgaggaagca    7920 ttttttacctg atttaagagc agcaactatg ctagatagaa ctgatggttc tgaatcagaa    7980
atggcattag ctatgaatcg ctatattgga aattctattc tcccttttgtt gataaagcat    8040 taccagtttt atagtggtgc agataactat gcaagtcttt tagatgctac acttcataca    8100
gtgtatcgcc tatcaaaaaa tcgaatgcta actaaaggtc agcgagaggc agtatcagat    8160
tttttggttg ctctcacaag tcaattacag ccaagcatgt tactcaaact tcttcgaaag    8220
ttaaccgttg atgtatcaaa gctttctgag tataccacag ttgctttaag gttgcttact    8280
ttacactatg agcgttgtgc aaaatattat ggaactactg gtggacaagc tggtggatct    8340
agtgatgaag aaaaaaggct cactatgtta ctcttcagta atattttttga ttctttatca    8400 aaaatggatt atgatcctga attatttgga aaagcgcttc cctgcttgag tgctatagga    8460
tgtgcacttc cacccgatta ttcactgtcc aagaattatg atgaagaatg gtatagttca    8520
aagggttcag aaccgactga tgggccttat aatccactgc ccatcaatac ttctatggtt    8580
tctctaaata tgattttaaa cacaattgtt caaaaatttt ctgaacatta tcatgatgca    8640
tgggctagtc gaaaaatgga aaatggttgg gtatatggtg agcagtggtc tgacagctct    8700
aaaactcatc ctcgttttaaa accttataca ttgcttaatg attatgaaaa agagagatac    8760
aaagaaccgg ttagagagtc attgaaagct ctgttagcta taggatggaa tgtagagcat    8820
actgaagttg atattccttc taataacaga ggatcatcag tcagaagatc ttctaaagca    8880
aatacatctg atggttcaac accatttaat tatcatccca acccaattga tatgactaat    8940
ttaacattga gtagagaaat gcaaaatatg gcagagaggt tagctgaaaa ctcacatgat    9000
atttgggcaa aaagaagaa agaagaactt gtttcatgtg gtggtggtat acacccacag    9060
cttgttccat atgatctttt aacagacaaa gagaagagga agatagaga aagatctcaa    9120 gaatttttga aatatttaca atatcaagga tacaaactcc acaggcctac tcgaggaagt    9180
gctgatgagc aacaggccgc tgcagctgct gccacaggag agtccagatt tgcttacagt    9240
ctactcgaga aacttataca atatactgat aaagcttcta ttaatatgaa actactaaag    9300
ccttctggta cattcagtag acgctccagt tttaaaactt gttcaagaga cataaaattc    9360
ttttccaaag tggtattgct attggttgag aagtatttca gcactcacag aaattacttc    9420
attgctgttg ccactgcttc taataatgta ggagcagcct cttttaaaga aaagaaatg    9480 gttgccagtt tgttctgtaa gctggcaaat ttaattcgaa caaagctggc tgcttttggt    9540
gcagatgttc gaattactgt ccgttgtcta caagtgctag tgaaagctat agatgccaag    9600
tcattggtaa agaattgtcc tgaatttata aggacttcaa tgctgacatt tttcaataat    9660
acagctgatg acttaggcca aactattcag tgtttgcaag agggtcgtta cagtcacctt    9720
agaggcactc atcttaaaac atctacttct ttattttata taaatgatgt tgtactacct    9780
gttctcactt ctatgtttga tcatttggct gtgtgtgatt atggtagcga cttgttactt    9840
gatgaaattc aagtggcctc atatagaatg ttgggtagtt tatataattt aggaattgat    9900
```

```
ccaactttaa ctcatgacag aaatatttta aaaacagaaa ttgaaaggca taggcctgcc    9960
attggtgctt gtcttggtgc attttcatca acatttccag tcgcttatct tgaaccccat   10020
ttaaataaac ataatcagtt ttcattagtt aatagaattg ctgaacattc tcttgaagca   10080
caggatattc tagctagaat ggaaaacacc atgcctacat tggatgcgat cctttctgaa   10140
gttgatcagt tcattgaatc cgaaaagagt catacttcag caccacatgt tattgatgtg   10200
attttgcctc tgctttgtgc ttatttgcca agttggtgga gtcaaggtcc tgataatgtc   10260
agtctcacag cagggaatta tgtaacaatg gttactagtg atcatatgaa tcaactccta   10320
aaaaatgtac taaaattaat caaaaataat attggaaatg aaaatgctcc ctggatgacg   10380
agaatagcag cttacaccca gcagatcatc ataaactctt ctgaagaact gttgaaagat   10440
ccattccttc cattaacaca agttgttaag aagaggatag acaatatgtt tcaccgtgaa   10500
gaatctcttc gaggatttct aaaatcttca actgaagata cctctcaagt tgaagcagaa   10560
attcaggagg gctggcatct tattgttaga gatatatatt cttttatcc actactaatt   10620 aaatatgttg atttacaaag aaatcactgg ttacgtaata atattccgga agctgaatac   10680
ttgtatactc atgttgctga tatatttaat atttggtcta aatcacagta ctttctaaaa   10740
gaagaacaga atttcatatc tgccaacgaa atagacaata tggctctaat tatgcccact   10800
gcaactagga gatctgcagt tgttttggat ggaacagctc ctgctggagg tgaaagaag   10860 aaaagaagc atcgtgataa gaaaagagat aagaataaag aaatccaagc aagcttaatg   10920
gtagcttgct taaacgtttt attaccagtt ggtcttaacc tattcgctgg aagagaacaa   10980
gagttagttc agcattgtaa agacagatat ttgaagaaaa tgccagaata tgaaatagtg   11040
gattttgcca aaatccaatt aactcttcct gacaagatag atcctggaga tgagatgtct   11100
tggcagcatt atttgtactc aaaactggga aataaaaaag atatcagctc tgaaaaacca   11160
cagcaaatcg atgaggtagt tgataggatt gtggctatgg caaaagttct ttttgggctt   11220
catatgattg atcatccaca actacagagc aagacacaat acagatctgt tgtatccaca   11280
cagagaaagc gtgctgtcat agcttgtttc cggcaactat cactacatgc cttaccaagg   11340
catcgagtaa ttaacatatt tgctcgcgct tattgtgagc tgtggctgca agaagagaat   11400
gttggtcaag aaatcatgat tgaagatctt acacaaactt ttgaagatgc tgaattgaaa   11460 aaagagatt ctgaagaaga tgaaagcaaa cctgatccac ttacccaatt agttacaaca   11520
ttttgtcggg gtgcaatgac tgaaaggagt ggagctttgc aagaagaccc actttatatg   11580
tcctatgcag aaaattactgc aaaatcatgt ggagaagaag aagaagaagg tggagatgag   11640
gaagaaggtg gagacgaaga aggaggggca tctatccata agacaatggc aaaattagtg   11700
gaacaagaaa tggaaaaaca gaaactctta ttccatcaag ctcggctagc caacagaggt   11760
gttgcagaaa tggtattgtt acatatttca gcttgtaaag gtgttcccag tgaaatggtt   11820
atgaaaactc tccagctggg tatttctgtt ttacgtggtg gtaatcttga tattcaaatg   11880
ggtatgctaa atcatttgaa agaaaaaaag gatgttggat tttttacttc tatagctggc   11940
ttgatgaact cctgcagtgt gttggattta atgcatttg aaagaaacac aaaagctgaa   12000
ggcttaggag ttggttcaga aggtgctgct ggtgaaaaga acatgcatga tgctgaattc   12060
acctgtactc ttttcagatt tattcaactt acctgtgaag gcataacttt agaatggcag   12120
aattatctta gaacccaagc tggaaatacac acaacagtta atgttgttat ttgtactgtt   12180
gattaccttt tgagattaca ggaatcaatt atggacttct attggcacta ttcgagtaaa   12240
```

```
gaattaattg atcctgctgg aaaagccaac ttttcaaag caattggtgt ggctagtcaa    12300
gtatttaata cactctctga agtaattcaa gggccttgcc cacaaaatca acaagctctg    12360
gctcattcaa gattgtggga tgctgttgga ggattttgt ttcttttctc tcatatgcaa    12420
gataagctat caaaacattc tagtcaagta gacttactga agaacttt gaatttacag    12480 aaagatatga taacaatgat gctatcaatg ttggaaggta atgttgtgaa tggtactatt    12540
ggaaaacaga tggtagacac attagttgaa tctgcctcaa atgtggaatt gattttgaag    12600
tacttcgaca tgtttttgaa attgaaagat ttgacatcct ctgctagctt cttggaactt    12660
gatccaaacc atgaaggctg gtaacaccct aaagatttta agaaaaaat ggaacagcag    12720 aaaagttata ctccagaaga aatagacttc atgttacagt gctgtgaaac caatcatgac    12780
ggtaaaattg actatgttgg cttcacggat agattccatg agccggccaa ggaaattggt    12840
tttaacctag ctgttcttct cacaaattta tctgagcata tgccaaatga accgagactt    12900
gctcgctttt tagaaacagc tggtagtgtt cttaactact ttgaaccttt cctgggacga    12960
attgaaatat taggtagtag taaacgaatc gagcgtgtat atttcgagat taagaatca    13020 aatattgaac agtgggaaaa acctcaaatc aaggaatcta acgagcatt tttctattca    13080 attgtcactg aaggaggtga caaagaaaaa ttggaagctt tgttaatttt ttgtgaagat    13140
gccatatttg agatgacaca tgccagtggg cttatggcaa ctgatgatgg tacaggctct    13200
ggaggaggaa acaaagagc atcctcttat tcttatatgg aagatgaaga tgaagaaagg    13260
aatccaatca gacgtggttg gcaagcaact aaagatggaa tttactttat gttctcaatg    13320
ttatctccta gcaatattaa acataaaatt attgaaatgc aacaaatgtc aattattgaa    13380
ctaatgattg gttttataaa actatttttc tacatgtttt attactcagg atattctgta    13440
tcagttgtac tgaagtatat tggtggtatt atattttcat tgatgagggg accacaaatt    13500
gaagagccag ttgtagaagt taaagaggaa gaaaaatctg gacctctgag gataatgcct    13560
gctttgccac cacctgaaga tagctctctg cttccatctg atgggtcaag agacatgaaa    13620
aaagaagaca gtcagcctcc atcaaaagtc atagaagggg ctattcccat agaagaagga    13680
ggtgagagga gctcagagga acatgcggga gaccatgtaa aaccagaaaa tgaagagcaa    13740
cctccaacac caacacttgc tgatatattg ggtggagaag cagcaagaaa agaagcagca    13800
caaagagcag aagtcgctgc tgaacaagaa gcagttatgg ctgcttttga ggcagaatct    13860
aaaatagaaa agtttcaga gccttctgct gtctctcaaa ttgattttaa caagtatact    13920
caccgggctg tcagtttcct tgctcgtaat ttctataatc ttaaatatgt agcattggtt    13980
ttggctttct gcattaactt tattttattg ttctacaagg taacaacatt gggtgaagat    14040
gatgatgctg ctagcggaga agggagtgtt gaacaactaa tggaagaatt aacaggcgaa    14100
ggtgatgatg tgagtggcgg aggaagtagt ggtggagaaa gtggtgaaga ggatccaatt    14160
gaaatggttc atgtgatga ggatttcttt tatatggcac atgttatgcg attggctgca    14220
atcctacatt ctcttgttc tttagctatg ttgattgcat attatcattt gaaggtccct    14280
ctagctatat tcaagagaga aaaagaaata gctcgtcgac ttgagtttga tggtttgtac    14340
attgctgagc aaccgaaga tgatgatatt aaatcacatt gggataaaact ggttatctgt    14400 gcaaaatcat ttcctgttaa ttactgggat aaatttgtga agaaaaggt tcgacagaaa    14460 tacagtgaaa cttatgactt tgattcaata agtaatcttt tgggaatgga aaaacatct    14520 ttcagtgccc aagatactga agaaggatcg ggacttattc attacatttt gaactttgac    14580
tggaggtatc agctttggaa agcaggagtc acaatcacag ataatgcatt tttgtacagt    14640
```

```
ttattatact tcatcttttc aattttggga aacttcaata acttttttctt tgctgcccat    14700 ttacttgatg ttgcagttgg ttttaaaaca ttgaggacta ttttgcaatc agtcacacac    14760
aatggaaaac agcttgtatt gactgtaatg ctgctaacca tcatagtata catctatact    14820
gtcattgctt tcaacttctt ccgaaaattt tatgtccaag aagaggatga ggaagtggat    14880
aaaaaatgcc acgatatgtt aacttgtttt gtattccacc tttacaaagg agttagagct    14940
ggtggtggta ttggtgatga gattgaacct cctgatggtg atgattatga agtttacagg    15000
ataatgtttg atattacgtt tttctttttt gttattgtca tcttgctagc catcattcaa    15060
ggtttgatca ttgatgcatt tggtgaattg agagatcagt tagaaagtgt aaaagaagac    15120
atggaatcta actgcttcat ttgtgggata ggaaaagatt attttgataa agttccccat    15180
ggttttgaca ctcatgttca acaagaacat aacttggcta attacatgtt ctttcttatg    15240
catctgatta acaagccaga tactgaatac acaggtcaag aaacctatgt ctggaacatg    15300
tatcagcaac gttgttggga tttcttccca gttggtgact gttttcgtaa acagtatgaa    15360
gatgaactgg gaggtggtgg tggttaattc atttgggtgg gtggtggcta aatttatatt    15420
attaaaacaa aattaatgct gggaactatc aaacatcctt caattttatt aaaatttcag    15480
ctaaattcaa caatatatct tatgatattg tatttgtcta atgaaggaat agaactatcg    15540
tgttatgaat cagtgaagtt ttcacttgtt tagcataatt tatgctaagt ttactattgc    15600
aaaatacttt ctttatatcc gaaaatgttg taaaataaat gtaaatggtg tggccttaaa    15660
tataatg                                                              15667
```

<210> SEQ ID NO 20
<211> LENGTH: 1486
<212> TYPE: DNA
<213> ORGANISM: Artificial Sequence
<220> FEATURE:
<223> OTHER INFORMATION: Description of artificial sequence note = synthetic construct

<400> SEQUENCE: 20

```
cagtgatcta cttctgggtc aactatgtt ttgtttatgg ttttcattaa atttacgaga      60
cattaaaaac taagaatatt gattgcttat gaagttatca atgataacta atattgttat    120
ttcgatgctg ttatgttgga tacattgttg gtgactggca ttagcttatg cgtgaaacct    180
tcttcgtaaa tattcaaatt tagaatcaaa tattattgat actatttctt tttcatactt    240
tacattaata ttcttcaaaa ttaaaaatgc caggagtaga gcatgttact aacaaagtcg    300
ttgttcatcc tttagttcta ttaagtgttg ttgatcattt caatagaatg ggtaaaattg    360
ggaatcagaa gagagtagtt ggcgtattat taggatgctg gaaggcaaaa ggtgttttag    420
acgtatctaa tagttttgca gtgccatttg atgaagatga taaagacaaa tcagtttggt    480
ttttagacca tgattattta gaaaatatgt atggcatgtt taagaaagtt aatgcaagag    540
aaaaagttgt tggctggtat catacaggcc caaagttaca tcaaaatgat gttgcaatta    600
atgaacttat acgccgttac tgccctaact cagttcttgt tattatcgat gcaaaaccaa    660
aggatcttgg tttacctaca gaagcatata gagcagttga agaagtacat gatgatggtt    720
ctcctacgac aaaaacattt gagcatgttc ccagtgaaat aggggctgaa gaagcagagg    780
aagtgggtgt tgaacatctg ctgagagata taaaagatac aactgtcggc tcactttcgc    840
aaagggttac taatcaattt cttggtctca aaggccttaa tcaacaaatt caagacatca    900
gggattacct tatgcaggtt gttgaaggaa aattgcccat caaccatcaa ataatatatc    960
```

```
agcttcaaga catatttaat ctccttcctg acatgaacca tgggaacttt gttgattcat    1020
tatacataaa aacaaatgat cagatgcttg tcgtttatct cgctgccctc gttagagcta    1080
ttgttgcctt gcataatctg atcaataata aactcagtaa tcgtgatgcc gaaaaaaaag    1140
aaagcaccaa aaaagaagaa aaacctaaag aagaagaaag tgtaaaaaaa gaattgaagg    1200
ctaagtaaat gatgccagtt cattctcagg attgaacaga tgttatttat tgtaagattt    1260
aattataatc ttttatacat atgtgtacat taatagtata tacatcgttt tcaacaaatc    1320
agatttataa tttgtaaaaa aaaagaaaa gggaacaaaa tgatatttaa atatttaact    1380
atttatacat ttttttgtg agtacaatta aaccatttag ttgaacttgt gaactacaaa    1440
aattaatttg taataaaacc agtctaattt cttaatttta aaaaaa                   1486

<210> SEQ ID NO 21
<211> LENGTH: 362
<212> TYPE: DNA
<213> ORGANISM: Artificial Sequence
<220> FEATURE:
<223> OTHER INFORMATION: Description of artificial sequence note =
      synthetic construct

<400> SEQUENCE: 21
gatgttggct tctttataca atggaaacgt tcatatttgg aatcatgaga cccagcagct      60
agtaaagtct tttgaagtat gcgaccaacc agttcgtgct gcagtatttg ttcctcgcaa     120
gaactggatt gtaacagggt cagatgatat gcagatcaga gttttttaatt acaatactct    180 tgaaagagta aatgcatttg aagctcattc agactatgtc agatgtatag cagttcaccc     240
agcccatcct tatattctga catcatcaga tgatatgtta atcaaattgt ggaattggtc     300
taaggcttgg gtctgccaac aaatatttga aggacatacc cattatgtaa tgcaagttgt     360
ta                                                                   362

<210> SEQ ID NO 22
<211> LENGTH: 369
<212> TYPE: DNA
<213> ORGANISM: Artificial Sequence
<220> FEATURE:
<223> OTHER INFORMATION: Description of artificial sequence note =
      synthetic construct

<400> SEQUENCE: 22
aacgtcttgc tttagctcca aaagaaatgg gaccatgtga aatatatcct caaagtattt      60
cacataatcc aaatggaaga tttgtcgttg tttgtggaga tggtgaatac ataatttata    120
ctgctatggc tttaagaaac aaaagttttg gatcagccca agaatttgta tgggcacaag    180
atagttctga ctatgctata agagaaggaa catctactgt aaaactattt agacagttca    240
aggagcgcaa gacacttaag ccagagtttg gtgctgaagg tatatttggt ggacaattgc    300
ttggtgtcag atcagtctca ggattatgtt tatatgattg ggaaactctg gaattaatca    360
gaagaatag                                                            369

<210> SEQ ID NO 23
<211> LENGTH: 374
<212> TYPE: DNA
<213> ORGANISM: Artificial Sequence
<220> FEATURE:
<223> OTHER INFORMATION: Description of artificial sequence note =
      synthetic construct

<400> SEQUENCE: 23
```

```
tgaattagca acgagacaag ccaggcttga tgttgcgcaa gcagctcttc acagagccca    60
acattatggt ggacttctgc ttctctccac atcagcagga aatcgggaaa tgatggaaaa   120
acaggaaaga gttcaggaga aaatggaaaa aataatgtta gcttccttgc atatttcctg   180
cttggagacc ttgccaaatg tcttcaaatt cttattgaca ctgatcgcat tccagaagct   240
gccttttttg ccaggacata tttgccgagt gaggttcctc gagttgttgg gttatggcga   300
ggtttagcaa aggcaggaca gagccttgca gatccttcgc agtatctaat ctcttttccag  360 gttatgcaga tgct                                                    374
```

<210> SEQ ID NO 24
<211> LENGTH: 355
<212> TYPE: DNA
<213> ORGANISM: Artificial Sequence
<220> FEATURE:
<223> OTHER INFORMATION: Description of artificial sequence note =
      synthetic construct

<400> SEQUENCE: 24

```
gatggctgtg gtggaacaac cttgttatac tctgatcaat tttccatctg atttagagcc    60
tcctaatgaa atgcagctaa aatctgattt agaaaatgga gacactaaag cgaaaattga   120
agctttgaaa atatattc atttaattgc aaatggagag cgtctacctg gtttacttat    180
gcatatcata cgttttgttt tgccatcaca agaccatacc ataaaaaaat tactgcttat   240
attttgggaa atcgttccta aaactactcc agatggcaaa cttctccagg aaatgatttt   300
ggtttgtgat gcctatcgga aggacttaca acatcctaat gaatttgtca gggga        355
```

<210> SEQ ID NO 25
<211> LENGTH: 382
<212> TYPE: DNA
<213> ORGANISM: Artificial Sequence
<220> FEATURE:
<223> OTHER INFORMATION: Description of artificial sequence note =
      synthetic construct

<400> SEQUENCE: 25

```
gtgataataa tgttaaatta attgtattag atcgtcttat atctttaaaa gaaattccta    60
ctcatgaacg ggttcttcaa gatttagtta tggatatatt acgtgtgcta gccagtcctg   120
acatggaagt aaagaaaaaa gccttaagcc tagcactgga tctcactact tcacggtgtg   180
ttgaagaaat ggttttaatg ttaaaaaaag aagttgctaa gacacataac ttgacagaac   240
atgaagatgc tggaaaatat cgtcaacttc ttgttagaac tcttcattcc tgttgcatga   300
agtttccaga tgttgctgct tcagttatac cagtattaat ggaatttctc tcagatacaa   360
gtgaactagc ttcgtatgat gt                                            382
```

<210> SEQ ID NO 26
<211> LENGTH: 376
<212> TYPE: DNA
<213> ORGANISM: Artificial Sequence
<220> FEATURE:
<223> OTHER INFORMATION: Description of artificial sequence note =
      synthetic construct

<400> SEQUENCE: 26

```
tcaacactga ttgtcgcaat gctcttgcta atatgttagt tgctcaacag aatgaggagt    60
actcacttat taaggccaaa gaaaaatccg tccataccat ccaagttgat gatcctgtat   120 cattttaca attatcaacg atacgatcat ctgatttgg ttcagaaaat gttttgagc      180
```

| | |
|---|---|
| ttagtttaaa tcaagctgtc gggggccaa atacagctac aaacacagct gaacttccat | 240 |
| tttcagccag taaattgaat aaagtaactc agctgacagg gttttcagat ccagtttatg | 300 |
| cagaagcata tgttcatgtc aaccagtatg acattgtact tgatgttttg atcgttaatc | 360 |
| aaacaggtga tacact | 376 |

<210> SEQ ID NO 27
<211> LENGTH: 340
<212> TYPE: DNA
<213> ORGANISM: Artificial Sequence
<220> FEATURE:
<223> OTHER INFORMATION: Description of artificial sequence note =
      synthetic construct

<400> SEQUENCE: 27

| | |
|---|---|
| attcgaattg catgtaaatt attggaagaa gaaagctctg gagaatatgc agactctcca | 60 |
| ctttttgatt ttattgaagc atgtttacgc cacaaaagtg aaacagttgt ttatgaagca | 120 |
| gctgctgctc ttgtaaactt acgccacact actaccagac aaatcacgcc tgcagtaagt | 180 |
| gttcttcaat tattttgttc ttctccaaaa ccagcgcttc gttttgctgc tgtgagaact | 240 |
| cttaataagg tagcaatgac acatcccact gctgtaacgt catgcaatat tgacttagag | 300 |
| aaccttataa cggattcaaa tcggtccata gctaccttgg | 340 |

<210> SEQ ID NO 28
<211> LENGTH: 383
<212> TYPE: DNA
<213> ORGANISM: Artificial Sequence
<220> FEATURE:
<223> OTHER INFORMATION: Description of artificial sequence note =
      synthetic construct

<400> SEQUENCE: 28

| | |
|---|---|
| gttccgatcc tatcagtctt acggaatctg agacagaata tcaagttaga gtcacgaagc | 60 |
| atgttttcaa aaatcatatt gttcttcagt ttgactgtac aaataccatg agtgaccagc | 120 |
| tactggagaa agttcgagtg cagttagaag tgagcgaagg ttaccagatc gtagctgagg | 180 |
| tccccctgcca aagattagcc tgttcggaaa catcacctac ttatattgcc ctgcaatttc | 240 |
| cagatgcccc taatcttact gtcacaaaact tgctgctac tctgaggttt gttgtaaagg | 300 |
| attgcgaccc aatgaccggt atccctaact cagatgatgg ttatgaagaa gattatatgc | 360 |
| ttgaagatgt cgaagtgatg ctt | 383 |

<210> SEQ ID NO 29
<211> LENGTH: 388
<212> TYPE: DNA
<213> ORGANISM: Artificial Sequence
<220> FEATURE:
<223> OTHER INFORMATION: Description of artificial sequence note =
      synthetic construct

<400> SEQUENCE: 29

| | |
|---|---|
| gacttacgaa gagcaacttc ggtgctgcat gggaggaagg cgaatcgtat agtgagctag | 60 |
| aggacactta taacttgtca ggaataaaca gcctcgaaga ggcagtgagg agtgttgtca | 120 |
| gtttcatggg gatgcagcct gctgacagga gcgacagggt acagcctgat aaatcttcac | 180 |
| acactgtcta cctcggaggc atgttccgtg gtggagttga agtgttagct agagctaaac | 240 |
| tggccatggg taattcccca ggcgttgcca tgcaacttac agtccgctct ccaaatccag | 300 |
| atatttgtga actgattatt tctgtagtcg ggtaaaaaaa atatataaat atatttgaga | 360 | agtacacagt ttcctctcag atgttgta                                388

<210> SEQ ID NO 30
<211> LENGTH: 412
<212> TYPE: DNA
<213> ORGANISM: Artificial Sequence
<220> FEATURE:
<223> OTHER INFORMATION: Description of artificial sequence note =
      synthetic construct

<400> SEQUENCE: 30
acttgtggat catgttgcca gtgtcaggcc aaatatttt gtgggtcgag tcgaaggttc      60
tgctgtttat caaaaatggt attttgaagt gactttagat catatggagc aaaccaccca    120
tatgacaccg catctaagaa ttggctgggc taacacttct ggttatgttc cctttcctgg    180
cggtggtgaa aaatggggcg taatggagt tggtgatgat ctctactctt ttggttttga    240
tggagctgca ttatggacag gtggaagaaa aactgtagtc cttcctcatg ctatggaacc    300
ttacataaga aagggagatg ttattggttg tgctttcgat ctgactgttc aattattac     360
atttactttt aatggaacat taatccgagg atcatttagg gattttaatc tt            412

<210> SEQ ID NO 31
<211> LENGTH: 342
<212> TYPE: DNA
<213> ORGANISM: Artificial Sequence
<220> FEATURE:
<223> OTHER INFORMATION: Description of artificial sequence note =
      synthetic construct

<400> SEQUENCE: 31
atgtgaagga aagaaacta accacaagta taagatggaa cctgatacaa aattatttcc      60
agctatattt gttgaagcta caagcaaaga aattctacaa attgagcttg gtcgtacatc    120
aactacactg cctttatcag cagctgttct ccaaaattca gaaagacatg tcattcctca    180
gtttccacca agacttaaag ttcagtgtct aaaaccacat cagtgggcac gtgttcctaa    240
tatttcattg catgtccacg ctctgaaatt atcagatata agaggttgga gtatgctttg    300
tgaagatcca gtttcaatgt tagcattaca tatacctgaa ga                       342

<210> SEQ ID NO 32
<211> LENGTH: 432
<212> TYPE: DNA
<213> ORGANISM: Artificial Sequence
<220> FEATURE:
<223> OTHER INFORMATION: Description of artificial sequence note =
      synthetic construct

<400> SEQUENCE: 32
aggatggcaa agatgaacat cgtaagggtt tacttcaaat gaaaatggca gagggggcaa      60
aactacagat gtgctatctc ttacagcatt tatgcgatat acaattgcgg catcgggttg    120
aagccattat taatttagt tatgactata ttgctgatct tcagcaggat cagttgagaa     180
gatatgttga tattaagcag tctgatcttc catcatcagt tgctgcaaga aaaacaagag    240
agtttcgttg ccctccaaga gaacagatga atgctatcat aaattttaaa aatttagaag    300
aagatgacaa agaaaactgt ccatgtggtg aagaactgag ggagagatta acacatttc     360
atgaagaaac tatgagtaaa gtttcacttg ttgctctcca agagccacaa gaagatgaga    420
acggtgaaac ac                                                        432

<210> SEQ ID NO 33
<211> LENGTH: 367
<212> TYPE: DNA
<213> ORGANISM: Artificial Sequence
<220> FEATURE:
<223> OTHER INFORMATION: Description of artificial sequence note = synthetic construct

<400> SEQUENCE: 33

```
tctcccttttg ttgataaagc attaccagtt ttatagtggt gcagataact atgcaagtct    60
tttagatgct acacttcata cagtgtatcg cctatcaaaa aatcgaatgc taactaaagg   120
tcagcgagag gcagtatcag attttttggt tgctctcaca agtcaattac agccaagcat   180
gttactcaaa cttcttcgaa agttaaccgt tgatgtatca aagctttctg agtataccac   240
agttgcttta aggttgctta ctttacacta tgagcgttgt gcaaaatatt atggaactac   300
tggtggacaa gctggtggat ctagtgatga agaaaaaagg ctcactatgt tactcttcag   360
taatatt                                                              367
```

<210> SEQ ID NO 34
<211> LENGTH: 396
<212> TYPE: DNA
<213> ORGANISM: Artificial Sequence
<220> FEATURE:
<223> OTHER INFORMATION: Description of artificial sequence note = synthetic construct

<400> SEQUENCE: 34

```
gacttgctcg cttttttagaa acagctggta gtgttcttaa ctactttgaa cctttcctgg    60
gacgaattga aatattaggt agtagtaaac gaatcgagcg tgtatatttc gagattaaag   120
aatcaaatat tgaacagtgg gaaaaacctc aaatcaagga atctaaacga gcatttttct   180
attcaattgt cactgaagga ggtgacaaag aaaaattgga agcttttgtt aattttttgtg   240
aagatgccat atttgagatg acacatgcca gtgggcttat ggcaactgat gatggtacag   300
gctctggagg aggaaaacaa agagcatcct cttattctta tatggaagat gaagatgaag   360
aaaggaatcc aatcagacgt ggttggcaag caacta                              396
```

<210> SEQ ID NO 35
<211> LENGTH: 557
<212> TYPE: DNA
<213> ORGANISM: Artificial Sequence
<220> FEATURE:
<223> OTHER INFORMATION: Description of artificial sequence note = synthetic construct

<400> SEQUENCE: 35

```
aatttagaat caaatattat tgatactatt tcttttttcat actttacatt aatattcttc    60
aaaattaaaa atgccaggag tagagcatgt tactaacaaa gtcgttgttc atcctttagt   120
tctattaagt gttgttgatc atttcaatag aatgggtaaa attgggaatc agaagagagt   180
agttggcgta ttattaggat gctggaaggc aaaaggtgtt ttagacgtat ctaatagttt   240
tgcagtgcca tttgatgaag atgataaaga caaatcagtt tggttttttag accatgatta   300
tttagaaaat atgtatggca tgtttaagaa agttaatgca agagaaaaag ttgttggctg   360
gtatcataca ggcccaaagt tacatcaaaa tgatgttgca attaatgaac ttatacgccg   420
ttactgccct aactcagttc ttgttattat cgatgcaaaa ccaaggatc ttggtttacc   480
tacagaagca tatagagcag ttgaagaagt acatgatgat ggttctccta cgacaaaaac   540
atttgagcat gttccca                                                   557
```

<210> SEQ ID NO 36
<211> LENGTH: 530
<212> TYPE: DNA
<213> ORGANISM: Artificial Sequence
<220> FEATURE:
<223> OTHER INFORMATION: Description of artificial sequence note = synthetic construct

<400> SEQUENCE: 36

```
atgaacttat acgccgttac tgccctaact cagttcttgt tattatcgat gcaaaaccaa      60
aggatcttgg tttacctaca gaagcatata gagcagttga agaagtacat gatgatggtt     120
ctcctacgac aaaaacattt gagcatgttc ccagtgaaat aggggctgaa gaagcagagg     180
aagtgggtgt tgaacatctg ctgagagata taaaagatac aactgtcggc tcactttcgc     240
aaagggttac taatcaattt cttggtctca aaggccttaa tcaacaaatt caagacatca     300
gggattacct tatgcaggtt gttgaaggaa aattgcccat caaccatcaa ataatatatc     360
agcttcaaga catatttaat ctccttcctg acatgaacca tgggaacttt gttgattcat     420
tatacataaa aacaaatgat cagatgcttg tcgtttatct cgctgccctc gttagagcta     480
ttgttgcctt gcataatctg atcaataata aactcagtaa tcgtgatgcc              530
```

<210> SEQ ID NO 37
<211> LENGTH: 544
<212> TYPE: DNA
<213> ORGANISM: Artificial Sequence
<220> FEATURE:
<223> OTHER INFORMATION: Description of artificial sequence note = synthetic construct

<400> SEQUENCE: 37

```
tacttcattg tcataaaggg gtaacattgc tgaatccagc gtaaaggtta cagtgactct      60
cacctggtta taacagtttt gctttgtaat catgggttct gagagatata gcttttcttt     120
gactactttc agtccatctg gaaaattagt tcaaattgag tatgcacttg ccgcagtcgc     180
agctggagct ccatcaatcg gtatcagagc atccaatgga gttgtattgg ctactgaaaa     240
caaatacaaa tcaattttat atgaagaaca tactattcaa aaagtagaaa tgataactaa     300
acacattgga atggtctaca gtggaatggg acctgattat aggctactag tgaagagagc     360
tagaaaaatg gctcaacaat aacagttagt ttacggtgag cctattccta ctgcacagct     420
tgttcaacga gttgccatgg ttatgcagga gtacactcaa tctggaggtg ttagaccttt     480
tggagttct ttactcattg ccgggtggga tggggataaa ccatctctgt ttcaatgtga     540
tcca                                                                 544
```

<210> SEQ ID NO 38
<211> LENGTH: 587
<212> TYPE: DNA
<213> ORGANISM: Artificial Sequence
<220> FEATURE:
<223> OTHER INFORMATION: Description of artificial sequence note = synthetic construct

<400> SEQUENCE: 38

```
acacattgga atggtctaca gtggaatggg acctgattat aggctactag tgaagagagc      60
tagaaaaatg gctcaacaat aacagttagt ttacggtgag cctattccta ctgcacagct     120
tgttcaacga gttgccatgg ttatgcagga gtacactcaa tctggaggtg ttagaccttt     180
tggagttct ttactcattg ccgggtggga tggggataaa ccatctctgt ttcaatgtga     240
```

```
tccatctgga gcatactttg cctggaaagc tactgcaatg ggaaaaaatt ttgtcactgg       300
caaaacattt ctagaaaaga ggtacagtga aactttagag ctggatgatg cagtacatac       360
tgcaattctc actcttaaag aaaactttga aggccaaatg acttcggaca atatcgaggt       420
cggagtttgt gatgatcaag ggttcagagt tttagatcct acaacagtga aggattatct       480
ggctaatatt ccataaattt attattaaaa tttgatttta taattaataa aaggtgatt       540 gcttatggat atgtgtgatg cctaaataaa atattatttt ttattgg                    587

<210> SEQ ID NO 39
<211> LENGTH: 550
<212> TYPE: DNA
<213> ORGANISM: Artificial Sequence
<220> FEATURE:
<223> OTHER INFORMATION: Description of artificial sequence note =
      synthetic construct

<400> SEQUENCE: 39
atcattgatg atggttgaga agttccaga ctctacatat gaaatggttg gaggtcttga        60
taagcaaatt aaggaaatca agaagtaat tgaacctcct gtaaaacatc cagaactgtt       120
tgatgcacta ggaatagctc agcccaaagg agttttatta tatggaccac ctggaacagg     180
taaaacactt ttggcaagag cagttgccca tcacactgag tgcacgttca ttcgtgtgtc      240
aggatctgag ttggttcaga aattcattgg ggaaggatcc agaatggtta gagaattgtt    300
cgtcatggca agggaacatg ctccatctat catatttatg gatgaaatcg attcaatagg    360
ttcatcacgt atcgaatctg ggagtggtgg tgattctgaa gtccagagaa caatgttaga    420
gttattgaac caattggatg gcttcgaagc cacaaaaaat attaaggtca taatggccac    480
taataggatt gatattttgg accctgctct tctgcgtcct ggaaggatag atcgtaagat    540
tgagttcccc                                                           550

<210> SEQ ID NO 40
<211> LENGTH: 580
<212> TYPE: DNA
<213> ORGANISM: Artificial Sequence
<220> FEATURE:
<223> OTHER INFORMATION: Description of artificial sequence note =
      synthetic construct

<400> SEQUENCE: 40
tccatctatc atatttatgg atgaaatcga ttcaataggt tcatcacgta tcgaatctgg       60
gagtggtggt gattctgaag tccagagaac aatgttagag ttattgaacc aattggatgg    120
cttcgaagcc acaaaaaata ttaaggtcat aatggccact aataggattg atattttgga    180
ccctgctctt ctgcgtcctg gaaggataga tcgtaagatt gagttccccc accaaatga    240 ggaagctcgt ttagatatcc ttagaattca ttcacgtaaa atgaatctta cccggggtat    300
caacttgcgt aaaattgccg agctcatgcc tggagcttca ggtgcagaag taaagggtgt    360
ctgtactgaa gcagggatgt atgccctgag ggagaggaga atccatgtca cccaagaaga    420
tttcgaaatg gctgtggcca aggttatgca aaaggactcc gagaagaata tgtcaatcaa    480
gaaattatgg aaataaacga ctcacttatt tttttttttt tttactctgt ttaaaaagct    540
ttaaatatat agatgtttgt gaggttttgt taaaaataaa                          580
```